(12) United States Patent
Adamo et al.

(10) Patent No.: US 9,149,541 B2
(45) Date of Patent: Oct. 6, 2015

(54) TYROSINE LIGATION PROCESS

(75) Inventors: Roberto Adamo, Siena (IT); Martin Allen, Cambridge, MA (US); Francesco Berti, Siena (IT); Elisa Danieli, Siena (IT); Qi-Ying Hu, Cambrdige, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/131,150

(22) PCT Filed: Jul. 5, 2012

(86) PCT No.: PCT/US2012/045549
§ 371 (c)(1),
(2), (4) Date: Jan. 6, 2014

(87) PCT Pub. No.: WO2013/009564
PCT Pub. Date: Jan. 17, 2013

(65) Prior Publication Data
US 2014/0141034 A1    May 22, 2014

Related U.S. Application Data

(60) Provisional application No. 61/505,778, filed on Jul. 8, 2011.

(51) Int. Cl.
 *A61K 38/04*  (2006.01)
 *A61K 39/385* (2006.01)
 *A61K 47/48*  (2006.01)
 *C07K 5/00*   (2006.01)
 (Continued)

(52) U.S. Cl.
 CPC ........... *A61K 47/4833* (2013.01); *A61K 39/385* (2013.01); *A61K 47/482* (2013.01); *A61K 47/48007* (2013.01); *A61K 47/4823* (2013.01); *A61K 47/48023* (2013.01); *A61K 47/48092* (2013.01); *A61K 47/48238* (2013.01); *A61K 47/48246* (2013.01); *A61K 47/48261* (2013.01); *A61K 2039/505* (2013.01)

(58) Field of Classification Search
 CPC ........... A61K 39/385; A61K 47/4833; A61K 47/4823; A61K 47/48261; A61K 47/48246; A61K 47/48007; A61K 47/48023; A61K 47/48092; A61K 47/48238; A61K 47/482; A61K 2039/505
 See application file for complete search history.

(56) References Cited

U.S. PATENT DOCUMENTS

2009/0043077 A1\* 2/2009 Berti .............................. 530/363

FOREIGN PATENT DOCUMENTS

EP       477508       4/1992
WO    WO 03/097091   11/2003
(Continued)

OTHER PUBLICATIONS

Hitoshi Ban et al., "Tyrosine Bioconjugation through Aqueous Ene-Type Reactions: A Click-Like Reaction for Tyrosine" *Journal of the American Chemical Society* 132(5):1523-1525, Feb. 10, 2010.
(Continued)

*Primary Examiner* — Karlheinz R Skowronek
*Assistant Examiner* — Catherine Mader
(74) *Attorney, Agent, or Firm* — Rona Nardone

(57) ABSTRACT

A process is provided for preparing a conjugate of Formula (I-A) or (I) comprising a polypeptide containing n number of tyrosine units, where n is an integer greater than or equal to 1, dispersed within the amino acid chain having and amino terminus end ($A^1$) and an acid terminus end ($A^2$) of the protein or polypeptide and having a weight average molecular weight equal to or greater than 10,000 Daltons (10 kDa), wherein the conjugate comprises a number m of tyrosine conjugates (modified tyrosine residues) as depicted in Formula (I-A) or (I), where m is at least one and is less than or equal to n:

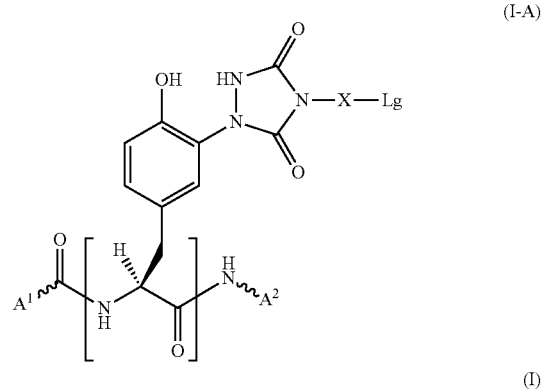

(I-A)

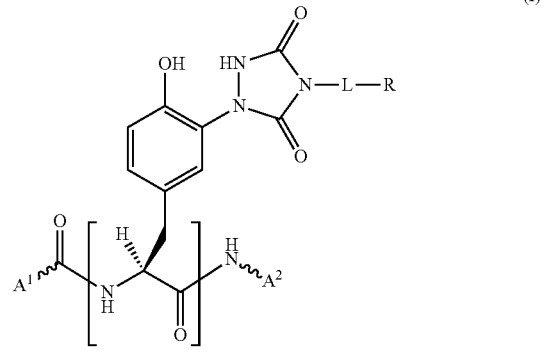

(I)

where X, Lg, L and R are as defined herein.

2 Claims, 5 Drawing Sheets

(51) Int. Cl.
*C07K 17/00* (2006.01)
*A61K 39/00* (2006.01)

(56) References Cited

FOREIGN PATENT DOCUMENTS

| WO | WO 2006/082530 | | 8/2006 | | |
|---|---|---|---|---|---|
| WO | WO/2006/082530 | * | 10/2006 | ............. | A61K 47/48 |
| WO | WO/2011/079315 | * | 6/2011 | ........... | A61K 31/675 |
| WO | WO 2011/079315 | | 6/2011 | | |

OTHER PUBLICATIONS

Neel S. Joshi et al., "A Three-Component Mannich-Type Reaction for Selective Tyrosine Bioconjugation" *The Journal of the American Chemical Society 126*(49):15942-15943, Dec. 1, 2004.

* cited by examiner

1. CRM
2. 7A
3. Conjugate of 7A with azide modified-saccharide 4

1. CRM
2. 7A
3. A

1. CRM
2. 13A
3. B

TYROSINE LIGATION PROCESS

CROSS-REFERENCE TO RELATED APPLICATIONS

This application is the U.S. National Stage of International Application No. PCT/US2012/045549, filed Jul. 5, 2012, which claims the benefit of priority to U.S. Provisional Application No. 61/505,778, filed Jul. 8, 2011, the contents of which are incorporated herein by reference.

FIELD OF THE INVENTION

The present invention provides a tyrosine ligation process and the crosslinking agents used to form tyrosine-containing polypeptide conjugates.

BACKGROUND

Conjugation has been widely used to optimize the properties of biologically active proteins, such as protein/peptide therapies, antibody-drug conjugates, vaccines, tissue selective targeting vehicles, molecular diagnostics, and protein nucleic acid conjugates.

Traditional conjugation method utilizes lysine based covalent ligation, which is difficult to achieve homogenicity due to the abundance of lysines on the surface. The other typical method is based on cystein conjugation. However, cystein is a rare amino acid and usually present in disulfide form, and free cystein can potentially lead to disulfide scrambling.

Tyrosines represent better alternative conjugation sites. They are rarer than lysines, and not all of them are surface exposed. A few methods have been reported recently for tyrosine ligation, such as allylic alkylation, diazo-coupling and Mannich-type coupling. See, for example, *J Am Chem Soc*, 128, 1080-1081 (2006); *J Am Chem Soc*, 127, 3718-3723 (2005); and *Bioconjugate Chem*, 19, 153-157 (2008)).

A tyrosine ligation method was recently described by Ban, H., et al. in *J Am Chem Soc*, 132, 1523-1525 (2010). However, the predominant product observed using the published protocol (a Phosphate Buffered Saline (PBS) solution) is most likely urea formation at lysines. The LC-MS in the publication is inconsistent with the proposed tyrosine ligation product.

SUMMARY

Applicants have discovered that the use of a Tris buffer in the tyrosine ligation instead of PBS provides the desired tyrosine ligation product within a short timeframe.

In one embodiment of the present invention, a process is provided for preparing a conjugate of Formula (I-A) comprising a polypeptide (or a protein) containing n number of tyrosine units, where n is an integer greater than or equal to 1, dispersed within the amino acid chain $$(\sim\sim\sim)\text{-}(\sim\sim\sim)$$

having an amino terminus end ($A^1$) and an acid terminus end ($A^2$) of the protein or polypeptide (either the amino or acid terminus end can be the at least one tyrosine unit) and having a weight average molecular weight equal to or greater than 10,000 Daltons (10 kDa);

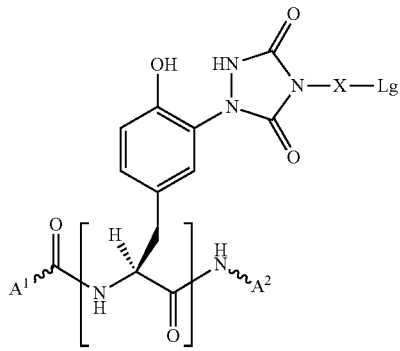

where

X is a spacer having a terminal active linking group (Lg),

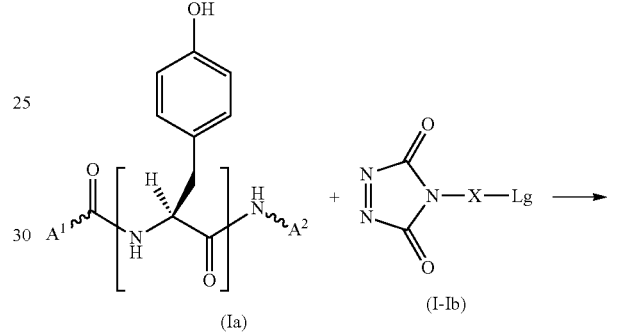

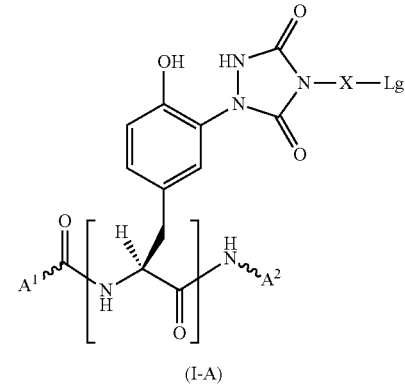

wherein said process comprises the step of reacting a protein or polypeptide of Formula (Ia) containing n number of tyrosine units with at least one 4-substituted-3H-1,2,4-triazole-3,5(4H)-dione of Formula (I-Ib) in the presence of a tris (hydroxymethyl)aminomethane (Tris) buffer at a pH of about 6.0 to about 9.0 to produce the conjugate of Formula (I-A) containing m number of conjugated tyrosine units, where m is an integer equal to or less than n and preferably greater than or equal to 1.

In another aspect of the present invention, a conjugate of Formula (I-A) is provided which is prepared by the process described above.

In another embodiment of the present invention, a process is provided for preparing a conjugate of Formula (I) comprising a protein or polypeptide containing n number of tyrosine units, where n is an integer greater than or equal to 1, dispersed within the amino acid chain having an amino terminus end ($A^1$) and an acid terminus end ($A^2$) of the protein or polypeptide and having a weight average molecular weight equal to or greater than 10,000 Daltons and where said conjugate of Formula (I) contains m number of tryrosine conjugates, where m is an integer less than n (or, in some embodiments, m is an integer equal to n) and is preferably at least 1;

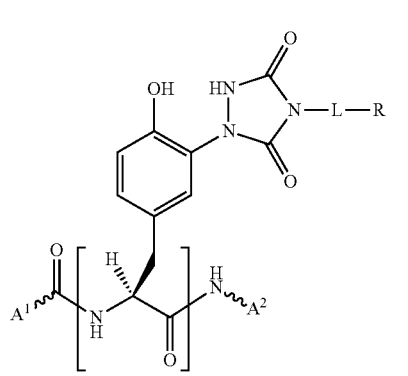

where L is a linker comprising a spacer X' (defined herein), and R is a therapeutic agent, radiolabeled-therapeutic agent, fluorescent agent, cytotoxic agent, DNA, RNA, lipid, hapten, or a polymer (e.g., a polyethyleneglycol (PEG) (also known as polyethylene oxide (PEO) or polyoxyethylene (POE)), or a polysaccharide);

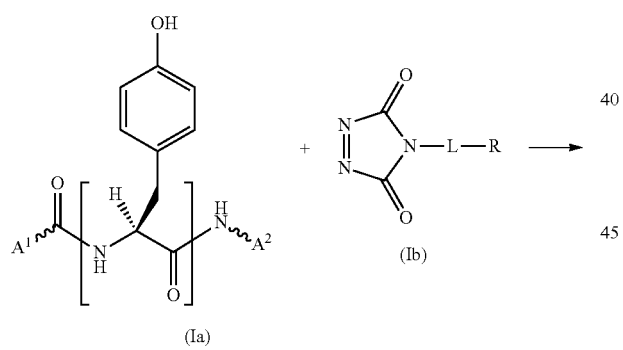

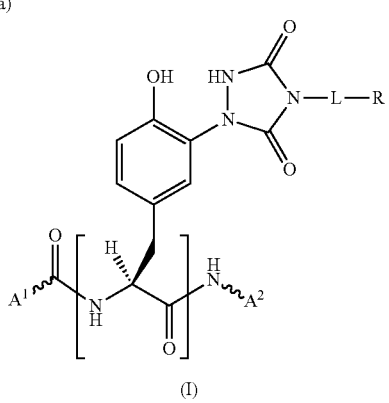

wherein said process comprises the step of reacting a protein or polypeptide of Formula (Ia) containing n number of tyrosine units with at least one 4-substituted-3H-1,2,4-triazole-3,5(4H)-dione of Formula (Ib) in the presence of a tris (hydroxymethyl)aminomethane (Tris) buffer at a pH of about 6.0 to about 9.0 to produce the conjugate of Formula (I) containing m number of conjugated tyrosine units, where m is an integer equal to or less than n and preferably at least 1.

In yet another embodiment, a process for preparing a conjugate of Formula (I) (described above) is provided which comprises the step of reacting a conjugate of Formula (I-A) with $R^L$ to form a conjugate of Formula (I)

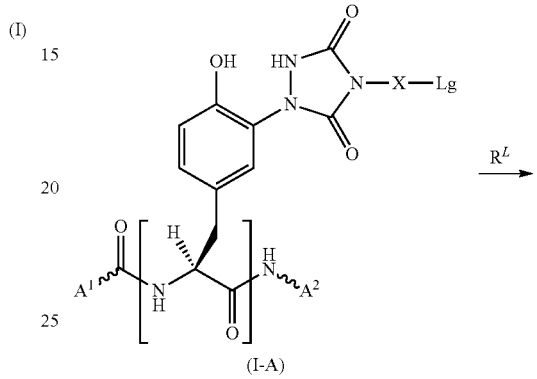

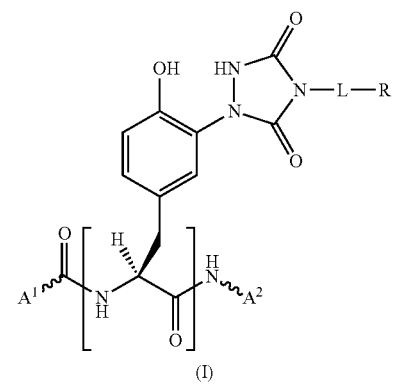

where X, Lg, $A^1$, $A^2$, L and R are as defined herein, and $R^L$ is R optionally substituted with a substituent capable of reacting with linking group (Lg). When a substituent is not present, then it is understood that R contains a binding site capable of reacting with linking group (Lg).

Another aspect of the present invention provides a conjugate of Formula (I-A) comprising a polypeptide containing n number of tyrosine units, where n is an integer greater than or equal to 1, dispersed within the amino acid chain having an amino terminus end ($A^1$) and an acid terminus end ($A^2$) of the protein or polypeptide and having a weight average molecular weight equal to or greater than 10,000 Daltons;

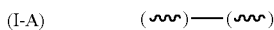

(I-A)

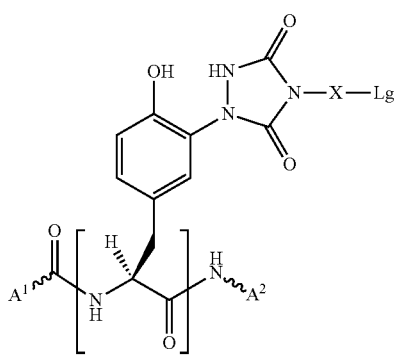

where X is a spacer having a terminal active linking group (Lg);

wherein said conjugate of Formula (I-A) is prepared by a process comprising the step of reacting a protein or polypeptide of Formula (Ia) containing n number of tyrosine units with at least one 4-substituted-3H-1,2,4-triazole-3,5(4H)-dione of Formula (I-Ib) in the presence of a tris(hydroxymethyl) aminomethane buffer at a pH of about 6.0 to about 9.0 to produce the conjugate of Formula (I-A) containing m number of conjugated tyrosine units, where m is an integer equal to or less than n, and preferably m is at least 1;

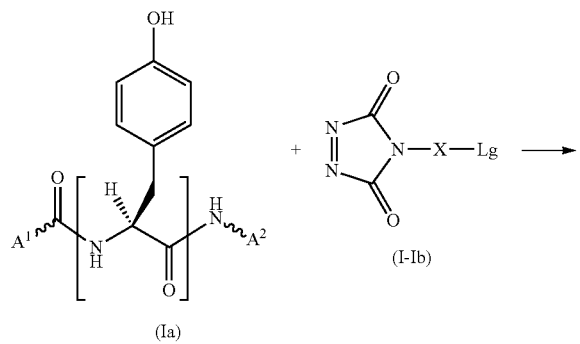

(Ia)   (I-Ib)

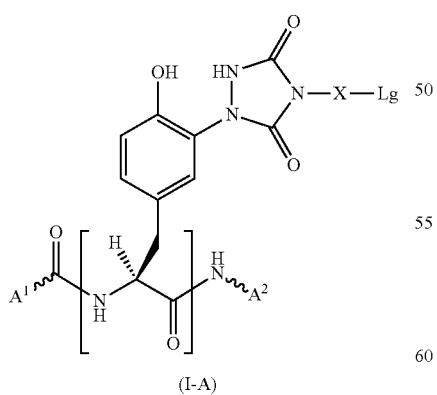

(I-A)

Yet another aspect of the invention provides a conjugate of Formula (I) comprising a polypeptide containing n number of tyrosine units, where n is an integer greater than or equal to 1, dispersed within the amino acid chain having an amino terminus end ($A^1$) and an acid terminus end ($A^2$) of the protein or polypeptide and having a weight average molecular weight equal to or greater than 10,000 Daltons and where said conjugate of Formula (I) contains m number of tryrosine conjugates, where m is an integer less than n and preferably m is at least 1;

(I)

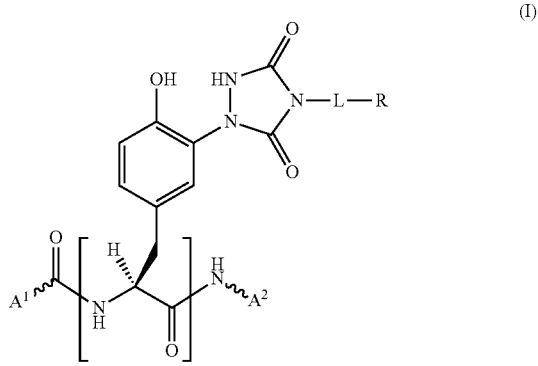

where L is a linker comprising a spacer X', and R is a therapeutic agent, radiolabeled-therapeutic agent, a fluorescent agent, cytotoxic agent, DNA, RNA, lipid, hapten, or a polymer;

wherein said conjugate of Formula (I) is prepared by a process comprising the step of reacting a conjugate of Formula (I-A) with $R^L$ to form a conjugate of Formula (I)

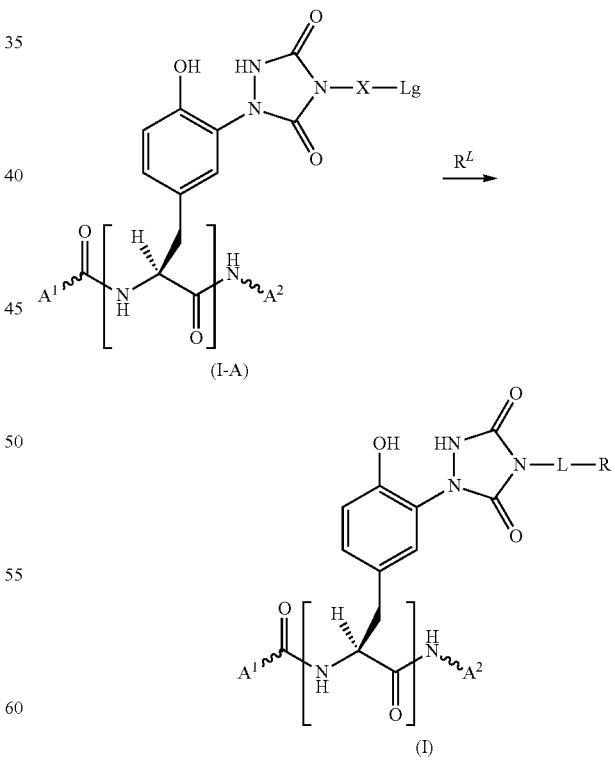

where

X is a spacer having a terminal active linking group (Lg), and $R^L$ is R optionally substituted with a substituent capable of reacting with linking group (Lg);

provided that X-Lg is not

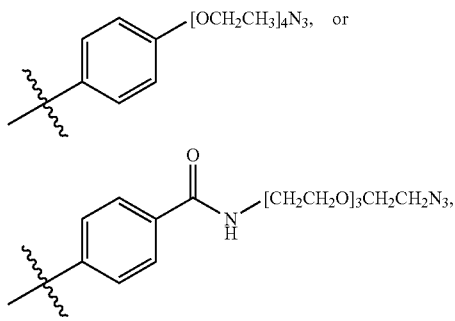

when said polypeptide is chymotrypsinogen A, myoblobin or bovine serum albumin and R is a rhodamine dye, or when said polypeptide is herceptin and R is an integrin binding cyclic arginine-glycine-aspartic (RGD) peptide. Sometimes, when said polypeptide is chymotrypsinogen A, myoblobin or bovine serum albumin and R is a rhodamine dye, or when said polypeptide is herceptin and R is an integrin binding cyclic arginine-glycine-aspartic (RGD) peptide, X-Lg may also not be

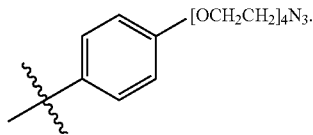

Yet another aspect of the invention provides a conjugate of Formula (I-A) comprising a polypeptide containing n number of tyrosine units, where n is an integer greater than or equal to 1, dispersed within the amino acid chain

having an amino terminus end ($A^1$) and an acid terminus end ($A^2$) of the protein or polypeptide and having a weight average molecular weight equal to or greater than 10,000 Daltons, and containing a number m of conjugated tyrosine residues where m is less than or equal to n and the conjugated tyrosine residues are of this formula;

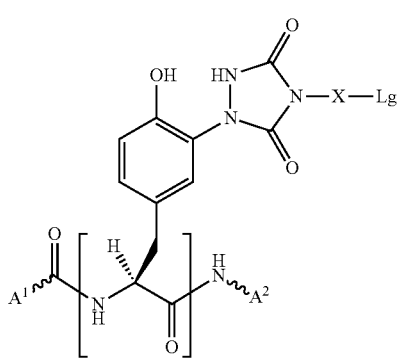

where X is a spacer having a terminal active linking group (Lg). In some such embodiments, the polypeptide is an antigenic polypeptide, a carrier peptide suitable for use in a vaccine, or an antibody or antibody fragment. In preferred embodiments, the conjugate has more modified tyrosine residues conjugated to Lg groups than lysine residues conjugated to Lg groups, i.e., the number of lysine residues conjugated to an Lg group is t, where t is less than m.

Yet another aspect of the invention provides a conjugate of Formula (I) comprising a polypeptide containing n number of tyrosine units, where n is an integer greater than or equal to 1, dispersed within the amino acid chain

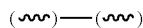

having an amino terminus end ($A^1$) and an acid terminus end ($A^2$) of the protein or polypeptide and having a weight average molecular weight equal to or greater than 10,000 Daltons and where said conjugate of Formula (I) contains m number of tryrosine conjugates, where m is an integer less than n;

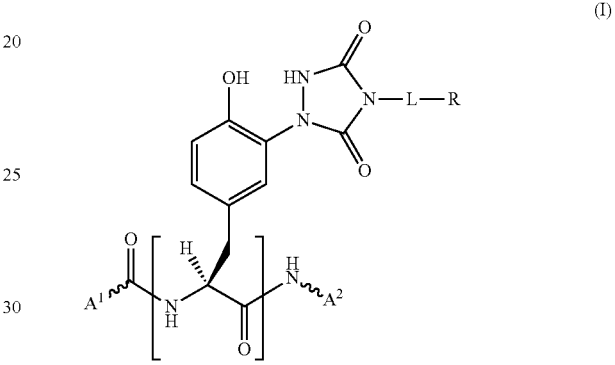

where L is a linker comprising a spacer X', and R is a therapeutic agent, radiolabeled-therapeutic agent, a fluorescent agent, cytotoxic agent, DNA, RNA, lipid, hapten, or a polymer. In some such embodiments, the polypeptide is an antigenic polypeptide, a carrier peptide suitable for vaccine use, or an antibody or antibody fragment. In preferred embodiments, the polypeptide has more modified tyrosine residues conjugated to R groups than lysine residues conjugated to R groups. In preferred embodiments, the conjugate has more modified tyrosine residues conjugated to Lg groups than lysine residues conjugated to R groups, i.e., the number of lysine residues conjugated to an R group is t, where t is less than m.

Yet another aspect of the invention provides a conjugate of Formula (Xa) or (Xb) comprising an antibody or antibody fragment that comprises at least one conjugated tyrosine residue of the formula

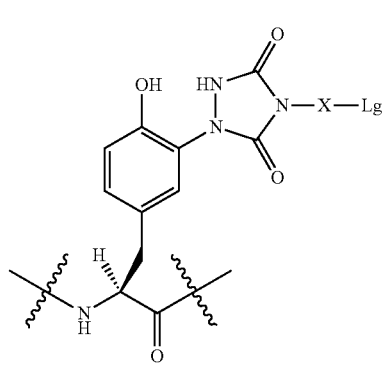

OR

-continued

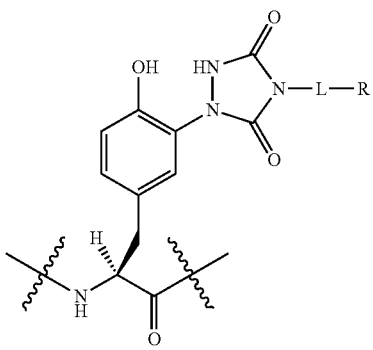

(Xb)

wherein R, X, L and Lg are as defined herein. In preferred embodiments, the antibody or antibody fragment has more modified tyrosine residues than modified lysine residues.

Yet another aspect of the present invention provides a conjugate of Formula (I) comprising a polypeptide containing n number of tyrosine units, where n is an integer greater than or equal to 1, dispersed within the amino acid chain (∿∿∿)—(∿∿∿)

having an amino terminus end ($A^1$) and an acid terminus end ($A^2$) of the protein or polypeptide and having a weight average molecular weight equal to or greater than 10,000 Daltons and where said conjugate of Formula (I) contains m number of tryrosine conjugates, where m is an integer less than n and preferably greater than or equal to 1;

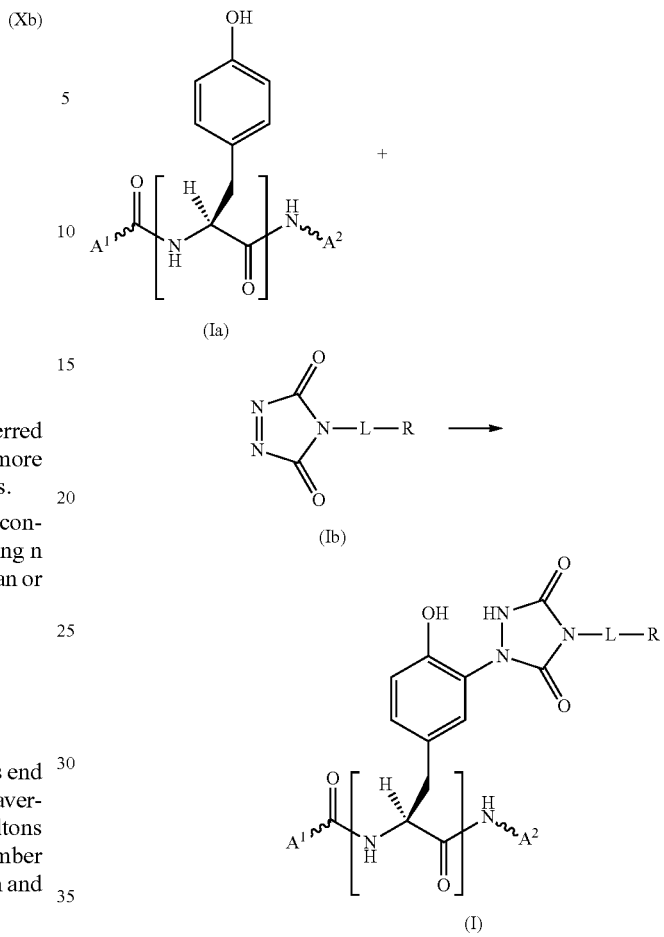

where

L is a linker comprising a spacer X', and R is a therapeutic agent, radiolabeled-therapeutic agent, a fluorescent agent, cytotoxic agent, DNA, RNA, lipid, hapten, or a polymer;

wherein said conjugate of Formula (I) is prepared by a process comprising the step of reacting a protein or polypeptide of Formula (Ia) containing n number of tyrosine units with at least one 4-substituted-3H-1,2,4-triazole-3,5(4H)-dione of Formula (Ib) in the presence of a tris(hydroxymethyl)aminomethane buffer at a pH of about 6.0 to about 9.0 to produce the conjugate of Formula (I) containing m number of conjugated tyrosine units, where m is an integer equal to or less than n provided that R is not a rhodamine dye when said polypeptide is chymotrypsinogen A, myoblobin or bovin serum albumin, and R is not an integrin binding cyclic arginine-glycine-aspartic (RGD) peptide when said polypeptide is herceptin.

In any one of the embodiments described above, the Tris buffer is alternatively (i) a TBE buffer solution comprising tris(hydroxymethyl)aminomethane, boric acid and ethylenediaminetetraacetic acid (EDTA); (ii) a TAE buffer solution comprising tris(hydroxymethyl)aminomethane, acetic acid and EDTA; or (iii) tris(hydroxymethyl)aminomethane and a nucleophilic amine (e.g., methylamine or diethylamine).

In any one of the embodiments described above, the polypeptide is an antibody.

In another alternative for each of the embodiments described above the polypeptide is an antigenic peptide.

In certain embodiments, the peptide is a carrier protein useful for promoting an immune response, such as CRM197, GBS59 or GBS80.

In one particular embodiment for each of the embodiments described above, X is a spacer selected from the group consisting of (a) a bond, —O—, —S—, —NH—, —N(($C_1$-$C_6$)alkyl)-, —NH—C(O)—NH—, —C(O)—NH—, —NH—C(O)—;

(b) ($C_1$-$C_{20}$)alkylene, ($C_2$-$C_{20}$)alkenylene, ($C_2$-$C_{20}$)alkynylene, —Z—($C_1$-$C_{20}$)alkylene-, —Z—($C_2$-$C_{20}$)alkenylene, —Z—($C_2$-$C_{20}$)alkynylene, ($C_1$-$C_{20}$)alkylene-Z—($C_1$-$C_{20}$) alkylene, ($C_2$-$C_{20}$)alkenylene-Z—($C_2$-$C_{20}$)alkenylene, ($C_2$-$C_{20}$)alkynylene-Z—($C_2$-$C_{20}$)alkynylene, where Z is —NH—, —N(($C_1$-$C_6$)alkyl)-, —NH—C(O)—NH—, —C(O)—NH—, —NH—C(O)—, (C₃-C₇)cycloalkylene, phenylene, heteroarylene, or heterocyclene and where said (C₁-C₂₀)alkylene, said (C₂-C₂₀)alkenylene, and said (C₂-C₂₀)alkynylene moieties each independently optionally contain 1-10 oxygen atoms interdispersed within said moieties;

(c) (C₃-C₇)cycloalkylene, (C₃-C₇)cycloalkylene-Y—(C₃-C₇)cycloalkylene, —Y—(C₃-C₇)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is (C₁-C₂₀)alkylene, (C₂-C₂₀)alkenylene, (C₂-C₂₀)alkynylene, —O—, —C(O)—, —S—, —NH—, —N((C₁-C₆)alkyl)-, —NH—C(O)—NH—, —C(O)—NH—, or —NH—C(O)— and where said (C₃-C₇)cycloalkylene, said phenylene, said heteroarylene, and said heterocyclene moieties are each individually optionally substituted with 1 to 3 substituents selected from halo, (C₁-C₄)alkyl or halo-substituted(C₁-C₄)alkyl;

(d) —[OCH₂CH₂]ᵥ—, where v is 1-2,000; and (e) a peptide comprising 1 to 30 amino acids.

In one particular embodiment for each of the embodiments described above, Lg is a linking agent selected from the group consisting of halogen, —C≡CH, —C=CH₂, —OH, —SH, —SO₂—CH=CH₂, —O—NH₂, —N₃, —O—P(O)(OH)₂, —C(O)—H, —C(O)—CH₃, —NH—C(O)—CH₂—I, maleimidyl, 3,5-dioxo-1,2,4-triazolidin-4-yl, 1H-pyrrole-2,5-dione-1-yl, pyridin-2-yl-disulfanyl, tetrahydro-1H-thieno[3,4-d]imidazol-2(3H)-one-4-yl, 1-carbonyloxy-2,5-dioxopyrrolidine, sodium 1-carbonyloxy-2,5-dioxopyrrolidine-3-sulfonate, —SSR¹, —C(O)—OR¹, —N(R¹)H, —NH—N(R¹)H, where R¹ is H or (C₁-C₆)alkyl, and —C(O)—R², where R² is H, (C₁-C₄)alkyl, halo-substituted(C₁-C₄)alkyl, —CH=CH₂, N(R¹)H, or —NH—N(R¹)H.

In one particular embodiment for each of the embodiments described above, L is a linker comprising a spacer X' selected from the group consisting of (a) a bond, —O—, —S—, —NH—, —N((C₁-C₆)alkyl)-, —NH—C(O)—NH—, —C(O)—NH—, —NH—C(O)—;

(b) (C₁-C₂₀)alkylene, (C₂-C₂₀)alkenylene, (C₂-C₂₀)alkynylene, —Z—(C₁-C₂₀)alkylene-, —Z—(C₂-C₂₀)alkenylene, —Z—(C₂-C₂₀)alkynylene, (C₁-C₂₀)alkylene-Z—(C₁-C₂₀)alkylene, (C₂-C₂₀)alkenylene-Z—(C₂-C₂₀)alkenylene, (C₂-C₂₀)alkynylene-Z—(C₂-C₂₀)alkynylene, where Z is —NH—, —N((C₁-C₆)alkyl)-, —NH—C(O)—NH—, —C(O)—NH—, —NH—C(O)—, (C₃-C₇)cycloalkylene, phenylene, heteroarylene, or heterocyclene and where said (C₁-C₂₀)alkylene, said (C₂-C₂₀)alkenylene, and said (C₂-C₂₀)alkynylene moieties each independently optionally contain 1-10 oxygen atoms interdispersed within said moieties;

(c) (C₃-C₇)cycloalkylene, (C₃-C₇)cycloalkylene-Y—(C₃-C₇)cycloalkylene, —Y—(C₃-C₇)cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is (C₁-C₂₀)alkylene, (C₂-C₂₀)alkenylene, (C₂-C₂₀)alkynylene, —O—, —C(O)—, —S—, —NH—, —N((C₁-C₆)alkyl)-, —NH—C(O)—NH—, —C(O)—NH—, or —NH—C(O)— and where said (C₃-C₇)cycloalkylene, said phenylene, said heteroarylene, and said heterocyclene moieties are each individually optionally substituted with 1 to 3 substituents selected from halo, (C₁-C₄)alkyl or halo-substituted(C₁-C₄)alkyl;

(d) —[OCH₂CH₂]ᵥ—O—, where v is 1-2,000; and (e) a peptide comprising 1 to 30 amino acids.

In yet another aspect of the present invention a conjugate of Formula (Ib) is provided

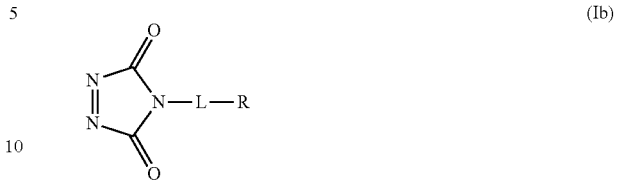

(Ib)

wherein L is a linker comprising a spacer X', and R is a therapeutic agent, radiolabeled-therapeutic agent, a fluorescent agent, cytotoxic agent, DNA, RNA, lipid, hapten, or a polymer;

provided that R is not a rhodamine dye or an integrin binding cyclic arginine-glycine-aspartic (RGD) peptide.

DEFINITIONS

As used herein, the term "alkyl" refers to a hydrocarbon moiety of the general formula $C_nH_{2n+1}$. The alkane group may be straight or branched. For example, the term "(C₁-C₁₀) alkyl" refers to a monovalent, straight, or branched aliphatic group containing 1 to 10 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like). Similarly, the alkyl portion (i.e., alkyl moiety) of an alkoxy have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls). "Halo-substituted alkyl" refers to an alkyl group having at least one halogen substitution.

The term "alkenyl" refers to an alkyl moiety containing at least one unsaturation in the alkyl group. The alkenyl group may be straight or branched. For example, vinyl, prop-1-enyl, prop-2-enyl, allenyl, 2-methylprop-2-enyl, 3-methylbut-2-enyl, butadienyl, and the like.

The term "alkynyl" refers to an alkyl moiety containing at least one triple bond. The alkynyl group may be straight or branched. For example, CH₃—C≡C—, H—C≡C—CH₂—, CH₃—C≡C—CH₂—, H—C≡C—CH(CH₃)—, H—C≡C—CH₂CH₂—, H—C≡C—CH(CH₃)CH₂—, H—C≡C—CH₂—C≡C—CH₂—, and the like.

The term "alkylene" or "alkylenyl" refers to an alkyl moiety where the moiety contains two binding sites. The alkylene group may be straight (e.g., —(CH₂)—, —(CH₂)₂—, —(CH₂)₃—, or branched (e.g., —CH(CH₃)—, —C(CH₃)₂—, —CH₂CH (CH₃)—, —CH(CH₃)—CH₂—, —C(CH₃)₂—CH₂—, etc.). Suitable alkylene moieties are the same as those described above for alkyl except with two binding sites instead of just one.

The term "alkenylene" or "alkenylenyl" refers to an alkenyl moiety containing two binding sites. For example, —CH₂—CH=CH—CH₂—, —CH=CH—CH=CH—, and the like. Suitable alkenylene moieties are the same as those described above for alkenyl except with two binding sites instead of just one.

The term "alkynylene" or "alkynylenyl" refers to an alkynyl moiety containing two binding sites. For example, —CH₂—C≡C—CH₂—. Suitable alkynylene moieties are the same as those described above for alkynyl except with two binding sites instead of just one.

The term "aryl" refers to aromatic moieties having a single (e.g., phenyl) or a fused ring system (e.g., naphthalene, anthracene, phenanthrene, etc.). A typical aryl group is a 6- to 14-membered aromatic carbocyclic ring(s). A fused aromatic ring system may also include a phenyl fused to a partially or fully saturated cycloalkyl. For example, 2,3-dihydroindenyl, 1,2,3,4-tetrahydronaphthalenyl, 1,2-dihydronaphthalenyl, 2,3-dihydronaphthalenyl, 9,10-dihydroanthracenyl, fluorenyl, and the like.

The term "arylene" refers to a carbocyclic aromatic moiety having two binding sites. Suitable arylenes include those groups described above for an aryl moiety except with two binding sites rather than one. For example, 1,2-phenylene, 1,3-phenylene, 1,4-phenylene, 1,3-naphthylene, 1,4-naphthylene, 1,5-naphthylene, 1,6-naphthylene, 1,7-naphthylene, 2,3-naphthylene, 2,4-napthylene, 2,5-naphthylene, 2,6-naphthylene, 2,7-naphthylene, 3,4-naphthylene, 3,5-naphthylene, 3,6-naphthylene, 3,7-naphthylene, etc. The two binding sites on the fused arylene system may be on the same ring or different rings.

The term "partially or fully saturated cycloalkyl" refers to a carbocyclic ring which is fully hydrogenated (e.g., cyclopropyl, cyclobutyl, cyclopentyl, cyclohexyl, cycloheptyl, cyclooctyl, etc.) or partially hydrogenated (e.g., cyclopropenyl, cyclobutenyl, cyclopentyl, cyclopenta-1,3-dienyl, cyclohexenyl, cyclohexa-1,3-dienyl, cyclohexa-1,4-dienyl, etc.). The carbocyclic ring may be a single ring (as described above), a bicyclic ring (e.g., octahydropentalenyl, bicyclo[1.1.1]pentanyl, bicyclo[2.1.1]hexanyl, bicyclo[2.1.1]hex-2-enyl, bicyclo[2.2.1]hept-2-enyl, bicyclo[2.2.1]heptanyl, bicyclo[2.2.2]octanyl, bicyclo[2.2.2]oct-2-enyl, bicyclo[2.2.2]octa-2,5-dienyl, etc.) or a spiral ring (e.g., spiro[2.2]pentanyl, etc.), and the like.

The term "partially or fully saturated cycloalkylene" refers to a carbocyclic ring having either no unsaturation in the ring (fully hydrogenated) or at least one unsaturation (partially hydrogenated) without being aromatic and contains two binding sites. Suitable ring systems include those described above for a partially or fully saturated cycloalkyl except having two bind sites instead of one. For example, 1,2-cyclopropyl, 1,2-cycloprop-1-enyl, 1,2-cyclobutyl, 1,3-cyclobutyl, 1,2-cyclobut-1-enyl, 3,4-cyclobut-1-enyl, 3,5-cyclopent-1-enyl, 1,4-cyclopenta-1,3-dienyl, 1,5-cyclopenta-1,3-dienyl, 1,2-cyclopenta-1,3-dienyl, 1,3-cyclopenta-1,3-dienyl, etc. The carbocyclic ring may be a single ring, a bicyclic ring, fused ring (e.g., decahydronaphthalene), or a spiral ring where the two binding sites on the bicyclic ring and spiral ring may be on the same ring or different rings. See, e.g., the illustration below.

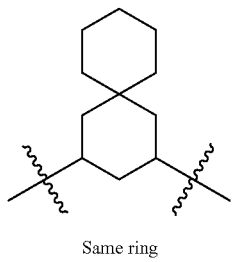

Same ring

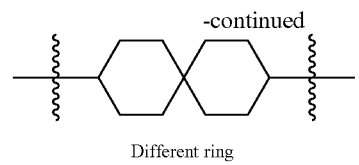

Different ring

The term "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 14-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, azetidinyl, tetrahydrofuranyl, dihydrofuranyl, dihydropyridinyl, pyrrolidinyl, imidazolidinyl, imidazolinyl, 1H-dihydroimidazolyl, hexahydropyrimidinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl, 1,4,7-triazonane, diazepanyl, 1,1-dioxide, oxazolidinyl, thiazolidinyl, octahydropyrrolo[3,2-b]pyrrolyl, decahydro-2,7-naphthyridinyl, and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like). Examples of spiral rings include 2,6-diazaspiro[3.3]heptanyl, 2,7-diazaspiro[4.4]nonanyl, 3-azaspiro[5.5]undecanyl, 3,9-diazaspiro[5.5]undecanyl, and the like.

The term "partially or fully saturated heterocyclene" refers to a partially or fully saturated heterocyclic ring (as described above) except having two binding sites instead of one. The heterocyclene ring may be a single ring, a bicyclic ring, or a spiral ring where the two binding sites on the bicyclic ring (including fused rings) and spiral ring may be on the same ring or different rings. See, e.g., the illustration below.

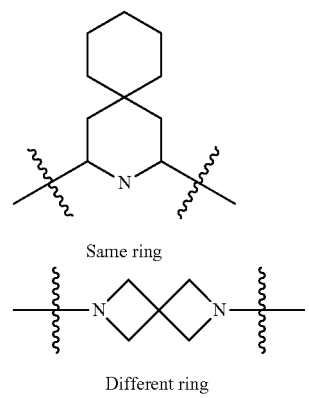

Same ring

Different ring

The term "heteroaryl" refers to aromatic moieties containing at least one heteratom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a hetereoaryl fused to an aryl (e.g., phenyl).

The term "heteroarylene" refers to a heteroaryl having two binding sites instead of one. Suitable heteroarylene groups include those described above for heteroaryl having two binding sites instead of one.

The term "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme I below provides potential routes for making the final tyrosine polypeptide conjugate (I) using the improved tyrosine ligation method. Although only a single tyrosine unit is depicted in the structures of the scheme below, one of skill in the art will understand that additional tryrosine units may be dispersed within the amino acid chain of the polypeptide (or protein) and that any or all of these tryosine units may be conjugated during the ligation process. In addition, those of skill in the art will appreciate that a distribution of tyrosine polypeptide conjugates (I) depending upon the degree of conjugation may be observed in the final reaction product.

Scheme 1

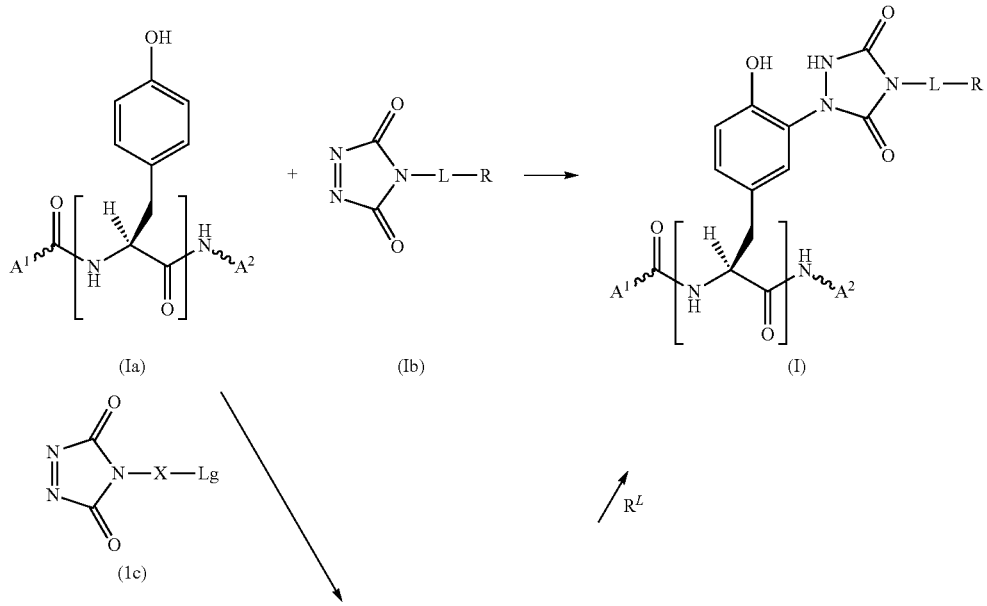

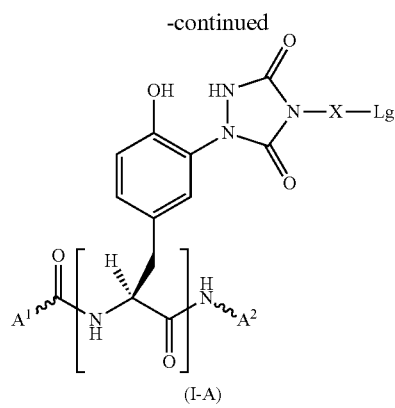

(I-A)

The tyrosine containing polypeptide (1a) in a Tris buffer (pH from about 6.0 to about 9.0, in particular from about 7.0 to about 8.0, more particularly from about 7.0 to about 7.5) is treated with 4-substituted-3H-1,2,4-triazole-3,5(4H)-dione (1 b) to form the desired conjugate of Formula (I). Alternatively, the tyrosine containing polypeptide (1a) can be treated with a 4-substituted-3H-1,2,4-triazole-3,5(4H)-dione (1c) having a spacer (X) with an active terminal linking group (Lg) to produce the intermediate conjugate polypeptide (I-A), which is subsequently conjugated via the terminal active linking group (Lg) to a desired R group (e.g., therapeutic agent, radiolabeled-therapeutic agent, cytotoxic agent, DNA, RNA, lipid, or a polymer, such as polyethyleneglycol or polysaccharide) by conventional methods well known to those of skill in the art (e.g. click chemistry, oxime formation, maleimide-thiol coupling, olefin metathesis, and alkylation) to form the conjugate of Formula (I). $R^L$ is generally an R group containing either a binding site or substituent capable of reacting with linking group (Lg). The terminal linking group (Lg) may or may not stay intact either wholly or partially with the spacer (X) to form "L" (comprising spacer X') in the final compound of Formula (I). Spacer X' comprises the residue of spacer X having a terminal linking group (Lg) after coupling with $R^L$. The type of method used to link R via $R^L$ to the intermediate conjugate polypeptide (I-A) will depend upon both the terminal linking group (Lg) and the particular moiety being conjugated. See, e.g., the various ligation reactions described by Tiefenbrunn and Dawson, in "Invited Review: Chemoselective Ligation Techniques: Modern Application of Time-Honored Chemistry" *Peptide Science* 94(1) 95-106 (2010), such as Huisgen [3+2] cycloaddition, Photoinducible tetrazole ligations, Staudinger ligations, Diels-Adler cycloadditions, Inverse-electron demand Diels-Adler, Hydrazone and oxime formation, Mannich condensation with tyrosine residues, Thiol-ene reactions, and Allyl sulfide cross-metathesis.

The 4-substituted-3H-1,2,4-triazole-3,5(4H)-dione reagent (1c) is generally known as a bifunctional reagent. Representative examples of suitable bifunctional reagents are depicted below (where X is a spacer).

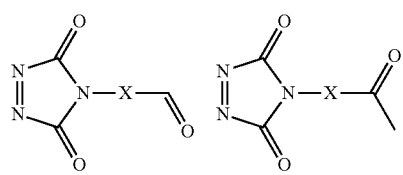

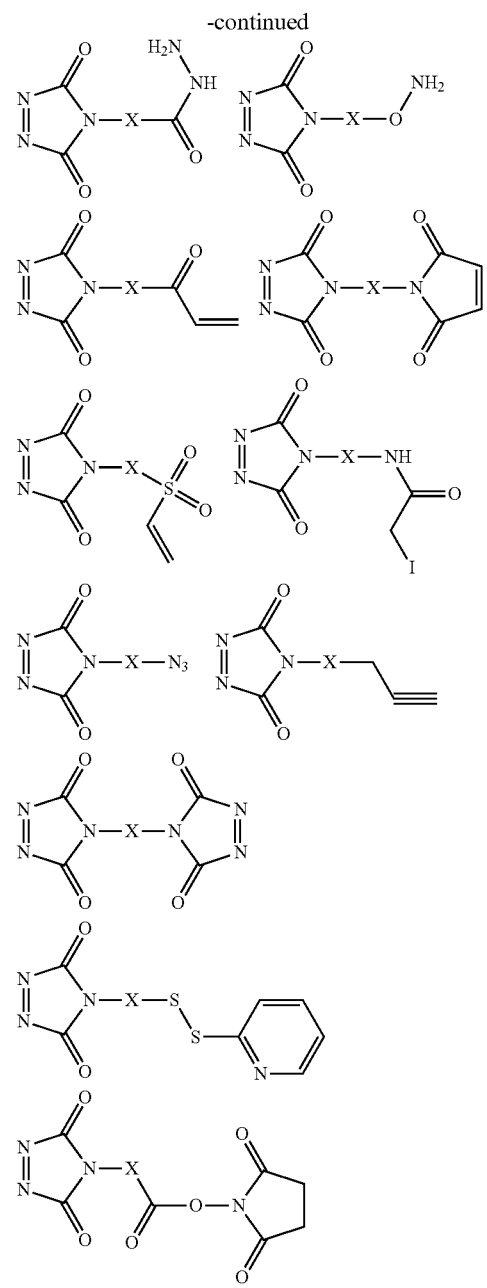

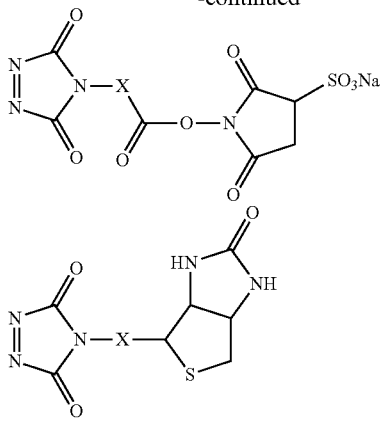

Suitable bifunctional reagents which are either commerically available, readily prepared from known literature preparations, or prepared as described in the Example section below include 4-methyl-3H-1,2,4-triazole-3,5(4H)-dione, (E)-4-(4-(1-(benzyloxyimino)ethyl)-phenyl)-3H-1,2,4-triazole-3,5(4H)-dione, (E)-4-(4-(1-(prop-2-ynyloxyimino)ethyl)phenyl)-3H-1,2,4-triazole-3,5(4H)-dione, 4-(4-(2-(2-(prop-2-ynyloxy)ethoxy)ethoxy)phenyl)-3H-1,2,4-triazole-3,5(4H)-dione, tert-butyl 4-(3,5-dioxo-3H-1,2,4-triazol-4(5H)-yl)butylcarbamate, and N-(4-(3,5-dioxo-1H-1,2,4-triazol-4(5H)-yl)butyl)-2-methoxy(polyethyleneglycol)-acetamide.

Suitable bifunctional reagents can also be prepared from their corresponding 1,2,4-triazolidine-3,5-dione derivatives using procedures well-known to those of skill in the art. Representative examples of 3,5-dione derivatives which are commercially available include 4-(4-acetylphenyl)-1,2,4-triazolidine-3,5-dione, 4,4'-[(methylimino)di-3,1-propanediyl]bis-1,2,4-triazolidine-3,5-dione, 4-(3-azidopropyl)-1,2,4-triazolidine-3,5-dione, 4,4'-[1,3-phenylenebis(methylene)]bis-1,2,4-triazolidine-3,5-dione, 4,4'-(1,12-dodecanediyl)bis-1,2,4-triazolidine-3,5-dione, 4,4'-(methylenedi-4,1-phenylene)bis-1,2,4-triazolidine-3,5-dione, 4,4'-(1,4-cyclohexanediyl)bis-1,2,4-triazolidine-3,5-dione, 4,4'-[1,4-butanediylbis(oxy-3,1-propanediyl)]bis-1,2,4-triazolidine-3,5-dione, 4-[3-[(3,5-dioxo-1,2,4-triazolidin-4-yl)methyl]-3,5,5-trimethylcyclohexyl]-1,2,4-triazolidine-3,5-dione, N,N'-bis[(3,5-dioxo-1,2,4-triazolidin-4-yl)methyl]-urea, 4,4'-(1,2-ethanediyl)bis-1,2,4-triazolidine-3,5-dione, 4,4'-(methylenedi-4,1-cyclohexanediyl)bis-1,2,4-triazolidine-3,5-dione, 4,4'-(iminodi-2,1-ethanediyl)bis-1,2,4-triazolidine-3,5-dione, 4,4'-[(4,6-dimethyl-1,3-phenylene)bis(methylene)]bis-1,2,4-triazolidine-3,5-dione, and 4,4'-(1,6-hexanediyl)bis-1,2,4-triazolidine-3,5-dione.

Various derivatives can be prepared using procedures analogous to those described by B. Saville, in "Bis-(p-3,5-dioxo-1,2,4-triazolin-4-ylphenyl)methane: a highly reactive bifunctional enophile" *J Chem Soc D, Chem Commun*, 635-635 (1971); and Organic Syntheses, Coll. Vol. 6, 936 (1988).

The spacer ("X") can provide the desired length between the two reactive groups and/or a desired functionality. For instance, polyethylene glycol (PEG)-based spacers create hydrophilic reagents having better water solubility. Alternatively, an aliphatic (e.g., alkylene) spacer may be used to introduce hydrophobicity. The spacer may also contain additional reactive sites to provide more design flexibility. For example, introduction of a cleavable moiety that cleaves in vivo or photochemically. Particular chemical moieties within the spacer may also affect the reactivity of the linking groups. For instance, it is known that a maleimide group that has an aromatic ring immediately next to it is less stable to ring opening and loss of activity than a maleimide that has an aliphatic ring adjacent to it. In addition, conjugates destined for use in vivo may have different properties depending on the type of spacer on the associated crosslinker. Some spacers may be immunogenic and cause specific antibody production to occur against them. In other instances, the half-life of a conjugate in vivo may be altered by choice of spacer, especially when using cleavable reagents.

The reactive terminal linking group (Lg) can be used to attach other functional moieties (R, such as a therapeutic drug, cytotoxic agent, radioactive agents (e.g., chelating agents with radioactive metal), haptens, lipids, and polymers (e.g., polyethylene glycols and polysaccharides)). The linking group can be any chemical group that allows coupling of the functional moiety (R) to the spacer (X). Suitable linking groups include halogen, —C≡CH, —C=CH$_2$, —OH, —SH, —SO$_2$—CH=CH$_2$, —O—NH$_2$, —N$_3$, —O—P(O)(OH)$_2$, —C(O)—H, —C(O)—CH$_3$, —NH—C(O)—CH$_2$—I, maleimidyl, 3,5-dioxo-1,2,4-triazolidin-4-yl, 1H-pyrrole-2,5-dione-1-yl, pyridin-2-yl-disulfanyl, tetrahydro-1H-thieno[3,4-d]imidazol-2(3H)-one-4-yl, 1-carbonyloxy-2,5-dioxopyrrolidine, sodium 1-carbonyloxy-2,5-dioxopyrrolidine-3-sulfonate, —SSR$^1$, —C(O)—OR$^1$, —N(R$^1$)H, —NH—N(R$^1$)H, where R$^1$ is H or (C$_1$-C$_6$)alkyl, and —C(O)—R$^2$, where R$^2$ is H, (C$_1$-C$_4$)alkyl, halo-substituted(C$_1$-C$_4$)alkyl, —CH=CH$_2$, N(R$^1$)H, or —NH— N(R$^1$)H. In some embodiments, —NH$_2$ and —CH$_2$Br may be suitable linking groups.

In embodiments when the spacer ("X") contains one or more additional reactive sites, the additional reactive sites may include one or more further terminal active linking groups. Accordingly, the spacer may comprise one or more further terminal active linking groups. For instance, the spacer may comprise a second terminal active linking group (Lg$_2$), in addition to linking group Lg. Alternatively, the spacer may comprise a second terminal active linking group (Lg$_2$) and a third terminal active linking group (Lg$_3$). In another alternative, the spacer may comprise a second terminal active linking group (Lg$_2$), a third terminal active linking group (Lg$_3$) and a fourth terminal active linking group (Lg$_4$). However, the spacer typically comprises only a second terminal active linking group (Lg$_2$), in addition to linking group Lg. Each of the one or more further terminal active linking groups is usually at the terminus of a branch in the spacer.

In embodiments where the spacer comprises one or more further terminal active linking groups, each of these one or more further terminal active linking groups may be independently selected from any chemical group that allows coupling of the functional moiety (R, such as a therapeutic drug, cytotoxic agent, radioactive agents (e.g., chelating agents with radioactive metal), haptens, lipids, and polymers (e.g., polyethylene glycols and polysaccharides)) to the spacer (X). Suitable linking groups include halogen, —C≡CH, —C=CH$_2$, —OH, —SH, —SO$_2$—CH=CH$_2$, —O—NH$_2$, —N$_3$, —O—P(O)(OH)$_2$, —C(O)—H, —C(O)—CH$_3$, —NH—C(O)—CH$_2$—I, maleimidyl, 3,5-dioxo-1,2,4-triazolidin-4-yl, 1H-pyrrole-2,5-dione-1-yl, pyridin-2-yl-disulfanyl, tetrahydro-1H-thieno[3,4-d]imidazol-2(3H)-one-4-yl, 1-carbonyloxy-2,5-dioxopyrrolidine, sodium 1-carbonyloxy-2,5-dioxopyrrolidine-3-sulfonate, —SSR$^1$, —C(O)—OR$^1$, —N(R$^1$)H, —NH—N(R$^1$)H, where R$^1$ is H or (C$_1$-C$_6$) alkyl, and —C(O)—R$^2$, where R$^2$ is H, (C$_1$-C$_4$)alkyl, halo-substituted(C$_1$-C$_4$)alkyl, —CH=CH$_2$, N(R$^1$)H, and —NH— N(R$^1$)H. In these embodiments, the terminal active linking groups (including the one or more further terminal active linking groups) are typically all the same. For example, the inventors have found that spacers wherein all of the terminal active linking groups are —C≡CH are particularly suitable. In these embodiments, the functional moiety R is typically a polysaccharide.

In particular embodiments when the spacer ("X") comprises one or more further terminal active linking groups, the spacer X is typically selected from $(C_1-C_{20})$alkylene, $(C_2-C_{20})$alkenylene, $(C_2-C_{20})$alkynylene, where said $(C_1-C_{20})$alkylene, said $(C_2-C_{20})$alkenylene, and said $(C_2-C_{20})$alkynylene moieties each independently optionally contain 1-10 oxygen atoms interdispersed within said moieties, and wherein said $(C_1-C_{20})$alkylene, $(C_2-C_{20})$alkenylene and $(C_2-C_{20})$alkynylene moieties are branched.

Preferably, the spacer X is a $(C_1-C_{20})$alkylene, where said $(C_1-C_{20})$alkylene contains 1-10 oxygen atoms interdispersed within said moiety and wherein said $(C_1-C_{20})$alkylene is branched. Each of the one or more further terminal active linking groups is usually at the terminus of a branch in the spacer.

When the spacer ("X") comprises one further terminal active linking group, the group —X-Lg in the conjugate of Formula (I-A) can be represented as

where

Y is a spacer selected from the same options as X as defined above and Lg and $Lg_2$ are each linking groups as defined above. Lg, $Lg_2$ and $Lg_3$ (when present) can be the same or different linking groups, and can be attached at any available position on spacer Y.

In one particular embodiment, spacer Y is selected from the group consisting of (a) a bond, —O—, —S—, —NH—, —N(($C_1-C_6$)alkyl)-, —NH—C(O)—NH—, —C(O)—NH—, —NH—C(O)—;

(b) $(C_1-C_{20})$alkylene, $(C_2-C_{20})$alkenylene, $(C_2-C_{20})$alkynylene, —Z—$(C_1-C_{20})$alkylene-, —Z—$(C_2-C_{20})$alkenylene, —Z—$(C_2-C_{20})$alkynylene, $(C_1-C_{20})$alkylene-Z—$(C_1-C_{20})$alkylene, $(C_2-C_{20})$alkenylene-Z—$(C_2-C_{20})$alkenylene, $(C_2-C_{20})$alkynylene-Z—$(C_2-C_{20})$alkynylene, where Z is —NH—, —N(($C_1-C_6$)alkyl)-, —NH—C(O)—NH—, —C(O)—NH—, —NH—C(O)—, $(C_3-C_7)$cycloalkylene, phenylene, heteroarylene, or heterocyclene and where said $(C_1-C_{20})$alkylene, said $(C_2-C_{20})$alkenylene, and said $(C_2-C_{20})$alkynylene moieties each independently optionally contain 1-10 oxygen atoms interdispersed within said moieties;

(c) $(C_3-C_7)$cycloalkylene, $(C_3-C_7)$cycloalkylene-Y—$(C_3-C_7)$cycloalkylene, —Y—$(C_3-C_7)$cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is $(C_1-C_{20})$alkylene, $(C_2-C_{20})$alkenylene, $(C_2-C_{20})$alkynylene, —O—, —C(O)—, —S—, —NH—, —N(($C_1-C_6$)alkyl)-, —NH—C(O)—NH—, —C(O)—NH—, or —NH—C(O)— and where said $(C_3-C_7)$cycloalkylene, said phenylene, said heteroarylene, and said heterocyclene moieties are each individually optionally substituted with 1 to 3 substituents selected from halo, $(C_1-C_4)$alkyl or halo-substituted$(C_1-C_4)$alkyl;

(d) —[$OCH_2CH_2$]$_v$—O—, where v is 1-2,000; and (e) a peptide comprising 1 to 30 amino acids.

Typically, spacer Y is selected from the group consisting of $(C_1-C_{20})$alkylene, $(C_2-C_{20})$alkenylene and $(C_2-C_{20})$alkynylene, where said $(C_1-C_{20})$alkylene, said $(C_2-C_{20})$alkenylene, and said $(C_2-C_{20})$alkynylene moieties each independently optionally contain 1-10 oxygen atoms interdispersed within said moieties, and wherein said $(C_1-C_{20})$alkylene, $(C_2-C_{20})$alkenylene and $(C_2-C_{20})$alkynylene moieties are branched. Preferably, spacer Y is a $(C_1-C_{20})$alkylene, where said $(C_1-C_{20})$alkylene contains 1-10 oxygen atoms interdispersed within said moiety and wherein said $(C_1-C_{20})$alkylene is branched. In these embodiments, each of Lg and $Lg_2$ is usually at the terminus of a branch in the spacer.

Similarly, when the spacer ("X") comprises one further terminal active linking group, the group —X-Lg in the 4-substituted-3H-1,2,4-triazole-3,5(4H)-dione of Formula (I-Ib) can be represented as

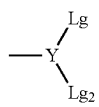

where

Y is a spacer as defined above and Lg and $Lg_2$ are as defined above. Each of Lg and $Lg_2$ is usually at the terminus of a branch in the spacer.

When the spacer ("X") comprises one further terminal active linking group, the group
-L-R in the conjugate of Formula (I) can be represented as

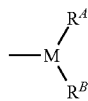

where $R^A$ and $R^B$ are independently selected from the same options as R above and M is a linker comprising a spacer Y', where Y' is selected from the same options as X' as defined above.

Typically, both $R^A$ and $R^B$ are the same. For example, $R^A$ and $R^B$ are both polysaccharides. Each of $R^A$ and $R^B$ is usually at the terminus of a branch in the spacer.

In one particular embodiment, M is a linker comprising a spacer Y' selected from the group consisting of (a) a bond, —O—, —S—, —NH—, —N(($C_1-C_6$)alkyl)-, —NH—C(O)—NH—, —C(O)—NH—, —NH—C(O)—;

(b) $(C_1-C_{20})$alkylene, $(C_2-C_{20})$alkenylene, $(C_2-C_{20})$alkynylene, —Z—$(C_1-C_{20})$alkylene-, —Z—$(C_2-C_{20})$alkenylene, —Z—$(C_2-C_{20})$alkynylene, $(C_1-C_{20})$alkylene-Z—$(C_1-C_{20})$alkylene, $(C_2-C_{20})$alkenylene-Z—$(C_2-C_{20})$alkenylene, $(C_2-C_{20})$alkynylene-Z—$(C_2-C_{20})$alkynylene, where Z is —NH—, —N($C_1-C_6$)alkyly, —NH—C(O)—NH—, —C(O)—NH—, —NH—C(O)—, $(C_3-C_7)$cycloalkylene, phenylene, heteroarylene, or heterocyclene and where said $(C_1-C_{20})$alkylene, said $(C_2-C_{20})$alkenylene, and said $(C_2-C_{20})$alkynylene moieties each independently optionally contain 1-10 oxygen atoms interdispersed within said moieties;

(c) $(C_3-C_7)$cycloalkylene, $(C_3-C_7)$cycloalkylene-Y—$(C_3-C_7)$cycloalkylene, —Y—$(C_3-C_7)$cycloalkylene, phenylene, —Y-phenylene, phenylene-Y-phenylene, heteroarylene, Y-heteroarylene, heteroarylene-Y-heteroarylene, heterocyclene, —Y-heterocyclene, or heterocyclene-Y-heterocyclene, where Y is $(C_1-C_{20})$alkylene, $(C_2-C_{20})$alkenylene, $(C_2-C_{20})$ alkynylene, —O—, —C(O)—, —S—, —NH—, —N(($C_1$-$C_6$)alkyl)-, —NH—C(O)—NH—, —C(O)—NH—, or —NH—C(O)— and where said $(C_3-C_7)$cycloalkylene, said phenylene, said heteroarylene, and said heterocyclene moieties are each individually optionally substituted with 1 to 3 substituents selected from halo, $(C_1-C_4)$alkyl or halo-substituted$(C_1-C_4)$alkyl;

(d) —[OCH$_2$CH$_2$]$_v$—O—, where v is 1-2,000; and (e) a peptide comprising 1 to 30 amino acids.

In one embodiment M is a linker comprising a spacer Y' selected from the group consisting of $(C_1-C_{20})$alkylene, $(C_2-C_{20})$alkenylene and $(C_2-C_{20})$alkynylene, where said $(C_1-C_{20})$ alkylene, said $(C_2-C_{20})$alkenylene, and said $(C_2-C_{20})$alkynylene moieties each independently optionally contain 1-10 oxygen atoms interdispersed within said moieties, and wherein said $(C_1-C_{20})$alkylene, $(C_2-C_{20})$alkenylene and $(C_2-C_{20})$alkynylene moieties are branched. Preferably, the spacer Y' is a $(C_1-C_{20})$alkylene, where said $(C_1-C_{20})$alkylene contains 1-10 oxygen atoms interdispersed within said moiety and wherein said $(C_1-C_{20})$alkylene is branched. In these embodiments, each of $R^A$ and $R^B$ is usually at the terminus of a branch in the spacer.

Similarly, when the spacer ("X") comprises one further terminal active linking group, the group -L-R in the 4-substituted-3H-1,2,4-triazole-3,5(4H)-dione of Formula (Ib) can be represented as

where $R^A$ and $R^B$ are as defined above M is a linker comprising a spacer Y' as defined above.

Typically, both $R^A$ and $R^B$ are the same. Preferably, $R^A$ and $R^B$ are both polysaccharides. Each of $R^A$ and $R^B$ is usually at the terminus of a branch in the spacer.

In embodiments where the spacer comprises one further terminal active linking group, the 4-substituted-3H-1,2,4-triazole-3,5(4H)-dione reagent (1c) may also be a trifunctional reagent. Representative examples of suitable trifunctional reagents are depicted below:

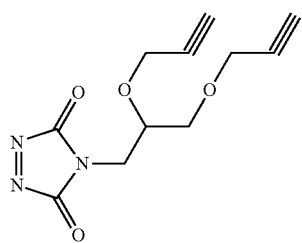

-continued

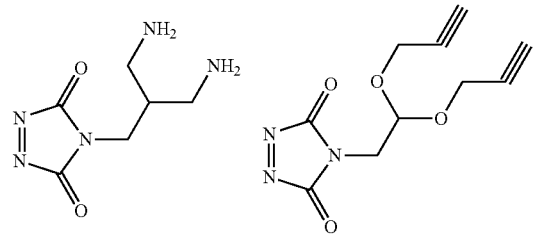

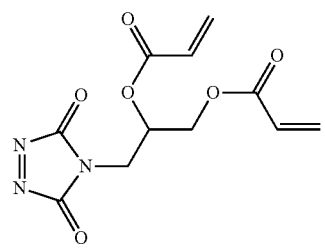

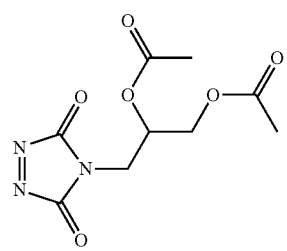

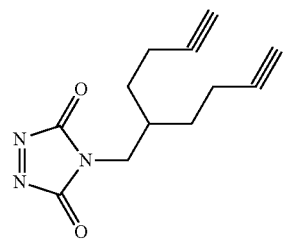

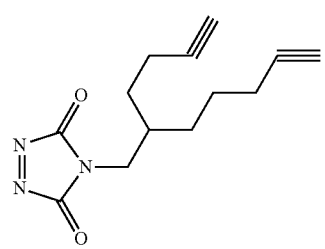

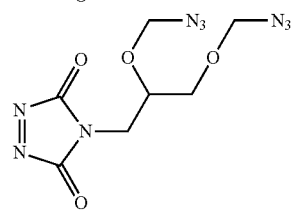

In one preferred embodiment, the conjugate of Formula (I) has the following structure:

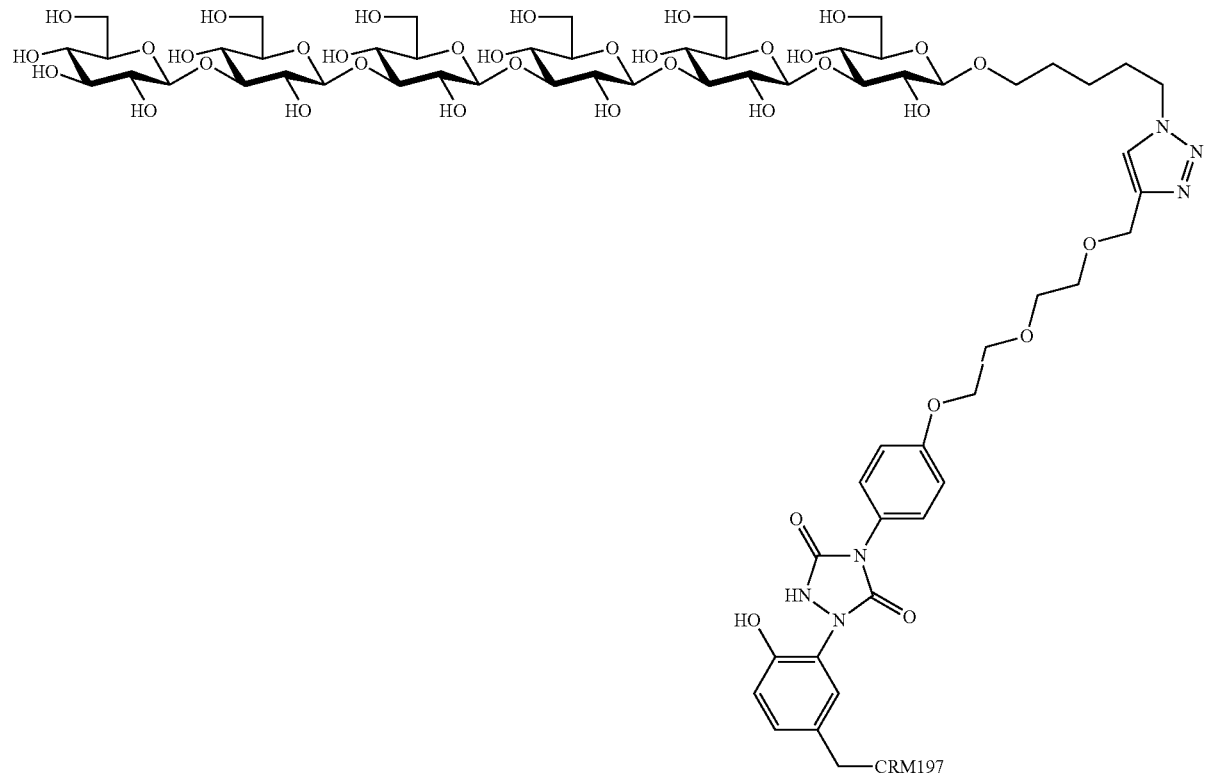

In another preferred embodiment, the conjugate of Formula (I) has the following structure:

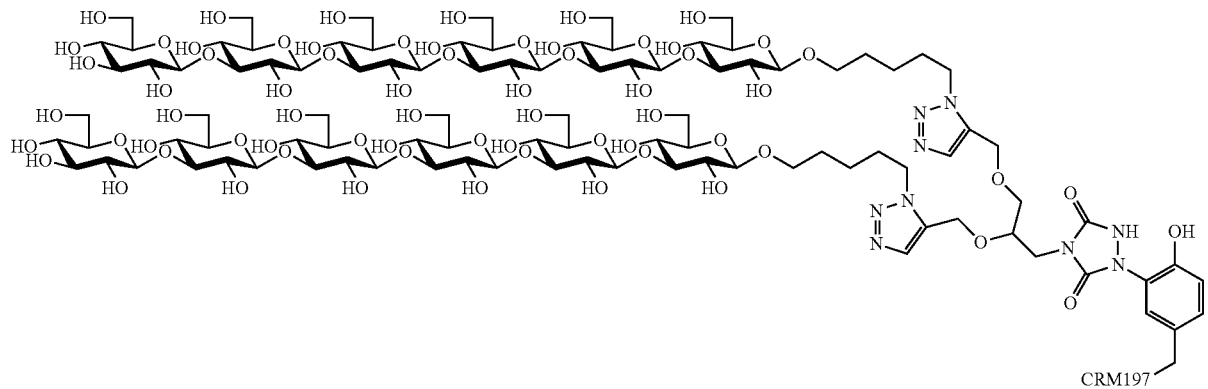

In some embodiments, CRM197 may instead be an antibody or a vaccine carrier protein other than CRM197.

Therapeutic Agents: "Therapeutic agent" refers to any compound that is used in the detection, diagnosis or treatment of human disease. Such compounds may be naturally-occurring, modified or synthetic. Therapeutic agents may promote or inhibit any biological process implicated in a human disease pathway when administered in a therapeutically effective amount. The phrase "therapeutically effective amount" means an amount of a compound that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species.

Cytotoxic agents: "Cytotoxic agent" refers to any naturally-occurring, modified or synthetic compound that is toxic to tumor cells. Such agents are useful in the treatment of neoplasms, as well as inflammatory disease, autoimmune disorders and in the treatment of other symptoms or disease characterized by cell proliferation or a hyperactive cell population. Cytotoxic agents include alkylating agents, antibiotics, antimetabolites, tublin inhibitors, topoisomeriase I and II inhibitors, hormonal agonists or antagonists, or immunomodulators, Cytotoxic agents may be cytotoxic when activated by light or infrared, may operate through other mechanistic pathways, or be supplementary potentiating agents. Suitable cytotoxic agents include, for example, maytansinoids, doxorubicin, calicheamicin, adozelesin, C-10 methyldisulfanylpropanoyl taxoid, camptothecin, homocamptothecin, colchicine, combretastatin, dolistatin, methotrexate, podophyllotoxin, rhizoxin, rhizoxin D, taxol, and paclitaxol. Lipids: Suitable lipids include, e.g., natural lipids, sphingolipids, phospholipids, sterols (e.g., cholesterol), bioactive lipids, coenzyme A (and its derivatives), fatty acid modified lipids, headgroup modified lipids, radiolabeled lipids, fluorescent lipids (such as N-(7-nitro-2-oxa-1,3-diazol-4-yl)dioleoylphosphatidylethanolamine and N-(lissamine rhodamine B sulfonyl)-dipalmitoylphosphatidylethanolamine), cationic lipids (such as those described by Pal, et al., in *J Med Chem* 54, 2378-2390 (2011)) and polymeric lipids. Suitable lipids can also be purchased from Avanti Polar Lipids (Birmingham, Ala.) or Northern Lipids (Vancouver, BC, Canada).
Polymers: Suitable polymers include polyethyleneglycols (PEGs) having a weight average molecular weight up to about 40 kDa, The PEG can be linear or branched. Purified PEG is most commonly available commercially as mixtures of different oligomer sizes in broadly or narrowly defined molecular weight (MW) ranges. For example, "PEG 600" typically denotes a preparation that includes a mixture of oligomers having an average molecular weight of 600 g/mol (or 600 Da). Likewise, "PEG 10000" denotes a mixture of PEG molecules (H—[O—CH2CH2]v-OH, where v=195-265) having an average molecular weight of 10,000 g/mol (or 10 kDa). For a 20 kDa PEG, v=420-510. Numerous PEG's and PEG derivatives are available from Thermo Fisher Scientific (Rockford, Ill.) and Jenkem Technology (Allen, Tex.). Other suitable polymers include polysaccharides, polyalkylene glycols, polyvinylpyrrolidones, polyacrylates, polymethacrylates, polyoxazolines, polyvinylalcohols, polyacrylamides, polymethacrylamides, HPMA copolymers, polyesters, polyacetals, poly(ortho ester)s, polycarbonates, poly(imino carbonate)s, copolymers of divinylether-maleic anhydride or styrene-maleic anhydride, or polyglutamic acids.

The polysaccharide may be any polysaccharide, particularly a polysaccharide from a pathogenic organism. Conjugates of these polysaccharides may be useful for immunizing a subject against infection caused by the pathogenic organism. Exemplary polysaccharides for use in the invention are described below. In particular, the polysaccharide may be a bacterial polysaccharide, e.g. a bacterial capsular polysaccharide. Representative bacterial polysaccharides are described in Table 1:

TABLE 1

| Polysaccharide | Repeat Unit |
|---|---|
| *Haemophilus influenzae* Type b ('PRP') | →3)-β-D-Ribf-(I→1)-D-Ribitol-(5→OPO$_3$→ |
| *Neisseria meningitides* | |
| Group A | →6)-α-D-ManpNAc(3OAc)-(I→OPO$_3$→ |
| Group C | →9)-α-D-Neu5Ac(7/8OAc)-(2→ |
| Group W135 | →6)-α-D-Galp-(I→4)-α-D-Neu5Ac(9OAc)-2→ |
| Group Y | →6)-α-D-Glcp-(I→4)-α-D-Neu5Ac(9OAc)-2→ |
| *Salmonella enterica* Typhi Vi | →-α-D-GalpNAcA(3OAc)-(I→ |
| *Streptococcus pneumoniae* | |
| Type 1 | →3)-D-AAT-α-Galp-(I→4)-α-D-GalpA(2/3OAc)-(I→3)-α-D-GalpA-(I→ |
| Type 2 | →4-β-D-Glcp-(I→3)-[α-D-GlcpA-(I→6)-α-D-Glcp-(I→2)]-α-L-Rhap-(I→3)-α-L-Rhap-(I→3)-3-L-Rhap-(I→ |
| Type 3 | →3)-β-D-GlcA-(I→4)-3-D-Glcp-(I→ |
| Type 4 | →3β-D-ManpNAc-(I→3)-α-L-FucpNAc-(I→3)-α-D-GalpNAc-(I→4)-α-D-Galp2,3(S)Py-(I→ |
| Type 5 | →4)-β-D-Glcp-(I→4)-[α-L-PnepNAc-(I→2)-β-D-GlcpA-(I→3)]-α-L-FucpNAc-(I→3)-β-D-Sugp-(I→ |
| Type 6B | →2)-α-D-Galp-(I→3)-α-D-Glcp-(I→3)-α-L-Rhap-(I→4)-D-Rib-ol-(5→P→ |
| Type 9N | →4)-α-D-GlcpA-(I→3)-α-D-Glcp-(I→3)-β-D-ManpNAc-(I→4)-β-D-Glcp-(I→4)-α-D-GlcpNAc-(I→ |
| Type 14 | →4)-β-D-Glcp-(I→6)-[β-D-Galp-(I→4)]-β-D-GlcpNAc-(I→3)-β-D-Galp-(I→ |
| Type 18C | →4)-β-D-Glcp-(I→4)-[α-D-Glcp(6OAc)-(I→2)][Gro-(I→P→3)]-β-D-Galp-(I→4)-α-D-Glcp-(I→3)-β-L-Rhap-(I→ |
| Type 19A | →4)-β-D-ManpNAc-(I→4)-α-D-Glcp-(I→3)-α-L-Rhap-(I→P→ |
| Type 19F | →4)-β-ManpNAc-(I→4)-α-D-Glcp-(I→2)-α-L-Rhap-(I→P→ |
| Type 23F | →4)-β-D-Glcp-(I→4)-[α-L-Rhap-(I→2)]-[Gro-(2→P→3)]-β-D-Galp-(I→4)-β-L-Rhap-(I→ |
| *Staphylococcus aureus* | |
| Type 5 | →4)-β-D-ManNAcA(3OAc)-(I→4)-α-L-FucNAc-(I→3)-β-D-FucNAc-(I→ |
| Type 8 | →4)-β-D-ManNAcA(4OAc)-(I→3)-α-L-FucNAc-(I→3)-β-D-FucNAc-(I→ |

AAT is 2-acetamido-4-amino-2,4,6-trideoxygalactose, Gro is glycerol, Pne is 2-acetamido-2,6-2,6-dideoxytalose and P is phosphate in a phosphodiester linkage.

The polysaccharides may be used in the form of oligosaccharides. These are conveniently formed by fragmentation of purified polysaccharide (e.g. by hydrolysis), which will usually be followed by purification of the fragments of the desired size. Polysaccharides may be purified from natural sources. As an alternative to purification, polysaccharides may be obtained by total or partial synthesis.

*N. meningitidis* Capsular Polysaccharides: The polysaccharide may be a bacterial capsular polysaccharide. Exemplary bacterial capsular polysaccharides include those from *N. meningitides*. Based on the organism's capsular polysaccharide, various serogroups of *N. meningitidis* have been identified, including A, B, C, H, I, K, L, 29E, W135, X, Y & Z. The polysaccharide in the invention may be from any of these serogroups. Typically, the polysaccharide is from one of the following meningococcal serogroups: A, C, W135 and Y. The capsular polysaccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is typically performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays (Ravenscroft et al. *Vaccine* 17, 2802-2816 (1999)).

If hydrolysis is performed, the hydrolysate will generally be sized in order to remove short-length oligosaccharides (Costantino et al. *Vaccine* 17, 1251-1263 (1999)). This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Chemical hydrolysis of saccharides generally involves treatment with either acid or base under conditions that are standard in the art. Conditions for depolymerisation of capsular polysaccharides to their constituent monosaccharides are known in the art. One depolymerisation method involves the use of hydrogen peroxide (WO02/058737). Hydrogen peroxide is added to a saccharide (e.g. to give a final $H_2O_2$ concentration of 1%), and the mixture is then incubated (e.g. at around 55° C.) until a desired chain length reduction has been achieved. The reduction over time can be followed by removing samples from the mixture and then measuring the (average) molecular size of saccharide in the sample. Depolymerization can then be stopped by rapid cooling once a desired chain length has been reached Serogroups C, W135 and Y: Techniques for preparing capsular polysaccharides from meningococci have been known for many years, and typically involve a process comprising the steps of polysaccharide precipitation (e.g. using a cationic detergent), ethanol fractionation, cold phenol extraction (to remove protein) and ultracentrifugation (to remove LPS) (for example, see Frash, *Advances in Biotechnological Processes* 13, 123-145 (1990) (eds. Mizrahi & Van Wezel).

A more preferred process (WO03/007985) involves polysaccharide precipitation followed by solubilisation of the precipitated polysaccharide using a lower alcohol.

Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred (Inzana, *Infect. Immun.* 55, 1573-1579 (1987). Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol may be added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

As an alternative to purification, capsular polysaccharides of the present invention may be obtained by total or partial synthesis e.g. Hib synthesis is disclosed in Kandil et al. *Glycoconi J* 14, 13-17. (1997), and MenA synthesis in Berkin et al. *Chemistry* 8, 4424-4433 (2002).

The polysaccharide may be chemically modified e.g. it may be O-acetylated or de-O-acetylated. Any such de-O-acetylation or hyper-acetylation may be at specific positions in the polysaccharide. For instance, most serogroup C strains have O-acetyl groups at position C-7 and/or C-8 of the sialic acid residues, but about 15% of clinical isolates lack these O-acetyl groups (Glode et al. *J Infect Dis* 139, 52-56 (1979); WO94/05325; U.S. Pat. No. 5,425,946). The acetylation does not seem to affect protective efficacy (e.g. unlike the Menjugate™ product, the NeisVac-C™ product uses a de-O-acetylated polysaccharide, but both vaccines are effective). The serogroup W135 polysaccharide is a polymer of sialic acid-galactose disaccharide units. The serogroup Y polysaccharide is similar to the serogroup W135 polysaccharide, except that the disaccharide repeating unit includes glucose instead of galactose. Like the serogroup C polysaccharides, the MenW135 and MenY polysaccharides have variable O-acetylation, but at sialic acid 7 and 9 positions (WO2005/033148). Any such chemical modifications preferably take place before conjugation, but may alternatively or additionally take place during conjugation.

Polysaccharides from different serogroups are preferably purified separately, and may then be combined, either before or after conjugation.

Serogroup A: The polysaccharide may be from a serogroup A. The polysaccharide can be purified in the same way as for serogroups C, W135 and Y (see above), although it is structurally different—whereas the capsules of serogroups C, W135 and Y are based around sialic acid (N-acetyl-neuraminic acid, NeuAc), the capsule of serogroup A is based on N-acetyl-mannosamine, which is the natural precursor of sialic acid. The serogroup A polysaccharide is particularly susceptible to hydrolysis, and its instability in aqueous media means that (a) the immunogenicity of liquid vaccines against serogroup A declines over time, and (b) quality control is more difficult, due to release of saccharide hydrolysis products into the vaccine.

Native MenA capsular polysaccharide is a homopolymer of ($\alpha 1 \rightarrow 6$)-linked N-acetyl-D-mannosamine-1-phosphate, with partial O-acetylation at C3 and C4. The principal glycosidic bond is a 1-6 phosphodiester bond involving the hemiacetal group of C1 and the alcohol group of C6 of the D-mannosamine. The average chain length is 93 monomers. It has the following formula:

$R^z$ = Ac, $R^q$ = H : 70%
$R^z$ = H, $R^q$ = H : 23%
$R^z$ = H, $R^q$ = Ac : 7%

A modified polysaccharide has been prepared which retains the immunogenic activity of the native serogroup A polysaccharide but which is much more stable in water. Hydroxyl groups attached at carbons 3 and 4 of the monosaccharide units are replaced by a blocking group (WO03/080678 & WO2008/084411).

The number of monosaccharide units having blocking groups in place of hydroxyls can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on any particular monosaccharide unit may be 1 or 2.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$alkyl), CN, $CF_3$, $CCl_3$, etc.

Typical blocking groups are of the formula: —O—X'—Y' and —$OR^3$ wherein: X' is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2(C_{1-6}$alkyl), CN, $CF_3$ or $CCl_3$; or Y' is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^3$ can be prepared from —OH groups by standard derivatizing procedures, such as reaction of the hydroxyl group with an acyl halide, alkyl halide, sulfonyl halide, etc. Hence, the oxygen atom in —O—X—Y is usually the oxygen atom of the hydroxyl group, while the —X—Y group in —O—X—Y usually replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

Specific blocking groups for use in the invention are —OC(O)$CF_3$ (Nilsson & Svensson *Carbohydrate Research* 69, 292-296 (1979)) and a carbamate group OC(O)$NR^1R^2$, where $R^1$ and $R^2$ are independently selected from $C_{1-6}$ alkyl. Typically, R1 and R2 are both methyl i.e. the blocking group is —OC(O)$NMe_2$. Carbamate blocking groups have a stabilizing effect on the glycosidic bond and may be prepared under mild conditions.

A particularly preferred blocking group is —OC(O)$CH_3$ (WO2008/084411). The proportion of 4- and/or 3-positions in the modified *Neisseria meningitidis* serogroup A polysaccharide that have this blocking group may vary. For example, the proportion of 4-positions that have blocking groups may be about 0%, at least 10%, 20%, 30%, 40%, 50%, 60%, 70%, 80%, 90%, 95% or about 100%, with at least 80% and about 100% being preferred. Similarly, the proportion of 3-positions that have blocking groups may be about 0%, at least 10%, 20%, 30%, 40%, 50%, 60%, 70%, 80%, 90%, 95% or about 100%, with at least 80% and about 100% being preferred. Typically, the proportion of 4- and 3-positions that have blocking groups is about the same at each position. In other words, the ratio of 4-positions that have blocking groups to 3-positions that have blocking groups is about 1:1. However, in some embodiments, the proportion of 4-positions that have blocking groups may vary relative to the proportion of 3-positions that have blocking groups. For example, the ratio of 4-positions that have blocking groups to 3-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2. Similarly, the ratio of 3-positions that have blocking groups to 4-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2.

Typical modified MenA polysaccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is usually 50 or more. The absent —OH groups are blocking groups as defined above.

Other typical modified MenA polysaccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are blocking groups as defined above.

Suitable modified MenA polysaccharides for use with the invention have the formula:

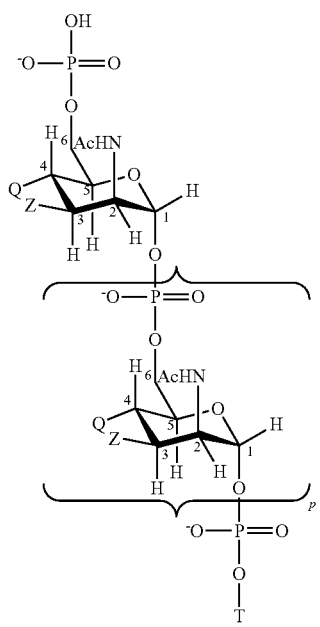

wherein:

p is an integer from 1 to 100 (particularly an integer from 5 to 25, usually 15-25);

T is of the formula (A) or (B):

(A)

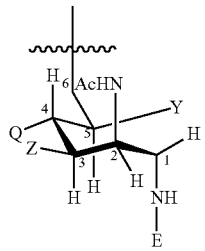

(B)

each Z group is independently selected from OH or a blocking group as defined above; and each Q group is independently selected from OH or a blocking group as defined above;

Y is selected from OH or a blocking group as defined above;

E is H or a nitrogen protecting group;

and wherein more than about 7% (e.g. 8%, 9%, 10% or more) of the Q groups are blocking groups. In some embodiments, the hydroxyl group attached at carbon 1 in formula (A) is replaced by a blocking group as defined above. In some embodiments, E in formula (B) is a linker or a carrier molecule as discussed below. When E is a linker, the linker may be covalently bonded to a carrier molecule.

Each of the p+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Typically, about 70% of the Z groups are OAc, with the remainder of the Z groups being OH or blocking groups as defined above. At least about 7% of Q groups are blocking groups. Typically, at least 10%, 20%, 30%, 40%, 50%, 60%, 70%, 80%, 90% or even 100% of the Q groups are blocking groups.

Glucans: The polysaccharide may be a glucan. Glucans are glucose-containing polysaccharides found inter alia in fungal cell walls. The α-glucans include one or more α-linkages between glucose subunits, whereas β-glucans include one or more β-linkages between glucose subunits. The glucan used in accordance with the invention includes β linkages, and may contain only β linkages (i.e. no α linkages).

The glucan may comprise one or more β-1,3-linkages and/or one or more β-1,6-linkages. It may also comprise one or more β-1,2-linkages and/or β-1,4-linkages, but normally its only β linkages will be β-1,3-linkages and/or β-1,6-linkages. The glucan may be branched or linear.

Full-length native β-glucans are insoluble and have a weight average molecular weight in the megadalton range. It is preferred to use soluble glucans in conjugates of the invention. Solubilisation may be achieved by fragmenting long insoluble glucans. This may be achieved by hydrolysis or, more conveniently, by digestion with a glucanase (e.g. with a β-1,3-glucanase or a β-1,6-glucanase). As an alternative, short glucans can be prepared synthetically by joining monosaccharide building blocks.

Low molecular weight glucans are preferred, particularly those with a weight average molecular weight of less than 100 kDa (e.g. less than 80, 70, 60, 50, 40, 30, 25, 20, or 15 kDa). It is also possible to use oligosaccharides e.g. containing 60 or fewer (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units. Within this range, oligosaccharides with between 10 and 50 or between 20 and 40 monosaccharide units are preferred.

The glucan may be a fungal glucan. A 'fungal glucan' will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis*, *Trichophyton verrucosum*, *Blastomyces dermatidis*, *Cryptococcus neoformans*, *Histoplasma capsulatum*, *Saccharomyces cerevisiae*, *Paracoccidioides brasiliensis*, or *Pythiumn insidiosum*.

There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. Tokunaka et al. *Carbohydr Res* 316, 161-172. (1999), for instance, discloses a two-step procedure for preparing a water-soluble β-glucan extract from *Candida*, free from cell-wall mannan, involving NaClO oxidation and DMSO extraction. The resulting product ('*Candida* soluble β-D-glucan' or 'CSBG') is mainly composed of a linear β-1,3-glucan with a linear β-1,6-glucan moiety. Similarly, WO03/097091 discloses the production of GG-zym from Calbicans. Such glucans from *C. albicans*, include (a) β-1,6-glucans with 3-1,3-glucan lateral chains and an average degree of polymerisation of about 30, and (b) β-1,3-glucans with β-1,6-glucan lateral chains and an average degree of polymerisation of about 4.

In some embodiments of the invention, the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia bicyclis* laminarin, but as high as 7:1 in *Laminaria digititata* laminarin (Pang et al. *Biosci Biotechnol Biochem* 69, 553-8 (2005)). Thus the glucan used with the invention may have a β(1-3):β(1-6) ratio of between 1.5:1 and 7.5:1 e.g. about 2:1, 3:1, 4:1, 5:1, 6:1 or 7:1. Optionally, the glucan may have a terminal mannitol subunit, e.g. a 1,1-α-linked mannitol residue (Read et al. *Carbohydr Res.* 281, 187-201 (1996). The glucan may also comprise mannose subunits.

In other embodiments, the glucan has exclusively or mainly β-1,3 linkages, as seen in curdlan. These glucans may elicit better protection than glucans comprising other linkages, particularly glucans comprising β-1,3 linkages and a greater proportion of β-1,6 linkages. Thus the glucan may be made solely of β-1,3-linked glucose residues (e.g. linear β-D-glucopyranoses with exclusively 1,3 linkages). Optionally, though, the glucan may include monosaccharide residues that are not β-1,3-linked glucose residues e.g. it may include β-1,6-linked glucose residues. The ratio of β-1,3-linked glucose residues to these other residues should be at least 8:1 (e.g. >9:1, >10:1, >11:1, >12:1, >13:1, >14:1, >15:1, >16:1, >17:1, >18:1, >19:1, >20:1, >25:1, >30:1, >35:1, >40:1, >45: 1, >50:1, >75:1, >100:1, etc.) and/or there are one or more (e.g. >1, >2, >3, >4, >5, >6, >7, >8, >9, >10, >11, >12, etc.) sequences of at least five (e.g. >5, >6, >7, >8, >9, >10, >11, >12, >13, >14, >15, >16, >17, >18, >19, >20, >30, >40, >50, >60, etc.) adjacent non-terminal residues linked to other residues only by β-1,3 linkages. By "non-terminal" it is meant that the residue is not present at a free end of the glucan. In some embodiments, the adjacent non-terminal residues may not include any residues coupled to a carrier molecule or linker. The presence of five adjacent non-terminal residues linked to other residues only by β-1,3 linkages may provide a protective antibody response, e.g. against *C. albicans*.

In further embodiments, a conjugate may include two different glucans e.g. a first glucan having a β(1-3):β(1-6) ratio of between 1.5:1 and 7.5:1, and a second glucan having exclusively or mainly β-1,3 linkages. For instance a conjugate may include both a laminarin glucan and a curdlan glucan.

Where a β-glucan includes both β-1,3 and β-1,6 linkages at a desired ratio and/or sequence then this glucan may be found in nature (e.g. a laminarin), or it may be made artificially. For instance, it may be made by chemical synthesis, in whole or in part. Methods for the chemical synthesis of β-1,3/β-1,6 glucans are known, for example from Takeo and Tei *Carbohydr Res.* 145, 293-306 (1986), Tanaka et al. *Tetrahedron Letters* 44, 3053-3057 (2003), Ning et al. *Tetrahedron Letters* 43, 5545-5549 (2002), Geurtsen et al. *Journal of Organic Chemistry* 64 (21):7828-7835 (1999), Wu et al. *Carbohydr Res.* 338, 2203-12 (2003), Nicolaou et al. *J. Am. Chem. Soc.* 119, 449-450 (1997), Yamada et al. *Tetrahedron Letters* 40, 4581-4584 (1999), Yamago et al. *Org. Lett.* 24, 3867-3870 (2001), Yuguo et al. *Tetrahedron* 60, 6345-6351 (2004), Amaya et al. *Tetrahedron Letters* 42:9191-9194 (2001), Mei et al. *Carbohydr Res.* 340, 2345-2351 (2005). β-glucan including both β-1,3 and β-1,6 linkages at a desired ratio may also be made starting from an available glucan and treating it with a β-1,6-glucanase (also known as glucan endo-1,6-β-glucosidase, 1,6-β-D-glucan glucanohydrolase, etc.; EC 3.2.1.75) or a β-1,3-glucanase (such as an exo-1,3-glucanase (EC 3.2.1.58) or an endo-1,3-glucanase (EC 3.2.1.39) until a desired ratio and/or sequence is reached.

When a glucan containing solely β-1,3-linked glucose is desired then β-1,6-glucanase treatment may be pursued to completion, as β-1,6-glucanase will eventually yield pure β-1,3 glucan. More conveniently, however, a pure β-1,3-glucan may be used. These may be made synthetically, by chemical and/or enzymatic synthesis e.g. using a (1→3)-β-D-glucan synthase, of which several are known from many organisms (including bacteria, yeasts, plants and fungi). Methods for the chemical synthesis of β-1,3 glucans are known, for example from Takeo et al. *Carbohydr Res.* 245, 81-96 (1993), Jamois et al. Glycobiology 15(4), 393-407 (2005), Lefeber et al. *Chem. Eur. J.* 7(20):4411-4421 (2001) and Huang et al. *Carbohydr Res.* 340, 603-608 (2005). As a useful alternative to synthesis, a natural β-1,3-glucan may be used, such as a curdlan (linear β-1,3-glucan from an *Agrobacterium* previously known as *Alcaligenes faecalis* var. *myxogenes*; commercially available e.g. from Sigma-Aldrich catalog C7821) or paramylon (β-1,3-glucan from *Euglena*). Organisms producing high levels of β-1,3-glucans are known in the art e.g. the *Agrobacterium* of U.S. Pat. No. 5,508,191 or MiKyoung et al. *Biochemical Engineering Journal*, 16, 163-8 (2003), or the *Euglena gracilis* of Barsanti et al. *J Appl Phycol* 13, 59-65 (2001).

Laminarin and curdlan are typically found in nature as high molecular weight polymers e.g. with a weight average molecular weight of at least 100 kDa. They are often insoluble in aqueous media. In their natural forms, therefore, they are not well suited to immunisation. Thus the invention may use a shorter glucan e.g. those containing 60 or fewer glucose monosaccharide units (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose residues in the range of 2-60 may be used e.g. between 10-50 or between 20-40 glucose units. A glucan with 25-30 glucose residues is particularly useful. Suitable glucans may be formed e.g. by acid hydrolysis of a natural glucan, or by enzymatic digestion e.g. with a glucanase, such as a β-1,3-glucanase. A glucan with 11-19, e.g. 13-19 and particularly 15 or 17, glucose monosaccharide units is also useful. In particular, glucans with the following structures (A) or (B) are specifically envisaged for use in the present invention:

(A)

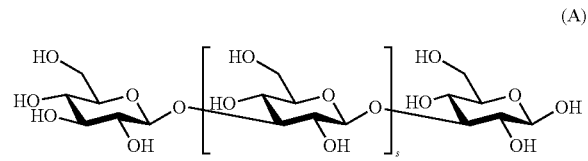

wherein s+2 is in the range of 2-60, e.g. between 10-50 or between 2-40.
Preferably, s+2 is in the range of 25-30 or 11-19, e.g. 13-17. In particular, s+2=15 is suitable. In addition, s+2=6 is suitable.

Vaccine 26, 2284-96 (2008). Suitable glucans for use in this embodiment of the invention have a polydispersity of about 1, e.g. 1.01 or less.

Solubility of natural glucans, such as curdlan, can be increased by introducing ionic groups (e.g. by sulfation, particularly at O-6 in curdlan). Such modifications may be used with the invention, but are ideally avoided as they may alter the glucan's antigenicity.

When the polysaccharide is a glucan, it is typically a laminarin.

S. pneumoniae capsular polysaccharides: As discussed above, the polysaccharide may also be a bacterial capsular polysaccharide. Further exemplary bacterial capsular polysaccharides include those from S. pneumoniae.

When the polysaccharide is a capsular polysaccharide from S. pneumoniae, it is typically from one of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and (B)

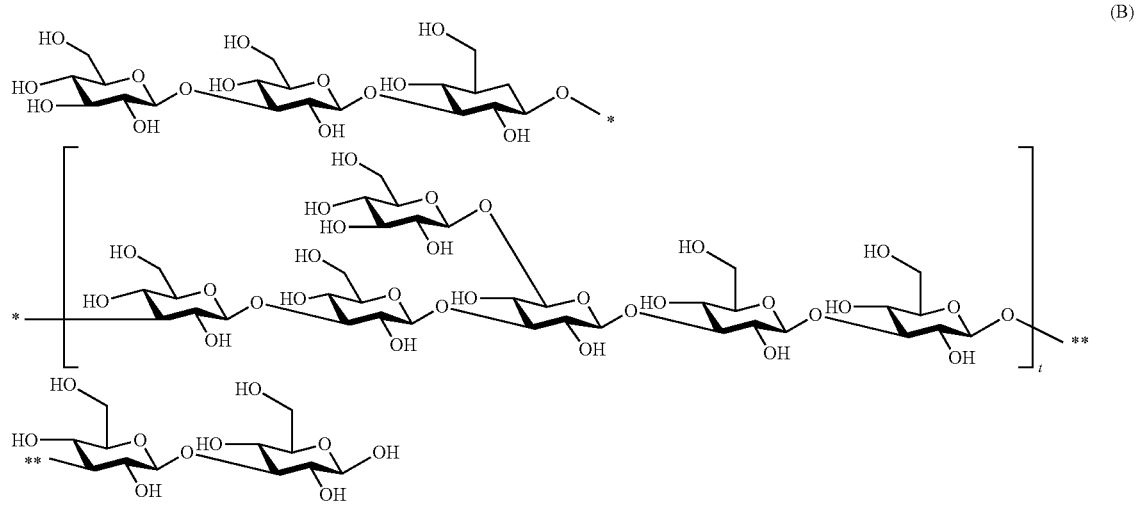

wherein t is in the range of 0-9, e.g. between 1-7 or between 2-6. Preferably, t is in the range of 3-4 or 1-3. In particular, t=2 is suitable. The * and ** indicate the respective attachment points of the polysaccharide units.

In some preferred embodiments, the glucan contains between 5 to 7 glucose monosaccharide units (i.e. 5, 6 or 7). In particular, a glucan having 6 glucose monosaccharide units may be preferred. For example, the glucan may be a curdlan having 6 glucose monosaccharide units.

In some embodiments, the glucan is a single molecular species. In these embodiments, all of the glucan molecules are identical in terms of sequence. Accordingly, all of the glucan molecules are identical in terms of their structural properties, including molecular weight etc. Typically, this form of glucan is obtained by chemical synthesis, e.g. using the methods described above. Alternatively, in other embodiments, the glucan may be obtained from a natural glucan, e.g. a glucan from L. digitata, Agrobacterium or Euglena as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in Bardotti et al.

33F, preferably from 1, 5, 6B, 14, 19F and 23F. Capsular polysaccharides from S. pneumoniae comprise repeating oligosaccharide units which may contain up to 8 sugar residues. The oligosaccharide units for the main S. pneumoniae serotypes are described in the table above, Jones An. Acad. Bras. Cienc, 77(2), 293-324 (2005) and Jones, J Pharm Biomed Anal 38, 840-850 (2005).

S. agialactiae capsular polysaccharides: Further exemplary bacterial capsular polysaccharides include those from Streptococcus agalactiae ("GBS"). The capsular polysaccharide is covalently linked to the peptidoglycan backbone of GBS, and is distinct from the group B antigen, which is another polysaccharide that is attached to the peptidoglycan backbone.

The GBS capsular polysaccharides are chemically related, but are antigenically very different. All GBS capsular polysaccharides share the following trisaccharide core:

β-D-GlcpNAc(1→3)β-D-Galp(1→4)β-D-Glcp

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [α-D-NeupNAc(2→3) β-D-Galp-(1→]disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 85% being caused by five serotypes: Ia, Ib, III & V. The invention may use a polysaccharide from one of these four serotypes. The capsular polysaccharides of each of these four serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All four polysaccharides include galactose residues within the trisaccharide core, but serotypes Ia, Ib, II & III also contain additional galactose residues in each repeating unit. Polysaccharides used according to the invention may be in their native form, or may have been modified. For example, the polysaccharide may be shorter than the native capsular polysaccharide, or may be chemically modified. In particular, the serotype V capsular polysaccharide used in the invention may be modified as described in WO2006/050341 and Guttormsen et al. *Proc Nati Acad Sci USA*. 105(15), 5903-8 (2008) Epub 2008 Mar. 31. For example, a serotype V capsular polysaccharide that has been substantially desialylated. Desialylated GBS serotype V capsular polysaccharide may be prepared by treating purified GBS serotype V capsular polysaccharide under mildly acidic conditions (e.g. 0.1M sulphuric acid at 80° C. for 60 minutes) or by treatment with neuraminidase. Thus the polysaccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. In particular, the serotype II and/or III capsular polysaccharides used in the invention may be depolymerised as described in WO96/40795 and Michon et al. *Clin Vaccine Immunol*. (2006) 13(8), 936-43.

The polysaccharide may be chemically modified relative to the capsular polysaccharide as found in nature. For example, the polysaccharide may be de-O-acetylated (partially or fully), de-N-acetylated (partially or fully), N-propionated (partially or fully), etc. De-acetylation may occur before, during or after conjugation, but preferably occurs before conjugation. Depending on the particular polysaccharide, de-acetylation may or may not affect immunogenicity. The relevance of O-acetylation on GBS polysaccharides in various serotypes is discussed in Lewis et al. *PNAS USA* 101, 11123-8 (2004), and in some embodiments O-acetylation of sialic acid residues at positions 7, 8 and/or 9 is retained before, during and after conjugation e.g. by protection/de-protection, by re-acetylation, etc. However, typically the GBS polysaccharide used in the present invention has substantially no O-acetylation of sialic acid residues at positions 7, 8 and/or 9. In particular, when the GBS polysaccharide has been purified by base extraction as described below, then O-acetylation is typically lost. The effect of de-acetylation etc. can be assessed by routine assays.

Capsular polysaccharides can be purified by known techniques, as described in Wessels et al. *Infect Immun* 57, 1089-94 (1989). A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in WO2006/082527 can be used. This involves base extraction, ethanol/CaCl2 treatment, CTAB precipitation, and re-solubilisation. A further alternative process is described in WO2009/081276.

*S. aureus* capsular polysaccharides: Further exemplary bacterial capsular polysaccharides include those from *S. aureus*, particularly the capsular polysaccharides of *S. aureus* type 5 and type 8. The structures of type 5 and type 8 capsular polysaccharides were described in Moreau et al. *Carbohydrate Res*. 339(5), 285-91 (1990) and Fournier et al. *Infect. Immun*. 45(1), 87-93 (1984) as:

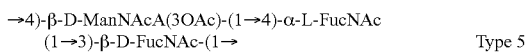
Type 5

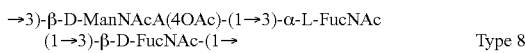
Type 8

Recent NMR spectroscopy data (Jones *Carbohydrate Res*. 340(6), 1097-106 (2005)) has led to a revision of these structures to:

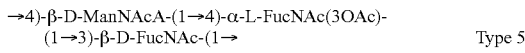
Type 5

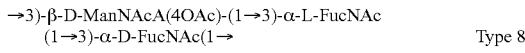
Type 8

The polysaccharide may be chemically modified relative to the capsular polysaccharide as found in nature.

For example, the polysaccharide may be de-O-acetylated (partially or fully), de-N-acetylated (partially or fully), N-propionated (partially or fully), etc. De-acetylation may occur before, during or after conjugation, but typically occurs before conjugation. The effect of de-acetylation etc. can be assessed by routine assays. For example, the relevance of O-acetylation on *S. aureus* type 5 or type 8 capsular polysaccharides is discussed in Fattom et al. *Infect Immun*. 66(10): 4588-92 (1998). The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against *S. aureus* strains that varied in their O-acetyl content. Accordingly, the type 5 or type 8 capsular polysaccharides used in the present invention may have between 0 and 100% 0-acetylation.

The degree of O-acetylation of the polysaccharide can be determined by any method known in the art, for example, by proton NMR (e.g. as described in Lemercinier and Jones *Carbohydrate Res*. 296, 83-96 (1996), Jones and Lemercinier, *J Pharm Biomed Anal*. 30(4), 1233-47 (2002), WO05/033148 or WO 00/56357. A further method is described in Hestrin *J. Biol. Chem*. 180, 249-261 (1949). Similar methods may be used to determine the degree of N-acetylation of the polysaccharide. O-acetyl groups may be removed by hydrolysis, for example by treatment with a base such as anhydrous hydrazine (Konadu et al. *Infect. Immun*. 62, 5048-5054 (1994)) or NaOH (Fattom et al. *Infect Immun*. 66(10): 4588-92 (1998)). Similar methods may be used to remove N-acetyl groups. To maintain high levels of O-acetylation on type 5 and/or 8 capsular polysaccharides, treatments that lead to hydrolysis of the O-acetyl groups are minimised, e.g. treatments at extremes of pH.

Capsular polysaccharides can be purified by known techniques, as described in the references herein. A typical process involves phenol-ethanol inactivation of *S. aureus* cells, centrifugation, lysostaphin treatment, RNase/DNase treatment, centrifugation, dialysis, protease treatment, further dialysis, filtration, precipitation with ethanol/CaCl2, dialysis, freeze-drying, anion exchange chromatography, dialysis, freeze-drying, size exclusion chromatography, dialysis and freeze-drying (Fattom et al. *Infect Immun.* 58(7), 2367-74 (1990)). An alternative process involves autoclaving *S. aureus* cells, ultrafiltration of the polysaccharide-containing supernatant, concentration, lyophilisation, treatment with sodium metaperiodate to remove teichoic acid, further ultrafiltration, diafiltration, high performance size exclusion liquid chromatography, dialysis and freeze-drying (Gilbert et al. *J. Microb. Meth.* 20, 39-46 (1994)).

The invention is not limited to polysaccharides purified from natural sources, however, and the polysaccharides may be obtained by other methods, such as total or partial synthesis.

Other bacterial capsular polysaccharides: Further exemplary bacterial capsular polysaccharides include those from *Haemophilus influenzae* Type b, *Salmonella enterica* Typhi Vi and *Clostridium difficile*.

*S. agalactiae* carbohydrate: The invention may also use non-capsular bacterial polysaccharides. An exemplary non-capsular bacterial polysaccharides is the *S. pyogenes* GAS carbohydrate (also known as the GAS cell wall polysaccharide, or GASP). This polysaccharide features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings (Kreis et al. *Int J Biol Macromol.* 17(3-4), 117-30 (1995)).

The GAS carbohydrate will generally be in its native form, but it may have been modified. For example, the polysaccharide may be shorter than the native GAS carbohydrate, or may be chemically modified.

Thus the polysaccharide used according to the invention may be a substantially full-length GAS carbohydrate, as found in nature, or it may be shorter than the natural length. Full-length polysaccharides may be depolymerised to give shorter fragments for use with the invention e.g. by hydrolysis in mild acid, by heating, by sizing chromatography, etc. A short fragment thought to correspond to the terminal unit on the GAS carbohydrate has been proposed for use in a vaccine (Hoog et al., *Carbohydr Res.* 337(21-23), 2023-36 (2002)). Accordingly, short fragments are envisaged in the present invention. However, it is preferred to use polysaccharides of substantially full-length. The GAS carbohydrate typically has a weight average molecular weight of about 10 kDa, in particular about 7.5-8.5 kDa. Molecular masses can be measured by HPLC, for example SEC-HPLC using a TSK Gel G3000SW column (Sigma) relative to pullulan standards, such as those available from Polymer Standard Service (www. Polymer.de).

The polysaccharide may be chemically modified relative to the GAS carbohydrate as found in nature. For example, the polysaccharide may be de-N-acetylated (partially or fully), N-propionated (partially or fully), etc. The effect of de-acetylation etc., for example on immunogenicity, can be assessed by routine assays.

Polypeptides: The conjugation process described herein can be used with any polypeptide containing at least one tyrosine unit. Generally, the polypeptide has a weight average molecular weight equal to or greater than 10 kDa. In one embodiment, the molecular weight is between about 10 kDa and about 2,000 kDa. In another embodiment, the molecular weight is between about 10 kDa and about 100 kDa. In yet another embodiment, the molecular weight is between about 20 kDa and about 75 kDa.

In some embodiments, the polypeptide of interest already contains one or more tyrosine residues in its sequence. In some embodiments, the polypeptide of interest does not naturally contain any tyrosine residues but such residue(s) is introduced into the sequence. Tyrosine residues can be readily introduced into a polypeptide sequence by, e.g., genetic engineering techniques, for examples, by substitution, mutation, or insertion. The tyrosine residue in a polypeptides can be identified by any techniques know in the art, for example, by sequencing technologies.

In some embodiments, the polypeptide of interest is an antibody or an antigen binding fragment thereof. An "antibody" refers to a polypeptide of the immunoglobulin family that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kDa) and one "heavy" chain (about 50-70 kDa), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibodies that possess a particular binding specifically. Thus, within the scope of this concept are, e.g., full length antibodies, chimeric antibodies, and humanized or human antibodies, and multimeric versions of these antibody fragments (e.g., multispecific, including bispecific, antibodies; multivalent antibodies) with the same binding specificity.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab' which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region. Paul, Fundamental Immunology 3d ed. (1993). While various antibody fragments are defined in terms of the digestion of an intact antibody, one of skill will appreciate that such fragments may be synthesized de novo either chemically or by using recombinant DNA methodology. As used in this application, an "antibody fragment" encompasses all variations of antibody fragments that possess a particular binding specifically. Thus, within the scope of this concept are, e.g., single chain antibodies (ScFv), Fab, Fab', and multimeric versions of these fragments (e.g., F(ab')2,).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce the antibodies. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., Biotechnology, 10:779-783, (1992)).

In one embodiment, the conjugation process described herein is used with an antibody wherein said antibody contains one or more tyrosine residues in its Fc region. In another embodiment, the conjugation process described herein is used with an antibody wherein one or more tyrosine residues are introduced into the Fc region of said antibody at one or more specified positions.

In some embodiments, the polypeptide is an antigenic peptide.

In some embodiments, particularly when R is a polysaccharide, the polypeptide is a carrier molecule. In general, covalent conjugation of polysaccharides to carriers enhances the immunogenicity of polysaccharides as it converts them from T-independent antigens to T-dependent antigens, thus allowing priming for immunological memory. Conjugation is particularly useful for paediatric vaccines, (see for example Ramsay et al. *Lancet* 357(9251):195-196 (2001)) and is a well known technique (see reviews in Lindberg *Vaccine* 17 Suppl 2:S28-36 (1999), Buttery & Moxon, *J R Coll Physicians Lond* 34, 163-168 (2000), Ahmad & Chapnick, *Infect Dis Clin North Am* 13:113-33, vii (1999), Goldblatt *J. Med. Microbiol.* 47, 563-567 (1998), European patent 0477508, U.S. Pat. No. 5,306,492, WO98/42721, Dick et al. *Conjugate Vaccines* (eds. Cruse et al.) Karger, Basel, 10, 48-114 (1989) and Hermanson Bioconjugate Techniques, Academic Press, San Diego (1996) ISBN: 0123423368.

Preferred carrier proteins are bacterial toxins, such as diphtheria or tetanus toxins, or toxoids or mutants thereof, for example CRM197 diphtheria toxin mutant (Research Disclosure, 453077 (January 2002)). *Pseudomonas aeruginosa* exotoxin A (ETA) and its non-toxic mutant recombinant exoprotein A (rEPA) have been used as carrier proteins for *S. aureus* type 5 or type 8 capsular polysaccharides (Fattom et al. *Infect Immun.* 58(7), 2367-74 (1990 and Fattom et al. *Infect Immun.* 60(2), 584-9 (1992)). *S. aureus* α-haemolysin (α-toxin) (Reynaud-Rondier et al. *FEMS Microbiology Immunology* 76, 193-200 (1991) and Herbelin et al. *J Dairy Sci.* 80(9):2025-34 (1997)), ovalbumin (Gilbert et al. *Vaccine* 12(4), 369-74) and human serum albumin (Tollersrud et al. *Vaccine* 19(28-29), 3896-903 (2001)) have also been used. These carriers may be used in the present invention.

Other suitable carrier proteins include the *N. meningitidis* outer membrane protein complex (EP-A-0372501), synthetic peptides (EP-A-0378881, EP-A-0427347), heat shock proteins (WO93/17712, WO94/03208), pertussis proteins (WO98/58668, EP-A-0471177), cytokines (WO91/01146), lymphokines (WO91/01146), hormones (WO91/01146), growth factors (WO91/01146), human serum albumin (typically recombinant), artificial proteins comprising multiple human CD4+ T cell epitopes from various pathogen-derived antigens (Falugi et al. *Eur J Immunol* 31, 3816-3824 (2001)) such as N19 (Baraldo et al. *Infect Immun* 72(8), 4884-7 (2004)), protein D from *H. influenzae* (EP-A-0594610, Ruan et al. *J Immunol* 145, 3379-3384 (1990) and WO00/56360), pneumococcal surface protein PspA (WO02/091998), pneumolysin (Kuo et al. *Infect Immun* 63, 2706-13 (1995)) or its non-toxic derivatives (Michon et al. *Vaccine.* 16, 1732-41 (1998)), iron-uptake proteins (WO01/72337), toxin A or B from *C. difficile* (WO00/61761), a GBS protein (WO2004/041157), a GAS protein (WO02/34771) etc.

Other suitable carrier proteins include *S. aureus* protein antigens.

It is possible to use more than one carrier protein e.g. to reduce the risk of carrier suppression. It is also possible to use more than one carrier protein for a particular polysaccharide antigen. Typically, however, the same carrier protein is used for all polysaccharides.

A single carrier protein might carry more than one polysaccharide antigen (WO99/42130 and WO2004/011027). To achieve this goal, different polysaccharides can be mixed prior to the conjugation process. Typically, however, there are separate conjugates for each polysaccharide, with the different polysaccharides being mixed after conjugation. The separate conjugates may be based on the same carrier.

In one particular embodiment, the polypeptide is CRM197 or Chymotrypsinogen A.

Pharmaceutical Compositions Comprising the Conjugates

The invention provides a pharmaceutical composition comprising (a) a conjugate of Formula (I), and (b) a pharmaceutically acceptable carrier. A thorough discussion of such carriers is available in Gennaro (2000) *Remington: The Science and Practice of Pharmacy.* 20th edition, ISBN: 0683306472.

The compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. Almeida & Alpar (1996) *J. Drug Targeting* 3:455-467]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

The invention also provides a delivery device containing a pharmaceutical composition of the invention. The device may be, for example, a syringe or an inhaler.

Pharmaceutical compositions comprising a conjugate of Formula (I) are preferably immunogenic compositions, particularly when they contain an antigenic peptide or a polysaccharide from a pathogenic organism, in that they comprise an immunologically effective amount of an antigen. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Once formulated, the compositions of the invention can be administered directly to the subject. The subjects to be treated can be animals; in particular, human subjects can be treated. Immunogenic compositions of the invention may be used therapeutically (i.e. to treat an existing infection) or prophylactically (i.e. to prevent future infection). Therapeutic immunisation is particularly useful for treating *Candida* infection in immunocompromised subjects.

An immunogenic composition may include a further adjuvant, which can function to enhance the immune responses (humoral and/or cellular) elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in U.S. Pat. No. 6,355,271). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [WO00/23105]. The adjuvants known as aluminum hydroxide and aluminum phosphate may be used. These names are conventional, but are used for convenience only, as neither is a precise description of the actual chemical compound which is present (e.g. see chapter 9 of *Vaccine Design: The Subunit and Adjuvant Approach* (eds. Powell & Newman) Plenum Press 1995 (ISBN 0-306-44867-X). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc. The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Saponins [chapter 22 of *Vaccine Design: The Subunit and Adjuvant Approach* (eds. Powell & Newman) Plenum Press 1995 (ISBN 0-306-44867-X).], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol [WO96/33739]. Combinations of saponins and cholesterols can be used to form unique particles called immunostimulating complexes (ISCOMs) [chapter 23 of *Vaccine Design: The Subunit and Adjuvant Approach* (eds. Powell & Newman) Plenum Press 1995 (ISBN 0-306-44867-X)]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/33739 and EP-A-0109942. Optionally, the ISCOMS may be devoid of additional detergent [WO00/07621]. A review of the development of saponin based adjuvants can be found in Barr et al. (1998) *Advanced Drug Delivery Reviews* 32:247-271 and Sjolanderet et al. (1998) *Advanced Drug Delivery Reviews* 32:321-338.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [Pizza et al. (2000) *Int J Med Microbiol* 290:455-461]. The use of detoxified ADP-ribosylating toxins as mucosal adjuvants is described in WO95/17211 and as parenteral adjuvants in.

Bioadhesives and mucoadhesives, such as esterified hyaluronic acid microspheres [Singh et al] (2001) *J Cont Release* 70:267-276] or chitosan and its derivatives [WO99/27960].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of *Vaccine Design: The Subunit and Adjuvant Approach* (eds. Powell & Newman) Plenum Press 1995 (ISBN 0-306-44867-X).). Examples of liposome formulations suitable for use as adjuvants are described in U.S. Pat. No. 6,090,406, U.S. Pat. No. 5,916,588 and EP-A-0626169.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

A polyoxidonium polymer [Dyakonova et al. (2004) *Int Immunopharmacol* 4(13):1615-23] or other N-oxidized polyethylene-piperazine derivative.

Methyl inosine 5'-monophosphate ("MIMP") [Signorelli & Hadden (2003) *Int Immunopharmacol* 3(8):1177-86].

A polyhydroxlated pyrrolizidine compound [WO2004/064715], such as one having formula:

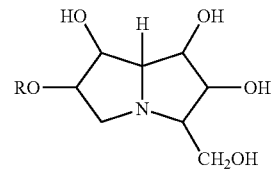

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide De Libero et al, *Nature Reviews Immunology*, 2005, 5: 485-496, U.S. Pat. No. 5,936,076, Oki et al, *J. Clin. Investig.,* 113: 1631-1640 and US2005/0192248 (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3''-O-sulfogalactosylceramide, etc.

A gamma inulin [Cooper (1995) *Pharm Biotechnol* 6:559-80] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. WO99/62923, WO02/26757 and Kandimalla et al. (2003) Nucleic Acids Research 31:2393-2400 disclose possible analog substitutions e.g. replacement of guanosine with 2'-deoxy-7-deazaguanosine. The adjuvant effect of CpG oligonucleotides is further discussed in Krieg (2003) Nature Medicine 9:831-835, McCluskie et al. (2002) FEMS Immunology and Medical Microbiology 32:179-185, WO98/40100 and U.S. Pat. No. 6,207,646. A CpG sequence may be directed to TLR9, such as the motif GTCGTT or TTCGTT [Kandimalla et al. (2003) Biochemical Society Transactions 31 (part 3):654-658]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in Blackwell et al. (2003) J Immunol 170:4061-4068, Krieg (2002) Trends Immunol 23:64-65 and WO01/95935.

Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) Biochemical Society Transactions 31 (part 3):654-658 and Bhagat et al. (2003) BBRC 300:853-861 A useful CpG adjuvant is CpG7909, also known as ProMune™ (Coley Pharmaceutical Group, Inc.). Another is CpG1826. As an alternative, or in addition, to using CpG sequences, TpG sequences can be used [WO01/22972], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in WO01/22972), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in WO01/22972), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™[Schellack et al. (2006) Vaccine 24:5461-72]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2).

3-O-deacylated monophosphoryl lipid A ('3dMPL', also known as 'MPL™') (Myers et al. (1990) pages 145-156 of Cellular and molecular aspects of endotoxin reactions, Johnson et al. (1999) J Med Chem 42:4640-9 and Baldrick et al. (2002) Regulatory Toxicol Pharmacol 35:398-413. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [WO 94/21292]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

An imidazoquinoline compound, such as Imiquimod ("R-837") [U.S. Pat. Nos. 4,680,338, 4,988,815], Resiquimod ("R-848") [WO92/15582], and their analogs; and salts thereof (e.g. the hydrochloride salts). Further details about immunostimulatory imidazoquinolines can be found in Stanley (2002) Clin Exp Dermatol 27:571-577, Vasilakos et al. (2000) Cell Immunol. 204 (1):64-74 and Jones (2003) Curr Opin Investig Drugs 4:214-218.

A thiosemicarbazone compound, such as those disclosed in WO2004/060308. Methods of formulating, manufacturing, and screening for active compounds are also described in WO2004/060308. The thiosemicarbazones are particularly effective in the stimulation of human peripheral blood mononuclear cells for the production of cytokines, such as TNF-α.

A tryptanthrin compound, such as those disclosed in WO2004/064759. Methods of formulating, manufacturing, and screening for active compounds are also described in WO2004/064759. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

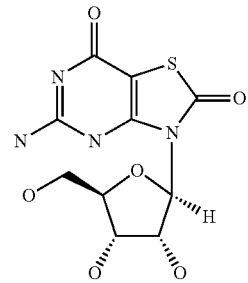 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in U.S. Pat. No. 6,924,271 and US2005/0070556, Loxoribine (7-allyl-8-oxoguanosine) [U.S. Pat. No. 5,011,828].

Compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [WO2004/87153, WO02/18383], Hydrapthalamide compounds, Benzophenone compounds, Isoxazole compounds, Sterol compounds, Quinazilinone compounds, Pyrrole compounds [WO2004/018455], Anthraquinone compounds, Quinoxaline compounds, Triazine compounds, Pyrazalopyrimidine compounds, and Benzazole compounds [WO03/082272].

An aminoalkyl glucosaminide phosphate derivative, such as RC-529 [Johnson et al. (1999) *Bioorg Med Chem Lett* 9:2273-2278 and Evans et al. (2003) *Expert Rev Vaccines* 2:219-229].

A phosphazene, such as poly[di(carboxylatophenoxy) phosphazene] ("PCPP") as described, for example, in Andrianov et al. (1998) *Biomaterials* 19:109-115 and Payne et al. (1998) *Adv Drug Delivery Review* 31:185-196.

A substituted urea or compound of formula I, II or III, or a salt thereof:

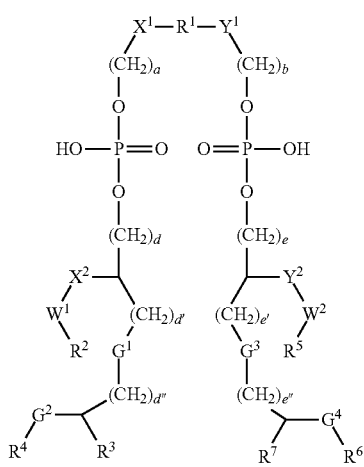

I

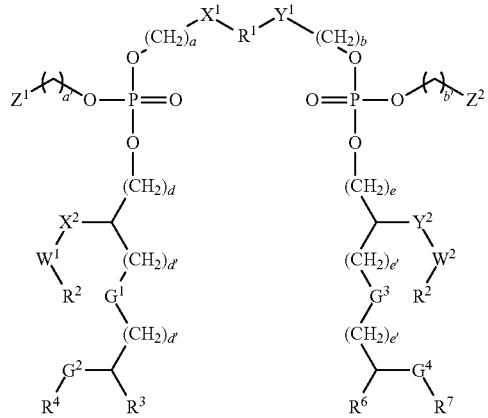

II

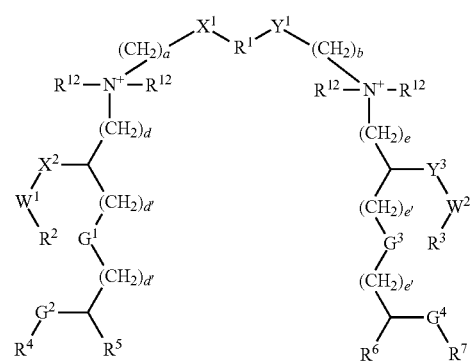

as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

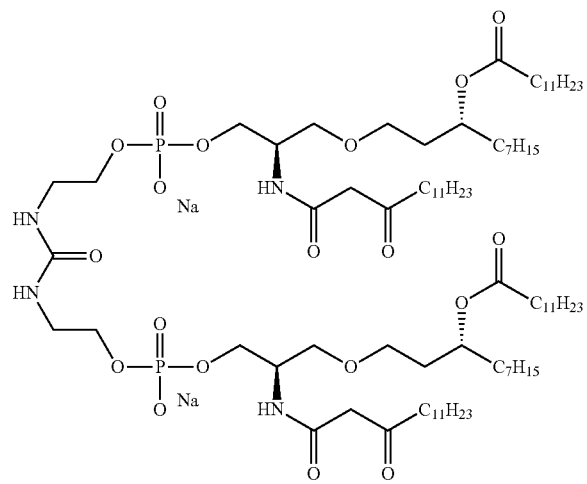

ER804057

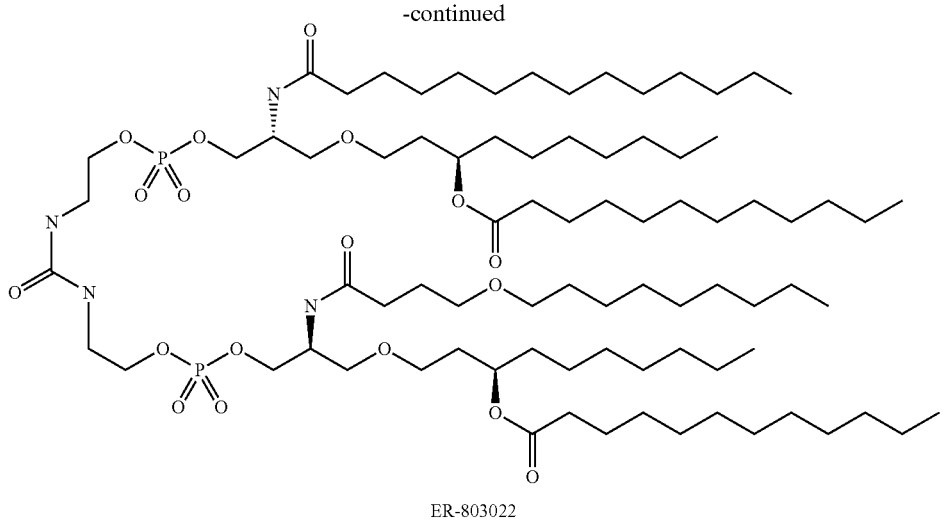

ER-803022

Derivatives of lipid A from Escherichia coil such as OM-174 (described in Meraldi et al. (2003) Vaccine 21:2485-2491 & Pajak et al. (2003) Vaccine 21:836-842).

Compounds containing lipids linked to a phosphate-containing acyclic backbone, such as the TLR4 antagonist E5564 [Wong et al. (2003) J Clin Pharmacol 43(7):735-42]:

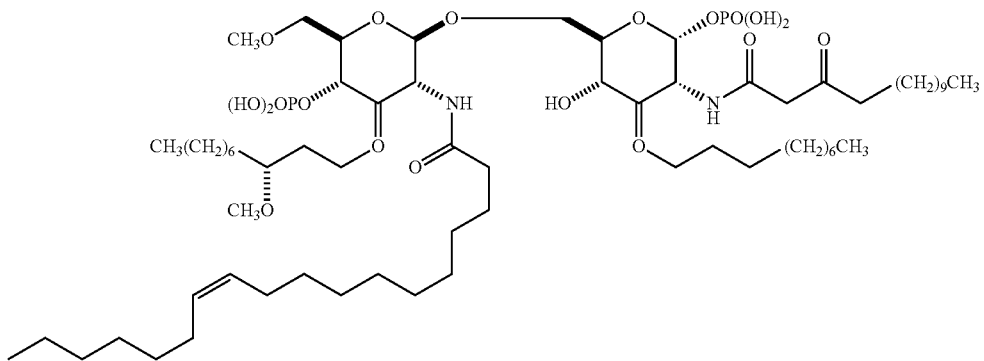

These and other adjuvant-active substances are discussed in more detail in Vaccine Design: *The Subunit and Adjuvant Approach* (eds. Powell & Newman) Plenum Press 1995 (ISBN 0-306-44867-X).

Antigens and adjuvants in a composition will typically be in admixture.

Compositions may include two or more of said adjuvants. For example, they may advantageously include both an oil-in-water emulsion and 3dMPL, etc.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [WO90/14837 and Podda & Del Giudice (2003) Expert Rev Vaccines 2:197-203], as described in more detail in Chapter 10 of Vaccine Design: *The Subunit and Adjuvant Approach* (eds. Powell & Newman) Plenum Press 1995 (ISBN 0-306-44867-X) and chapter 12 of *Vaccine Adjuvants: Preparation Methods and Research Protocols* (Volume 42 of *Methods in Molecular Medicine series*). ISBN: 1-59259-083-7. Ed. O'Hagan. The MF59 emulsion advantageously includes citrate ions e.g. 10mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably <1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [Allison & Byars (1992) Res Immunol 143: 519-25] (0.05-1% Thr-MDP, 5% squalane, 2.5% Pluronic L121 and 0.2% polysorbate 80). It can also be used without the Thr-MDP, as in the "AF" adjuvant [Hariharan et al. (1995) Cancer Res 55:3486-9] (5% squalane, 1.25% Pluronic L121 and 0.2% polysorbate 80). Microfluidisation is preferred.

An emulsion having from 0.5-50% of an oil, 0.1-10% of a phospholipid, and 0.05-5% of a non-ionic surfactant. As described in WO95/11700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in U.S. Pat. No. 6,080,725, produced by addition of aliphatic amine to desacylsaponin via the carboxyl group of glucuronic acid), dimethyidioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [WO2005/097181].

Medical Treatments and Uses

The invention also provides a conjugate of Formula (I) or any subgenus thereof described herein, for use in medicine and for use in therapy. For example, the invention provides a conjugate of of Formula (I) for use in raising an antibody response in a mammal, particularly when the conjugate of Formula (I) contains an antigenic peptide or a polysaccharide from a pathogenic organism. It further provides a method to prepare a medicament comprising the conjugate of Formula (I) or any subgenus thereof described herein.

The invention also provides a method for raising an immune response in a mammal, comprising administering a conjugate or pharmaceutical composition of the invention to the mammal.

The invention also provides the use of a conjugate of the invention in the manufacture of a medicament for preventing or treating a microbial infection in a mammal.

The immune response raised by these methods and uses will generally include an antibody response, preferably a protective antibody response. Methods for assessing antibody responses after antigen immunisation are well known in the art. The antibody response is preferably an IgA or IgG response. The immune response may be prophylactic and/or therapeutic. The mammal is preferably a human.

Efficacy of therapeutic treatment can be tested by monitoring microbial infection after administration of the composition of the invention. Efficacy of prophylactic treatment can be tested by monitoring immune responses against antigen (e.g. anti-antigen antibodies) after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intradermal, ocular, nasal, aural, or pulmonary administration. Injection or intranasal administration is preferred.

The invention may be used to elicit systemic and/or mucosal immunity.

Vaccines prepared according to the invention may be used to treat both children and adults. Thus a subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), or the young (e.g. ≤5 years old). The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

The uses and methods of the invention are particularly useful for treating/protecting against infections caused by the organism from which the antigen is derived. Exemplary uses/methods are discussed below, for embodiments where R is a polysaccharide as set out below.

N. meningitidis Capsular Saccharides

The uses and methods may be for the prevention and/or treatment of a disease caused by N. meningitidis, e.g. meningitis, septicaemia, etc.

Glucans

Because glucans (and β-glucans in particular) are an essential and principal polysaccharide constituent of almost all pathogenic fungi, particularly those involved in infections in immunocompromised subjects, and also in bacterial pathogens and protozoa, anti-glucan immunity may have efficacy against a broad range of pathogens and diseases. For example, anti-glucan serum raised after immunisation with S. cerevisiae is cross-reactive with C. albicans. Broad spectrum immunity is particularly useful because, for these human infectious fungal agents, chemotherapy is scanty, antifungal drug resistance is emerging and the need for preventative and therapeutic vaccines is increasingly recognized.

The uses and methods of the invention are particularly useful for treating/protecting against infections of: Candida species, such as C. albicans; Cryptococcus species, such as C. neoformans; Enterococcus species, such as E. faecalis; Streptococcus species, such as S. pneumoniae, S. mutans, S. agalactiae and S. pyogenes; Leishmania species, such as L. major; Acanthamoeba species, such as A. castellani; Aspergillus species, such as A. fumigatus and A. flavus; Pneumocystis species, such as P. carinii; Mycobacterium species, such as M. tuberculosis; Pseudomonas species, such as P. aeruginosa; Staphylococcus species, such as S. aureus; Salmonella species, such as S. typhimurium; Coccidioides species such as C. immitis; Trichophyton species such as T. verrucosum; Blastomyces species such as B. dermatidis; Histoplasma species such as H. capsulatum; Paracoccidioides species such as P. brasiliensis; Pythium species such as P. insidiosum; and Escherichia species, such as E. coli.

The uses and methods are particularly useful for preventing/treating diseases including, but not limited to: candidiasis (including hepatosplenic candidiasis, invasive candidiasis, chronic mucocutaneous candidiasis and disseminated candidiasis); candidemia; aspergillosis, cryptococcosis, dermatomycoses, sporotrychosis and other subcutaneous mycoses, blastomycosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, cystic fibrosis, typhoid fever, gastroenteritis and hemolytic-uremic syndrome. Anti-*C. albicans* activity is particularly useful for treating infections in AIDS patients.

Conjugates of the invention may be combined with non-glucan antigens into a single composition for simultaneous immunisation against multiple pathogens. As an alternative to making a combined vaccine, conjugates may be administered to patients at substantially the same time as (e.g. during the same medical consultation or visit to a healthcare professional or vaccination centre) other vaccines. Antigens for use in these combination vaccines or for concomitant administration include, for instance, immunogens from *Streptococcus agalactiae, Staphylococcus aureus* and/or *Pseudomonas aeruginosa*, hepatitis A virus, hepatitis B virus, *Neisseria meningitidis* (such as saccharides or conjugated saccharides, for serogroups A, C, W135 and/or Y), *Streptococcus pneumoniae* (such as saccharides or conjugated saccharides), etc.

Conjugates of the invention may be used in conjunction with anti-fungals, particularly where a patient is already infected. The anti-fungal offers an immediate therapeutic effect whereas the conjugate offers a longer-lasting effect. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also Wills et al. (2000) *Emerging Therapeutic Targets* 4:1-32]. The anti-fungal and the conjugate may be administered separately or in combination. When administered separately, they will typically be administered within 7 days of each other. After the first administration of an conjugate, the anti-fungal may be administered more than once.

S. *pneumoniae* Capsular Saccharides

The uses and methods may be for the prevention and/or treatment of a disease caused by pneumococcus, e.g. meningitis, sepsis, pneumonia etc.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Figure 1:
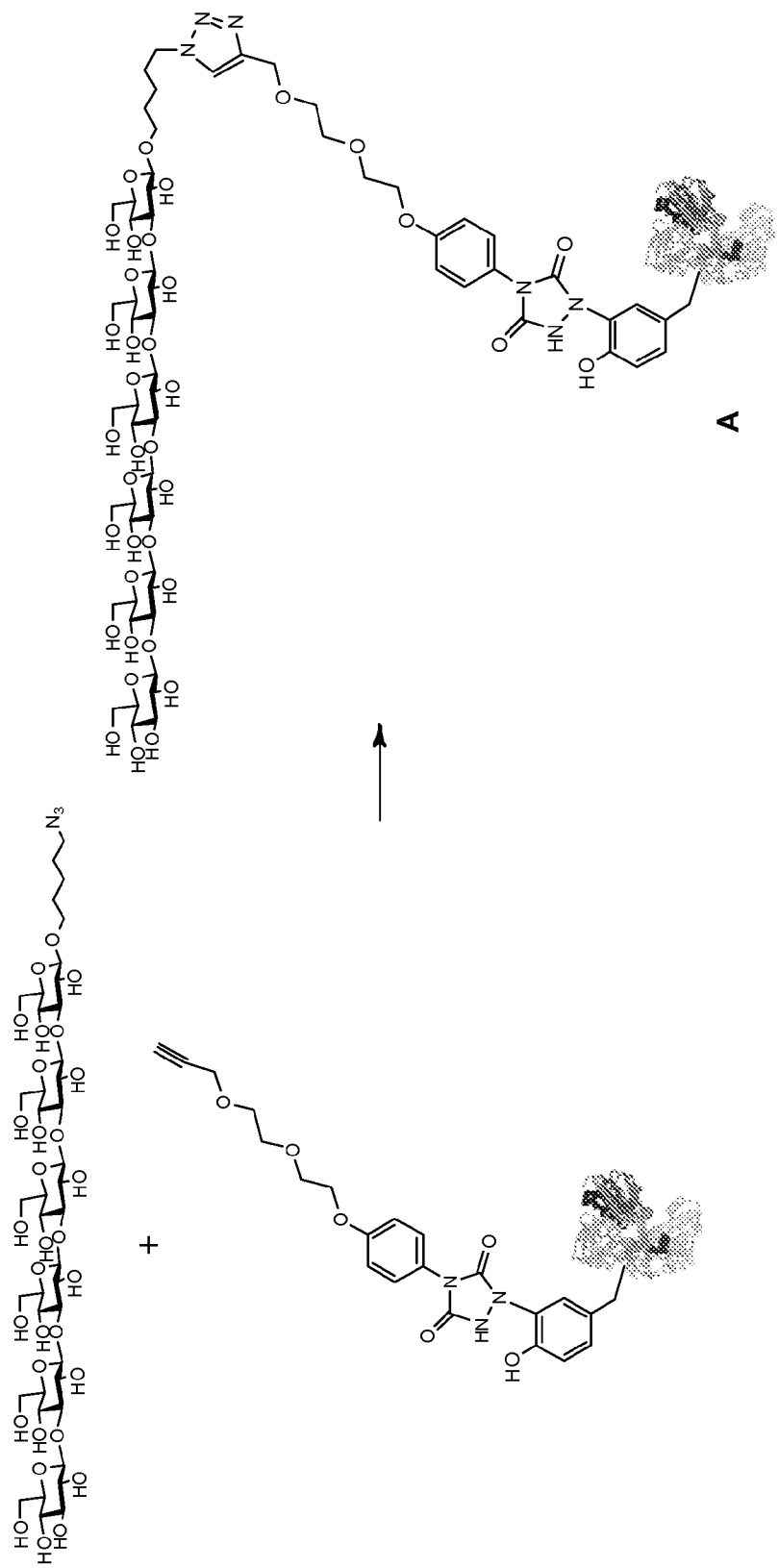
FIG. 1 shows the reaction carried out to effect conjugation of Conjugate 7A with azide modified-saccharide.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), and Tyger Scientific (Princeton, N.J.). The following acronyms used in the examples below have the corresponding meanings.

PBS Phosphate Buffered Saline

PTAD 4-phenyl-3H-1,2,4-triazole-3,5(4H)-dione

Tris tris(hydroxymethyl)aminomethane

PEG-NHS N-hydroxylsuccinimide (NHS) functionalized polyethylene glycol

NBS N-Bromosuccinimide 3-(2-(2-iodoethoxy)ethoxy)prop-1-yne was prepared using the procedures described by Flavia Piron, et al., in "Synthesis of Podands with Cyanurate or Isocyanurate Cores and Terminal Triple Bonds" *Synthesis*, 10, 1639-1644 (2010).

CRM197 (CAS Number 92092-36-9) and Chymotrypsinogen A (CAS Number 9035-75-0) are both available from Aldrich Chemicals Co. (Milwaukee, Wis.).

Example 1

Comparator

Conjugation of CRM197 with PTAD (1A):

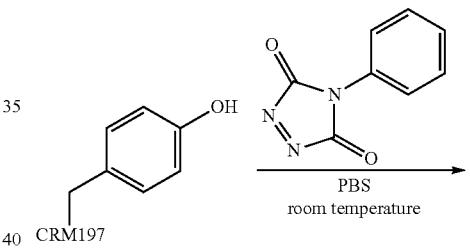

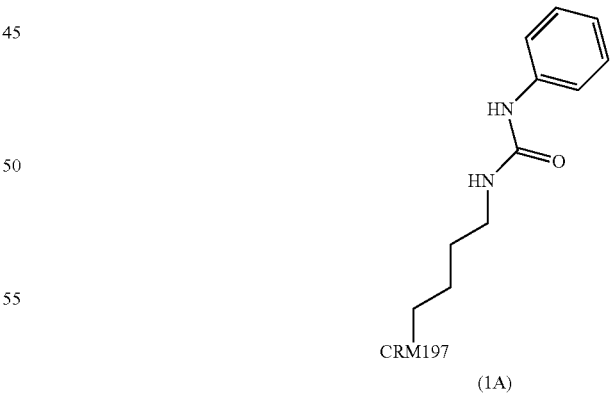

(1A)

To CRM197 (0.116 mg, 0.002 μmol) in PBS pH 7.2 (66 μL) was added a freshly made solution of PTAD (0.2 μL, 0.020 μmol) in CH₃CN. The mixture was agitated at room temperature for 16 hours. LCMS showed approximately 15% conversion: 58402 (+0), 58519 (+1). More PTAD (0.4 μL, 0.040 μmol) in CH₃CN was added, and the mixture was agitated for another 20 hours at room temperature. The mixture was then desalted using a 7K MWCO Zeba spin column. LCMS ESI: 58406 (+0), 58524 (+1), 58645 (+2).

Example 2

Conjugation of CRM197 with 4-phenyl-3H-1,2,4-triazole-3,5(4H)-dione (2A):

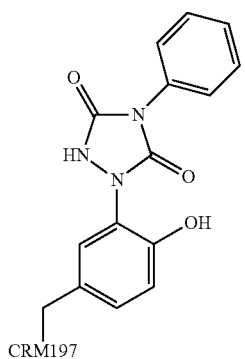
(2A)

To CRM197 (0.03 mg, 0.0005 μmol) in Tris HCl 100 mM pH 7.4 (15 μL) was added a freshly made solution of PTAD (0.500 μL, 0.0050 μmol) in CH$_3$CN. The mixture was agitated at room temperature for 1 hour. The mixture was then desalted using a 7K MWCO Zeba spin column (available from Thermo Scientific). LCMS ESI: 58420 (+0), 58596 (+1), 58769 (+2), 58945 (+3).

Example 3

Conjugation of CRM197 with 4-methyl-3H-1,2,4-triazole-3,5(4H)-dione (3A):

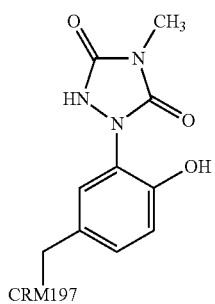
(3A)

Preparation of Intermediate 4-methyl-3H-1,2,4-triazole-3,5(4H)-dione (I-3a);

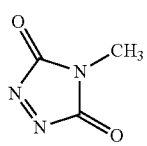
(I-3a)

The dione (I-3a) was prepared using the procedures analogous to those described by Arash Ghorbani-Choghamarani, et al., in "Supported Nitric Acid on Silica Gel and Polyvinyl Pyrrolidone (PVP) as an Efficient Oxidizing Agent for the Oxidation of Urazoles and Bis-urazoles" *Synthetic Communications*, 39(23), 4264-4270 (2009).

To 4-methylurazole (115 mg, 0.999 mmol) in CH$_2$Cl$_2$ (4.996 mL) was added SiO$_2$—HNO$_3$ (250 mg). The mixture was stirred at room temperature for 15 minutes, then filtered, concentrated in vacuo and dried to give 4-methyl-3H-1,2,4-triazole-3,5(4H)-dione as a pink solid (I-2a: 25 mg, 22%). $^1$H NMR (400 MHz, CD$_3$CN) δ ppm 3.08 (s, 3H).

Conjugation to CRM197 to Form the Conjugate (3A):

To CRM197 (0.03 mg, 0.0005 μmol) in Tris HCl 100 mM pH 7.4 (20 μL) was added three portions of a freshly made solution of 4-methyl-3H-1,2,4-triazole-3,5(4H)-dione (I-3a: 0.100 μL each, 0.0025 μmol each, 0.0075 μmol total) in CH$_3$CN. The mixture was agitated at room temperature for 30 minutes. The mixture was desalted using 7K MWCO Zeba spin column. LCMS ESI: 58647 (+2), 58759 (+3), 58874 (+4), 58984 (+5).

Example 4

Conjugation of CRM197 with 4-(4-acetylphenyl)-1,2,4-triazolidine-3,5-dione (4A):

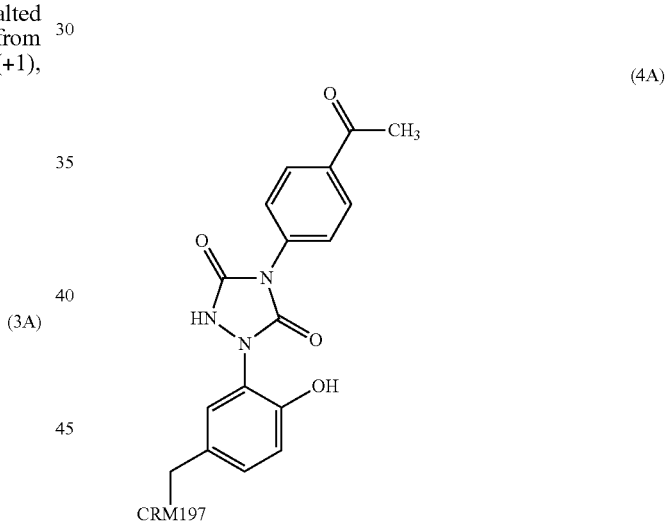
(4A)

Preparation of Intermediate Ethyl 2-(4-acetylphenylcarbamoyl)hydrazinecarboxylate (I-4a):

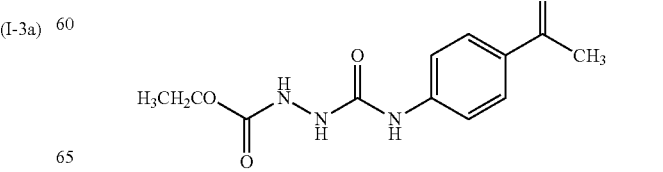
(I-4a)

To 4-aminoacetophenone (676 mg, 5 mmol) in THF (25.000 mL) at 0° C. was added triethylamine (1.386 mL, 10.00 mmol) and 4-nitrophenyl chloroformate (1512 mg, 7.50 mmol). The mixture was stirred at room temperature for 2 hours. Then ethyl carbazate (1562 mg, 15.00 mmol) was added, followed by more triethylamine (2.079 mL, 15.00 mmol). The mixture was stirred at 55° C. for 2 hours. Water was then added, extracted with $CH_2Cl_2$ twice, washed with saturated sodium bicarbonate, dried over $MgSO_4$, filtered, and concentrated in vacuo. The residue was triturated in ethyl acetate, filtered, and concentrated in vacuo. The residue was purified via silica gel chromatography (10-80% ethyl acetate/heptane) giving ethyl 2-(4-acetylphenylcarbamoyl)-hydrazinecarboxylate (354 mg, 27%) as a light yellow solid. LC-MS (M+1) 266.1, t=0.79 minutes.

Preparation of Intermediate 4-(4-acetylphenyl)-1,2,4-triazolidine-3,5-dione (I-4b)

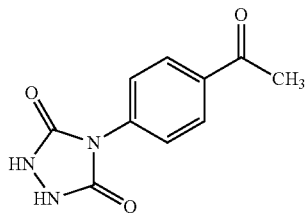

(I-4b)

To ethyl 2-(4-acetylphenylcarbamoyl)hydrazinecarboxylate (I-4a: 354 mg, 1.335 mmol) in MeOH (10 mL) was added $K_2CO_3$ (553 mg, 4.00 mmol). The mixture was stirred at 55° C. for 2 hours, cooled to room temperature, and then HCl 4N in dioxane (1.668 mL, 6.67 mmol) was added. The precipitate was filtered, and the filtrate was concentrated in vacuo. The resulting solid was triturated in $CH_2Cl_2$, filtered and dried giving 4-(4-acetylphenyl)-1,2,4-triazolidine-3,5-dione (I-4b: 125 mg, 43%) as a light yellow solid. LC-MS (M+1) 220.2, t=0.78 minute. $^1H$ NMR (400 MHz, DMSO-$d_6$) δ ppm 2.60 (s, 3 H) 7.68 (d, J=8.84 Hz, 2 H) 8.05 (d, J=8.59 Hz, 2 H) 10.65 (s, 2 H).

Preparation of Intermediate 4-(4-acetylphenyl)-3H-1,2,4-triazole-3,5(4H)-dione (I-4c):

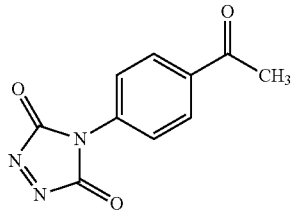

(I-4c)

To 4-(4-acetylphenyl)-1,2,4-triazolidine-3,5-dione (115 mg, 0.999 mmol) in $CH_2Cl_2$ (3.5 mL) was added SiO2-HNO3 (300 mg). The mixture was stirred at room temperature for 15 minutes, filtered, concentrated in vacuo and dried to give 4-(4-acetylphenyl)-3H-1,2,4-triazole-3,5(4H)-dione as a red solid (78 mg, 74%).

Conjugation to CRM197 to Form the Conjugate (4A):

To CRM197 (0.0005 μmol) in Tris HCl 100 mM pH 7.4 (25.00 μL) was added two additions of 4-(4-acetylphenyl)-3H-1,2,4-triazole-3,5(4H)-dione (I-4c: 0.200 μL, 0.00100 μmol) in $CH_3CN$ every minute (total of 4 equivalents added). The mixture was agitated for 15 minutes followed by the addition of more reagent (10 equivalents). The mixture was then agitated for another 15 minutes. More reagent was added (10 equivalents) and the mixture was then agitated for another 15 minutes. The mixture was then desalted using Zeba 7K MWCO column. LCMS ESI: 58644 (+1), 58865 (+2), 59072 (+3).

Example 5

Conjugation of CRM197 with (E)-4-(4-(1-(benzyloxyimino)ethyl)phenyl)-3H-1,2,4-triazole-3,5(4H)-dione (5A):

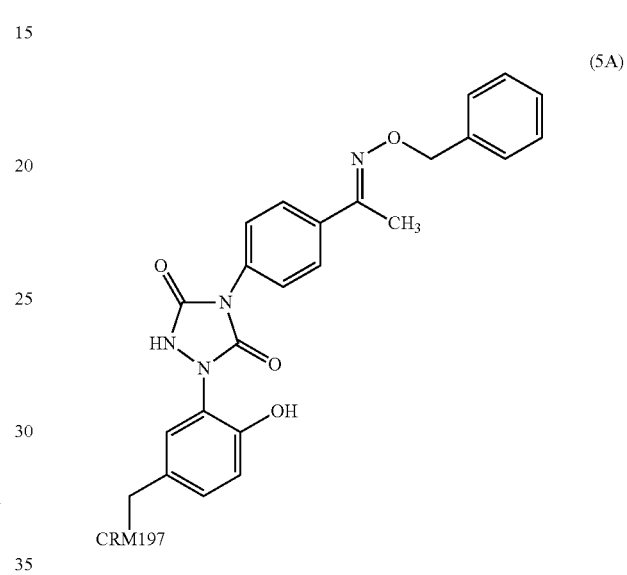

(5A)

Preparation of Intermediate (E)-4-(4-(1-(benzyloxyimino)ethyl)phenyl)-1,2,4-triazolidine-3,5-dione (I-5a):

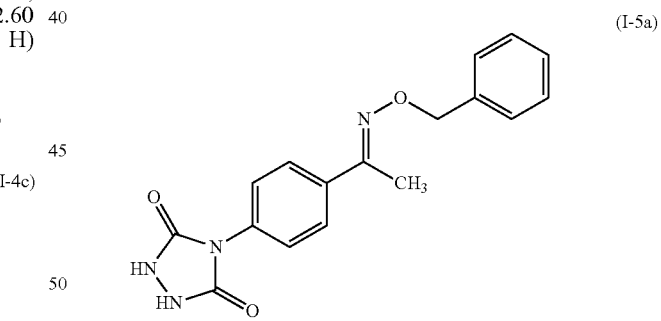

(I-5a)

To 4-(4-acetylphenyl)-1,2,4-triazolidine-3,5-dione (500 mg, 2.281 mmol) in ethanol (6.91 mL) was added O-benzylhydroxylamine hydrochloride (728 mg, 4.56 mmol) and HCl 4N in dioxane (0.277 mL, 9.12 mmol). The mixture was stirred at 65° C. for 1 hour, filtered, and then concentrated in vacuo. Saturated sodium bicarbonate added to the residue, extracted with ethyl acetate twice, dried over $MgSO_4$, filtered, and concentrated in vacuo. Methanol/$CH_2Cl_2$ (50/50) was added, then the precipitate was filtered and dried, giving (E)-4-(4-(1-(benzyloxyimino)ethyl)-phenyl)-1,2,4-triazolidine-3,5-dione (I-5a: 167 mg, 23%) as a white solid. LC-MS (M+1) 325.1, t=1.77 minutes. $^1$H NMR (400 MHz, DMSO-$d_6$) δ ppm 2.60 (s, 3 H) 7.68 (d, J=8.84 Hz, 2 H) 8.05 (d, J=8.59 Hz, 2 H) 10.65 (s, 2 H). $^1$H NMR (400 MHz, $CD_3CN$) δ ppm 2.29 (s, 3 H) 5.26 (s, 2 H) 7.37 (d, J=7.07 Hz, 1 H) 7.42 (t, J=7.33 Hz, 2 H) 7.45-7.50 (m, 2 H) 7.53 (d, J=8.59 Hz, 2 H) 7.75-7.93 (m, 4 H).

Preparation of Intermediate (E)-4-(4-(1-(benzyloxy-imino)ethyl)phenyl)-3H-1,2,4-triazole-3,5(4H)-dione (I-5b):

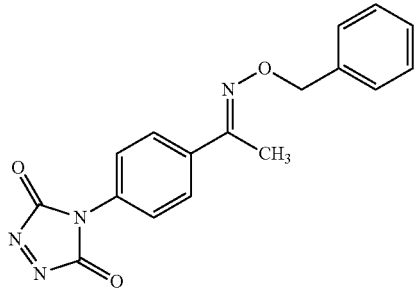

(I-5b)

To (E)-4-(4-(1-(benzyloxyimino)ethyl)phenyl)-1,2,4-triazolidine-3,5-dione (I-5a: 56 mg, 0.173 mmol) in CH$_2$Cl$_2$ (1.727 mL) was added SiO$_2$—HNO$_3$ (112 mg). The mixture was stirred at room temperature for 30 minutes, filtered, concentrated in vacuo and dried to give (E)-4-(4-(1-(benzyloxy-imino)ethyl)phenyl)-3H-1,2,4-triazole-3,5(4H)-dione (I-4b: 29 mg, 52%) as a red solid. $^1$H NMR (400 MHz, CD3CN) δ ppm 2.31 (s, 3 H) 5.28 (s, 2 H) 7.38 (d, J=7.07 Hz, 1 H) 7.43 (t, J=7.20 Hz, 2 H) 7.46-7.54 (m, 4 H) 7.86-7.94 (m, 2 H).

Conjugation to CRM197 to Form Conjugate (5A);

To CRM197 (0.0005 μmol) in Tris HCl 100 mM pH 7.4 (16.7 μL) was added two additions of (E)-4-(4-(1-(benzyloxy)ethyl)phenyl)-3H-1,2,4-triazole-3,5(4H)-dione (I-5b: 0.100 μL, 0.00100 μmol) in CH$_3$CN every minute (total of 4 equivalents added). The mixture was agitated for 15 minutes followed by the addition of more reagent (10 equivalents). The mixture was agitated for another 15 minutes and then desalted using Zeba 7K MWCO column. LCMS ESI: 58413 (+0), 58736 (+1), 59061 (+2).

Example 6

Conjugation of CRM197 with (E)-4-(4-(1-(prop-2-ynyloxyimino)ethyl)phenyl)-3H-1,2,4-triazole-3,5(4H)-dione (6A):

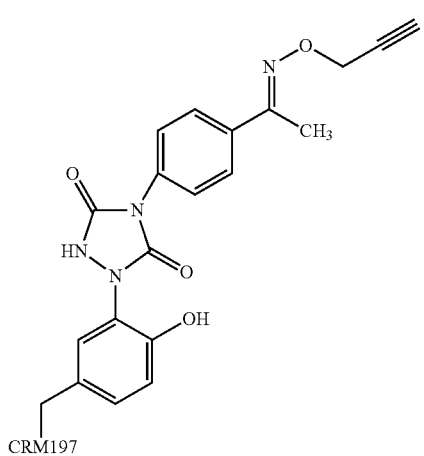

(6A)

Preparation of Intermediate (E)-4-(4-(1-(prop-2-ynyloxyimino)ethyl)phenyl)-1,2,4-triazolidine-3,5-dione (I-6a):

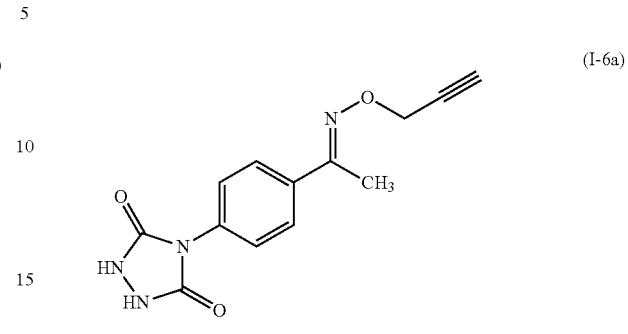

(I-6a)

To 4-(4-acetylphenyl)-1,2,4-triazolidine-3,5-dione (500 mg, 2.281 mmol) in ethanol (6.912 mL) was added O-(prop-2-ynyl)hydroxylamine hydrochloride (368 mg, 3.42 mmol) and HCl 4N in dioxane (1.711 mL, 6.84 mmol). The mixture was stirred at 50° C. for 2 hours and then concentrated in vacuo. Saturated sodium bicarbonate was added, extracted with ethyl acetate twice, dried over MgSO$_4$, filtered, and concentrated in vacuo. The residue was purified by silica gel chromatography (60-100% ethyl acetate/heptane, and then 5% MeOH/ethyl acetate) giving (E)-4-(4-(1-(prop-2-ynyloxyimino)ethyl)phenyl)-1,2,4-triazolidine-3,5-dione (I-6a: 46 mg, 7%) as a white solid. LC-MS (M+1) 273.1, t=0.81 minute. $^1$H NMR (400 MHz, DMSO-d$_6$) δ ppm 2.23 (s, 3 H) 3.48 (t, J=2.40 Hz, 1 H) 4.80 (d, J=2.27 Hz, 2 H) 7.53 (d, J=8.59 Hz, 2 H) 7.76 (d, J=8.59 Hz, 2 H) 10.52 (s, 2 H).

Preparation of Intermediate (E)-4-(4-(1-(prop-2-ynyloxyimino)ethyl)phenyl)-3H-1,2,4-triazole-3,5(4H)-dione (I-6b):

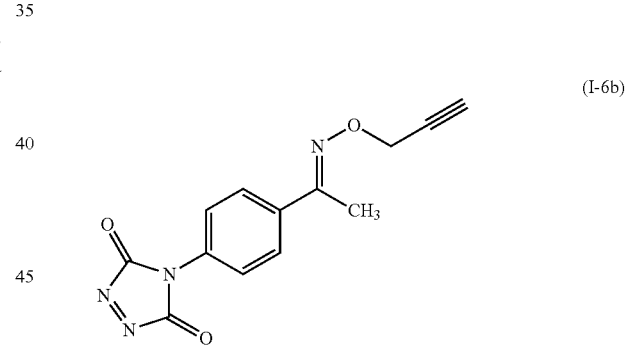

(I-6b)

To (E)-4-(4-(1-(prop-2-ynyloxyimino)ethyl)phenyl)-1,2,4-triazolidine-3,5-dione (I-6a: 46 mg, 0.169 mmol) in CH$_2$Cl$_2$ (1.69 mL) was added SiO$_2$—HNO$_3$ (100 mg). The mixture was stirred at room temperature for 30 minutes, filtered, concentrated in vacuo and dried to give (E)-4-(4-(1-(prop-2-ynyloxyimino)ethyl)phenyl)-3H-1,2,4-triazole-3,5(4H)-dione (24 mg, 53%) as a red solid. $^1$H NMR (400 MHz, CD$_3$CN) δ ppm 2.31 (s, 3 H) 5.28 (s, 2 H) 7.38 (d, J=7.07 Hz, 1 H) 7.43 (t, J=7.20 Hz, 2 H) 7.46-7.54 (m, 4 H) 7.86-7.94 (m, 2 H). $^1$H NMR (400 MHz, CD$_3$CN) δ ppm 2.31 (s, 3 H) 2.81 (t, J=2.40 Hz, 1 H) 4.84 (d, J=2.27 Hz, 2 H) 7.53 (d, J=8.84 Hz, 2 H) 7.93 (d, J=8.84 Hz, 2 H).

Conjugation to CRM197 (6A):

To CRM197 (0.001 μmol) in Tris HCl 100 mM pH 7.4 (50.0 μL) was added 6 additions of (E)-4-(4-(1-(prop-2-ynyloxyimino)ethyl)phenyl)-3H-1,2,4-triazole-3,5(4H)-dione (I-6b: 0.400 μL, 0.0020 μmol) in CH$_3$CN every minute (total of 12 equivalents added). The mixture was then agitated for another hour and desalted using 7K MWCO Zeba Spin column. LCMS ESI: 58418 (+0), 58688 (+1), 58960 (+2).

Example 7

CRM197 conjugated with 4-(4-(2-(2-(prop-2-ynyloxy)ethoxy)ethoxy)phenyl)-3H-1,2,4-triazole-3,5(4H)-dione (7A):

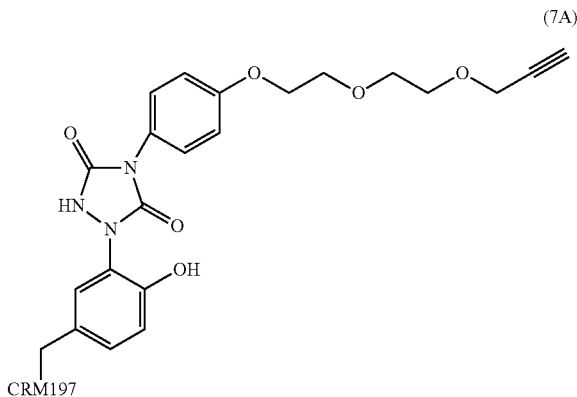

(7A)

To tert-butyl 4-(2-(2-(prop-2-ynyloxy)ethoxy)ethoxy)phenylcarbamate (I-7a: 1.91 g, 5.69 mmol) in $CH_2Cl_2$ (14.24 mL) was added 4N HCl in dioxane (14.24 mL, 56.9 mmol). The mixture was stirred at room temperature for 2 hours, concentrated in vacuo, followed by the addition of aqueous saturated sodium bicarbonate. The mixture was then extracted twice with ethyl acetate, dried over $MgSO_4$, filtered, and concentrated in vacuo. 4-(2-(2-(prop-2-ynyloxy)ethoxy)ethoxy)aniline (I-7b) was used as is for next step. LC-MS (M+1) 236.1, t=0.87 minute.

Preparation of Intermediate Ethyl 2-(4-(2-(2-(prop-2-ynyloxy)ethoxy)ethoxy)-phenylcarbamoyl)hydrazinecarboxylate (I-7c):

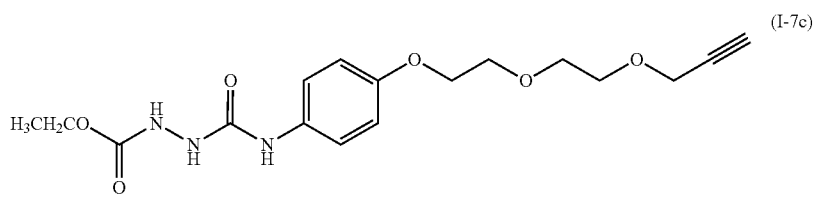

(I-7c)

Preparation of Intermediate tert-butyl 4-(2-(2-(prop-2-ynyloxy)ethoxy)ethoxy)phenylcarbamate (I-7a):

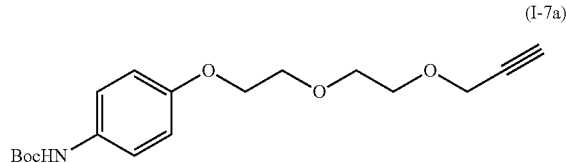 [SMILES: C#CCOCCOCCOc1ccc(NC(=O)OC(C)(C)C)cc1]

(I-7a)

To tert-butyl 4-hydroxyphenylcarbamate (1.675 g, 8.01 mmol) in DMF (53.4 mL) was added 3-(2-(2-iodoethoxy)ethoxy)prop-1-yne (2.034 g, 8.01 mmol) and $K_2CO_3$ (3.32 g, 24.02 mmol). The mixture was stirred at 60° C. for 4 hours followed by the addition of saturated sodium bicarbonate. The mixture was then extracted with ethyl acetate twice, dried over $MgSO_4$, filtered, and then concentrated in vacuo. The residue was purified by silica gel chromatography (0-40% ethyl acetate/heptane) giving tert-butyl 4-(2-(2-(prop-2-ynyloxy)ethoxy)ethoxy)-phenylcarbamate (I-7a: 1.91 g, 71%) as a colorless oil. LC-MS (M-tBu+1) 280.1, t=1.31 minute.

Preparation of Intermediate 4-(2-(2-(prop-2-ynyloxy)ethoxy)ethoxy)aniline (I-7b):

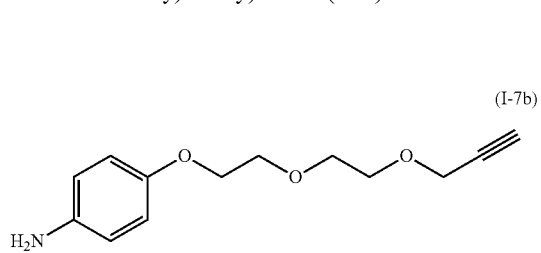

(I-7b)

To 4-(2-(2-(prop-2-ynyloxy)ethoxy)ethoxy)aniline (I-7b: 1.339 g, 5.69 mmol) in THF (37.9 mL) at 0° C. was added 4-nitrophenyl chloroformate (2.064 g, 10.24 mmol) and triethylamine (1.420 mL, 10.24 mmol). The mixture was stirred at room temperature for 1 hour. Then ethyl carbazate (1.540 g, 14.79 mmol) and more triethylamine (1.420 mL, 10.24 mmol) were added. The mixture was stirred at room temperature for 16 hours, followed by the addition of aqueous saturated sodium bicarbonate. The mixture was then extracted twice with ethyl acetate, dried over $MgSO_4$, filtered, and then concentrated in vacuo. The crude product was purified by silica gel chromatography (40-100% ethyl acetate/heptane) giving ethyl 2-(4-(2-(2-(prop-2-ynyloxy)ethoxy)ethoxy)phenylcarbamoyl)-hydrazinecarboxylate (I-7c: 1.31 g, 63%) as a foamy colorless oil. LC-MS (M+1) 366.1, t=0.95 minute.

Preparation of Intermediate 4-(4-(2-(2-(prop-2-ynyloxy)ethoxy)ethoxy)phenyl)-1,2,4-triazolidine-3,5-dione (I-7d):

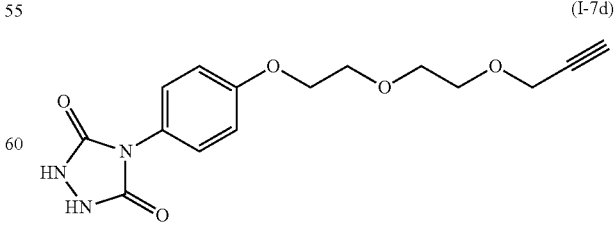

(I-7d)

To ethyl 2-(4-(2-(2-(prop-2-ynyloxy)ethoxy)ethoxy)phenylcarbamoyl)-hydrazinecarboxylate (1.31 g, 3.59 mmol) in methanol (17.93 mL) was added $K_2CO_3$ (1.239 g, 8.96 mmol). The mixture was stirred at 55° C. for 30 minutes. After cooling to room temperature, 4N HCl in dioxane (3.59 mL, 14.34 mmol) was added. The precipitate was filtered, and the filtrate was concentrated in vacuo. The residue was then purified by silica gel chromatography (40-100% ethyl acetate/heptane) giving 4-(4-(2-(2-(prop-2-ynyloxy)ethoxy)ethoxy)phenyl)-1,2,4-triazolidine-3,5-dione (I-7d: 318 mg, 28%) as a white oily solid. LC-MS (M+1) 320.0, t=0.73 minute. $^1$H NMR (400 MHz, CDCl$_3$) δ ppm 2.48 (t, J=2.15 Hz, 1 H) 3.68-3.83 (m, 4 H) 3.83-3.97 (m, 2 H) 4.11-4.32 (m, 4 H) 7.04 (d, J=8.84 Hz, 2 H) 7.36 (d, J=8.84 Hz, 2 H).

Preparation of Intermediate 4-(4-(2-(2-(prop-2-ynyloxy)ethoxy)ethoxy)phenyl)-3H-1,2,4-triazole-3,5(4H)-dione (I-7e):

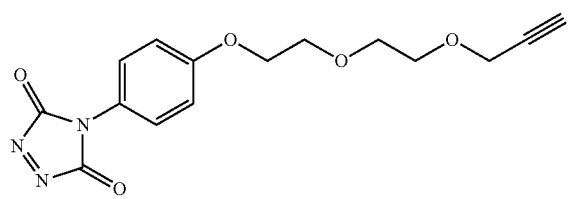

(I-7e)

To 4-(4-(2-(2-(prop-2-ynyloxy)ethoxy)ethoxy)phenyl)-1,2,4-triazolidine-3,5-dione (I-7d: 153 mg, 0.479 mmol) in CH$_2$Cl$_2$ (4.792 mL) was added SiO2-HNO3 (300 mg). The mixture was stirred at room temperature for 15 minutes, then filtered, concentrated in vacuo and dried giving 4-(4-(2-(2-(prop-2-ynyloxy)ethoxy)ethoxy)phenyl)-3H-1,2,4-triazole-3,5(4H)-dione (112 mg, 74%) as a red oil. $^1$H NMR (400 MHz, CD$_3$CN) δ ppm 2.60 (t, J=2.40 Hz, 1 H) 3.44-3.62 (m, 4 H) 3.68-3.75 (m, 2 H) 4.02-4.12 (m, 4 H) 7.02 (d, J=9.09 Hz, 2 H) 7.23 (d, J=8.84 Hz, 2 H).

Conjugation to CRM197 to Form Conjugate 7A:

To CRM197 (0.034 µmol) in Tris HCl 100 mM pH 7.4 (1.369 mL) was added 8 additions of 4-(4-(2-(2-(prop-2-ynyloxy)ethoxy)ethoxy)phenyl)-3H-1,2,4-triazole-3,5(4H)-dione (I-6e: 1.712 µL, 0.171 µmol) in CH$_3$CN every minute (total of 40 equivalents added), agitated for 1 hour, and then desalted using a Zeba spin column 7K MWCO. LCMS ESI: 58740 (+1), 59061 (+2), 59381 (+3), 59699 (+4).

Example 8

Conjugation of CRM197 with tert-butyl 4-(3,5-dioxo-1,2,4-triazolidin-4-yl)butylcarbamate (8A):

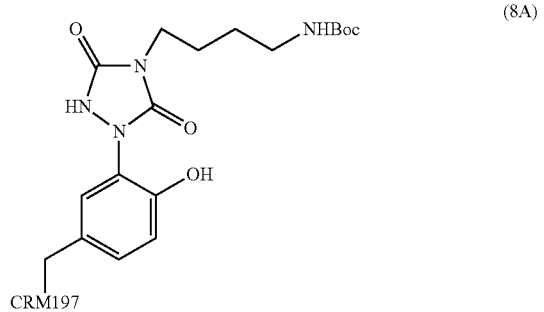

(8A)

Preparation of Intermediate Ethyl 13,13-dimethyl-4,11-dioxo-12-oxa-2,3,5,10-tetraazatetradecan-1-oate (I-8a):

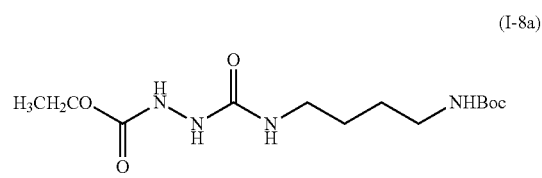

(I-8a)

To 4-nitrophenyl chloroformate (1.008 g, 5.00 mmol) in THF (25.00 mL) at 0° C. was added ethyl carbazate (0.521 g, 5 mmol) and triethylamine (1.525 mL, 11.00 mmol). The mixture was stirred at 0° C. for 1 hour. Then N-Boc-1,4-butanediamine (1.148 mL, 6.00 mmol) was added. The mixture was stirred at room temperature for 1 hour. Water was then added, extracted twice with ethyl acetate, dried over MgSO$_4$, filtered, and concentrated in vacuo. The crude product was purified by silica gel chromatography (0-10% MeOH/CH$_2$Cl$_2$) giving ethyl 13,13-dimethyl-4,11-dioxo-12-oxa-2,3,5,10-tetraazatetradecan-1-oate (I-8a: 1.045 g, 66%) as a white solid. LC-MS (M+1) 319.1, t=0.92 minute.

Preparation of Intermediate tert-butyl 4-(3,5-dioxo-1,2,4-triazolidin-4-yl)butylcarbamate (I-8b):

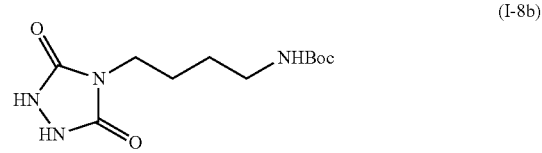

(I-8b)

To ethyl 13,13-dimethyl-4,11-dioxo-12-oxa-2,3,5,10-tetraazatetradecan-1-oate (I-8a: 1.045 g, 3.28 mmol) in EtOH (13.13 mL) was added K2CO3 (1.815 g, 13.13 mmol). The mixture was stirred at 65° C. for 16 hours. Cooled to room temperature, filtered, and then 4N HCl in dioxane was added up to pH or approximately 4. The white solid was filtered, rinsed with some methanol, and then the filtrate was concentrated in vacuo. The residue was purified by silica flash chromatography (0-10% MeOH/CH$_2$Cl$_2$) giving tert-butyl 4-(3,5-dioxo-1,2,4-triazolidin-4-yl)butylcarbamate (388 mg, 43%) as a oily white solid. LC-MS (M–1) 271.1, t=0.73 minute. $^1$H NMR (400 MHz, CD$_3$CN) δ ppm 1.39 (s, 9 H) 1.42-1.49 (m, 2 H) 1.52-1.65 (m, 2 H) 3.03 (q, J=6.40 Hz, 2 H) 3.42 (t, J=6.95 Hz, 2 H).

Preparation of Intermediate tert-butyl 4-(3,5-dioxo-3H-1,2,4-triazol-4(5H)-yl)butylcarbamate (I-8c):

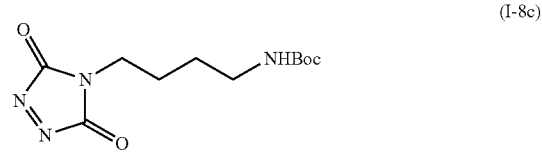 [SMILES: CC(C)(C)OC(=O)NCCCCN1C(=O)N=NC1=O]

(I-8c)

To tert-butyl 4-(3,5-dioxo-1,2,4-triazolidin-4-yl)butylcarbamate (15 mg, 0.055 mmol) in CH$_2$Cl$_2$ (0.551 mL) was added SiO$_2$—HNO$_3$ (35 mg). The mixture was stirred at room temperature for 15 minutes, then filtered, concentrated in vacuo and dried, giving tert-butyl 4-(3,5-dioxo-3H-1,2,4-triazol-4(5H)-yl)butylcarbamate (I-8c: 15 mg, quantitative yield) as a red oil.

Conjugation to CRM197 to Form Conjugate (8A):

To CRM197 (0.0005 µmol) in Tris HCl 100 mM pH 7.4 (20.0 µL) was added three portions of tert-butyl 4-(3,5-dioxo-3H-1,2,4-triazol-4(5H)-yl)butylcarbamate (I-8c: 0.100 µL, 0.0025 µmol) in CH₃CN every minute (total of 15 equivalents). The mixture was agitated at room temperature for 30 minutes. LCMS ESI: 58687 (+1), 58964 (+2), 59228 (+3).

Example 9

Conjugation of CRM197 with N-(4-(3,5-dioxo-3H-1,2,4-triazol-4(5H)-yl)butyl)-2-methoxy(polyethyleneglycol)-acetamide (9A):

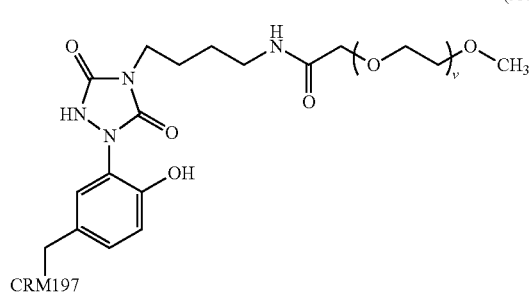

(9A)

Preparation of Intermediate Ethyl 4,11-dioxo-13-phenyl-12-oxa-2,3,5,10-tetraazatridecan-1-oate (I-9a):

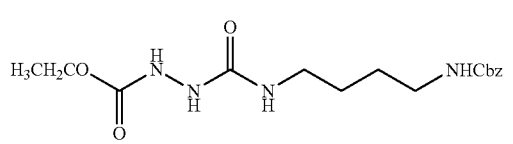

(I-9a)

To 4-nitrophenyl chloroformate (1.008 g, 5.00 mmol) in THF (25.000 mL) at 0° C. was added ethyl carbazate (0.521 g, 5 mmol) and triethylamine (2.218 mL, 16.00 mmol). The mixture was stirred at 0° C. for 1 hour. Benzyl 4-aminobutylcarbamate hydrochloride (1.552 g, 6.00 mmol) was then added. The mixture was stirred at room temperature for 1 hour, water was then added, extracted twice with ethyl acetate, dried over MgSO₄, filtered, and concentrated in vacuo. The crude product was purified by silica gel chromatography (40-100% ethyl acetate/heptane) giving ethyl 4,11-dioxo-13-phenyl-12-oxa-2,3,5,10-tetraazatridecan-1-oate (I-9a: 965 mg, 55%) as a white solid. LC-MS (M+1) 353.2, t=0.94 minute.

Preparation of Intermediate Benzyl 4-(3,5-dioxo-1,2,4-triazolidin-4-yl)butylcarbamate (I-9b):

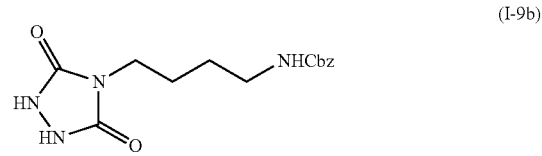 [SMILES: O=C(NCCCCn1c(=O)[nH][nH]c1=O)OCc1ccccc1]

(I-9b)

To ethyl 4,11-dioxo-13-phenyl-12-oxa-2,3,5,10-tetraazatridecan-1-oate (I-9a: 965 mg, 2.74 mmol) in ethanol (11.000 mL) was added K₂CO₃ (1514 mg, 10.95 mmol). The mixture was stirred at 65° C. for 16 hours, cooled to room temperature, filtered, and then 4N HCl in dioxane was added up to a pH of approximately 4. The resultant white solid was filtered, rinsed with some methanol, and then concentrated in vacuo. The residue was purified by silica gel chromatography (40-100% ethyl acetate/heptane) giving benzyl 4-(3,5-dioxo-1,2,4-triazolidin-4-yl)butylcarbamate (I-9b: 369 mg, 44%) as a white solid. LC-MS (M+1) 307.1, t=0.78 minute. ¹H NMR (400 MHz, MeOD) δ ppm 1.40-1.58 (m, 2 H) 1.58-1.74 (m, 2 H) 3.15 (t, J=6.82 Hz, 2 H) 3.51 (t, J=6.95 Hz, 2 H) 5.06 (s, 2 H) 7.21-7.42 (m, 5 H).

Preparation of Intermediate 4-(4-aminobutyl)-1,2,4-triazolidine-3,5-dione (I-9c):

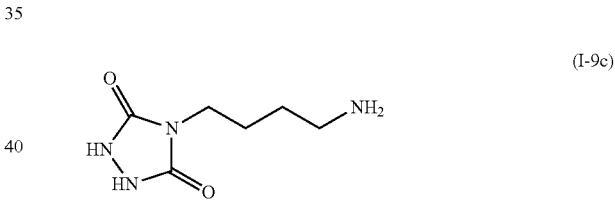

(I-9c)

To benzyl 4-(3,5-dioxo-1,2,4-triazolidin-4-yl)butylcarbamate (I-9b: 369 mg, 1.205 mmol) in methanol (4.819 mL) was added 10% Pd/C (51.3 mg, 0.048 mmol). The mixture was stirred at room temperature for 1 hour under 1 atm of H₂, filtered over celite, rinsed with more methanol, concentrated in vacuo and dried to give 4-(4-aminobutyl)-1,2,4-triazolidine-3,5-dione (I-9c: 105 mg, 51%) as a white solid. ¹H NMR (400 MHz, MeOD) δ ppm 1.51-1.79 (m, 4 H) 2.94 (t, J=7.20 Hz, 2 H) 3.50 (t, J=6.57 Hz, 2 H).

Preparation of Intermediate N-(4-(3,5-dioxo-1,2,4-triazolidin-4-yl)butyl)-2-methoxyPEG-acetamide (I-9d):

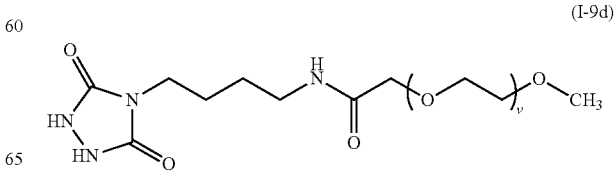

(I-9d)

To 4-(4-aminobutyl)-1,2,4-triazolidine-3,5-dione (I-9c: 13.28 mg, 0.077 mmol) in methanol (1.542 mL) was added 5000 molecular weight mPEG NHS ester (40 mg, 7.71 μmol) and triethylamine (5.34 μL, 0.039 mmol). The mixture was stirred at room temperature for 1 hour. Excess amine was removed using Si-carboxylic acid cartridge (1 g, 6 mL), using methanol as eluent. The residue was concentrated in vacuo and dried, giving N-(4-(3,5-dioxo-1,2,4-triazolidin-4-yl)butyl)-2-methoxy(polyethylene glycol)-acetamide (I-9d: 33.5 mg, 82%) as a white solid.

Preparation of Intermediate N-(4-(3,5-dioxo-3H-1,2,4-triazol-4(5H)-yl)butyl)-2-methoxyPEG-acetamide (I-9e):

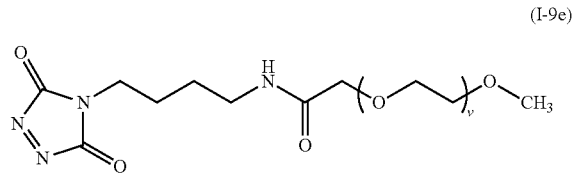
(I-9e)

To N-(4-(3,5-dioxo-1,2,4-triazolidin-4-yl)butyl)-2-methoxy(polyethyleneglycol)-acetamide (I-9d: 16 mg, 2.99 μmol) in CH₃CN (59.7 μL) was added pyridine (0.239 μL, 2.96 μmol) and N-Bromosuccinimide (NBS) 0.5M in DMF (5.91 μL, 2.96 μmol). The mixture was agitated at room temperature for 15 minutes (color changed to red-pink), and then used as is in the following conjugation step.

Conjugation to CRM197 to Form Conjugate (9A):

To CRM197 (3.00 μL, 0.0015 μmol) in Tris HCl pH 7.4 0.1M (50.0 μL) was added N-(4-(3,5-dioxo-3H-1,2,4-triazol-4(5H)-yl)butyl)-2-methoxy(polyethyleneglycol)-acetamide (0.333 μL, 0.015 μmol). The mixture was agitated at room temperature for 30 minutes, and then more N-(4-(3,5-dioxo-3H-1,2,4-triazol-4(5H)-yl)butyl)-2-methoxy(polyethyleneglycol)-acetamide was added (2 uL, 0.09 μmol). The mixture was stirred for another 15 minutes. Sodium dodecyl sulfate polyacrylamide gel electrophoresis (SDS-PAGE) showed almost no more unmodified CRM197, and multiple higher MW bands for multiple conjugations.

Examples 10, 11 and 12 illustrate conjugations with Chymotrypsinogen A.

Example 10

Comparator

Conjugation of Chymotrypsinogen A with PTAD (10A):

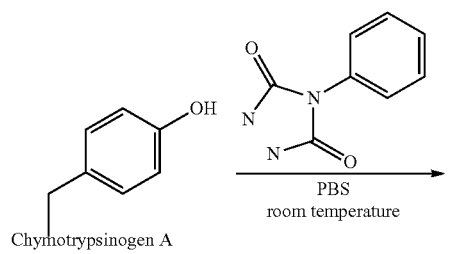

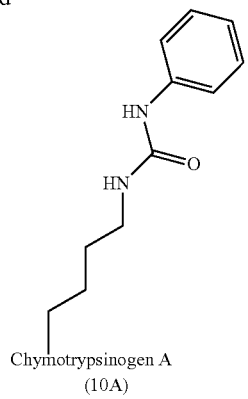
Chymotrypsinogen A
(10A)

To Chymotrypsinogen A (0.077 mg, 0.003 μmol) in PBS pH 7.2 (100 μL) was added a freshly made solution of PTAD (1.00 μL, 0.100 μmol) in CH₃CN. The mixture was agitated at room temperature for 30 minutes. The mixture was then desalted using a 7K MWCO Zeba spin column. LCMS ESI: 25657 (+0), 25777 (+1).

Example 11

Conjugation of Chymotrypsinogen A with PTAD (11A):

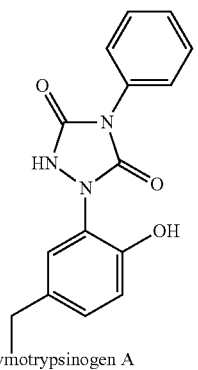
(11A)

Chymotrypsinogen A

To Chymotrypsinogen A (0.077 mg, 0.003 μmol) in Tris HCl 100 mM pH 7.4 (100 μL) was added a freshly made solution of PTAD (1.00 μL, 0.100 μmol) in CH₃CN. The mixture was agitated at room temperature for 30 minutes. The mixture was desalted using a 7K MWCO Zeba spin column. LCMS ESI: 25658 (+0), 25832 (+1).

Example 12

Conjugation of Chymotrypsinogen A with 4-methyl-3H-1,2,4-triazole-3,5(4H)-dione (12A):

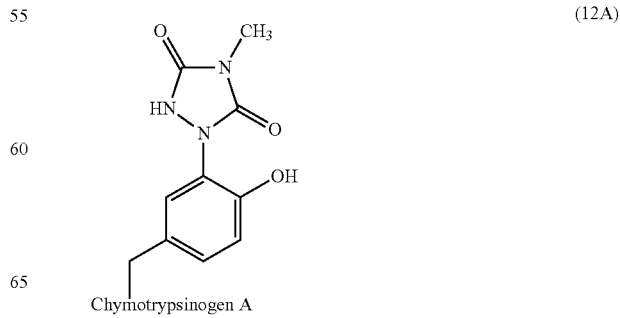
(12A)

Chymotrypsinogen A

To Chymotrypsinogen A (0.050 mg, 0.002 μmol) in Tris HCl 100 mM pH 7.4 (80 μL) was added 3 additions of 4-methyl-3H-1,2,4-triazole-3,5(4H)-dione (0.200 μL, 0.010 μmol) in $CH_3CN$ every minute (total of 15 equivalents added). The mixture was agitated at room temperature for 30 minutes. The mixture was desalted using a 7K MWCO Zeba spin column. LCMS ESI: 25662 (+0), 25774 (+1).

Example 13

Conjugation of CRM197 with 4-(2,3-bis(prop-2-ynyloxy)propyl)-3H-1,2,4-triazole-3,5(4H)-dione (13A):

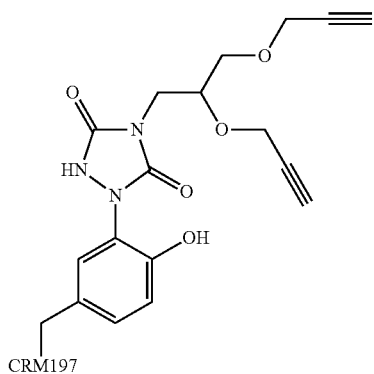

(13A)

Preparation of Intermediate tert-butyl 2,3-bis(prop-2-ynyloxy)propylcarbamate (I-13a):

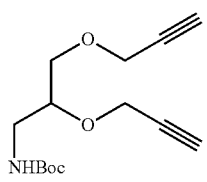

(I-13a)

To tert-butyl 2,3-dihydroxypropylcarbamate (1.912 g, 10 mmol) in DMF (33.3 mL) at 0° C. was added propargyl bromide (3.45 mL, 40.0 mmol), and then potassium hydroxide (2.244 g, 40.0 mmol) slowly. The mixture was stirred at room temperature for 16 h. Water was added to the mixture, and then extracted twice with AcOEt, washed with brine, dried over MgSO4, filtered, and concentrated. The crude product was purified by silica gel chromatography (0-20% AcOEt/heptane), giving tert-butyl 2,3-bis(prop-2-ynyloxy)propylcarbamate (I-13a: 1.583 g, 59%) as a colorless oil. $^1H$ NMR (400 MHz, $CDCl_3$) δ ppm 1.38-1.53 (m, 9 H) 2.47 (s, 2 H) 3.12-3.33 (m, 1 H) 3.46 (m, 1 H) 3.58-3.74 (m, 2 H) 3.76-3.91 (m, 1 H) 4.21 (t, J=1.77 Hz, 2 H) 4.26-4.42 (m, 2 H) 4.93 (br. s., 1 H).

Preparation of Intermediate 2,3-bis(prop-2-ynyloxy)propan-1-amine (I-13b):

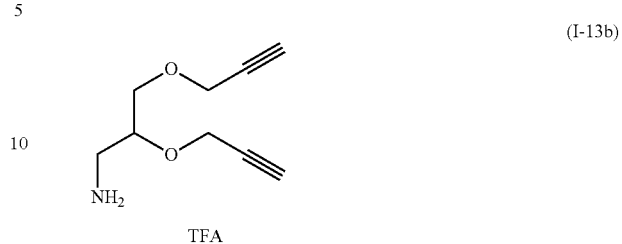

(I-13b)

To tert-butyl 2,3-bis(prop-2-ynyloxy)propylcarbamate (I-13a:1.583 g, 5.92 mmol) in CH2Cl2 (23.69 mL) at 0° C. was added TFA (4.56 mL, 59.2 mmol). The mixture was stirred at room temperature for 2 h. Concentrated, and put on pump for 16 h, giving 2,3-bis(prop-2-ynyloxy)propan-1-amine as a yellow oil used as is for next step. LC-MS (M+1) 168.1, t=0.44 minute.

Preparation of Intermediate ethyl 2-(2,3-bis(prop-2-ynyloxy)propylcarbamoyl)hydrazinecarboxylate (I-13c):

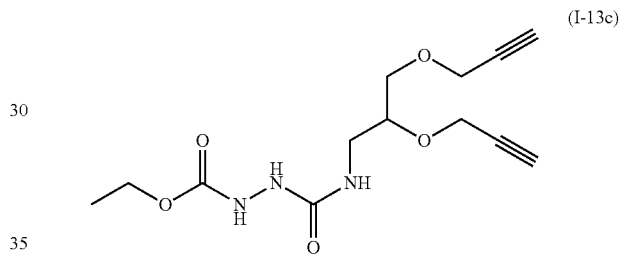

(I-13c)

To 4-nitrophenyl chloroformate (1084 mg, 5.38 mmol) in THF (18 mL) at 0° C. was added ethyl carbazate (560 mg, 5.38 mmol) and Et3N (2.98 mL, 21.52 mmol). The mixture was stirred at 0° C. for 1 h. Then more Et3N (2.98 mL, 21.52 mmol) was added, followed by a solution of 2,3-bis(prop-2-ynyloxy)propan-1-amine (I-13b: 5.92 mmol) in 5 mL THF, and the mixture was stirred at room temperature for 30 min. Water was added, extracted twice with AcOEt, dried over MgSO4, filtered, and concentrated. The crude product was purified by silica gel chromatography (40-100% AcOEt/heptane), giving ethyl 2-(2,3-bis(prop-2-ynyloxy)propylcarbamoyl)hydrazinecarboxylate (I-13c: 855 mg, 54%) as a light yellow oil. LC-MS (M+1) 298.2, t=0.75 minute.

Preparation of Intermediate 4-(2,3-bis(prop-2-ynyloxy)propyl)-1,2,4-triazolidine-3,5-dione (I-13d):

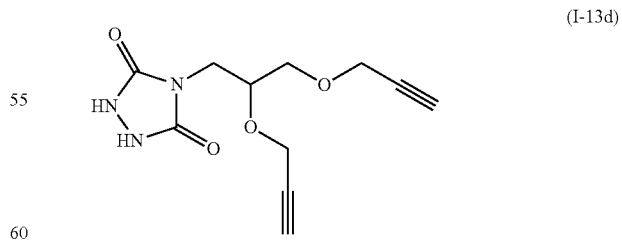

(I-13d)

To ethyl 2-(2,3-bis(prop-2-ynyloxy)propylcarbamoyl)hydrazinecarboxylate (I-13c: 855 mg, 2.88 mmol) in EtOH (14.400 mL) was added potassium carbonate (1590 mg, 11.50 mmol). The mixture was stirred at 65° C. for 16 h. After cooling to room temperature, the mixture was concentrated. HCl 1N was added up to pH-3, and then extracted with AcOEt twice, washed with brine, dried over MgSO4, filtered and concentrated. The residue was purified by silica gel chromatography (30-100% AcOEt/heptane), and then repurified by silica gel chromatography (0-20% MeOH/CH2Cl2), giving 4-(2,3-bis(prop-2-ynyloxy)propyl)-1,2,4-triazolidine-3,5-dione (I-13d: 238 mg, 33%) as a colorless oil. LC-MS (M+1) 252.1, t=0.72 minute. $^1$H NMR (400 MHz, CD$_3$CN) δ ppm 2.69 (t, J=2.27 Hz, 1 H) 2.76 (t, J=2.27 Hz, 1 H) 3.47-3.69 (m, 4 H) 3.93-4.04 (m, 1 H) 4.20 (d, J=2.27 Hz, 2 H) 4.22-4.28 (m, 2 H).

Preparation of Intermediate 4-(2,3-bis(prop-2-ynyloxy)propyl)-3H-1,2,4-triazole-3,5(4H)-dione (I-13e):

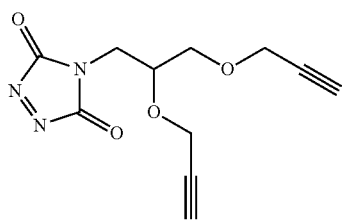

(I-13e)

To 4-(2,3-bis(prop-2-ynyloxy)propyl)-1,2,4-triazolidine-3,5-dione (I-13d: 50 mg, 0.199 mmol) in CH$_2$Cl$_2$ (1.99 mL) was added SiO2-HNO3 (150 mg). The mixture was stirred at room temperature for 15 minutes, then filtered, concentrated in vacuo and dried giving 4-(2,3-bis(prop-2-ynyloxy)propyl)-3H-1,2,4-triazole-3,5(4H)-dione (I-13e: 50 mg, quantitative) as a red oil.

Conjugation to CRM197 to Form Conjugate (13A):

To CRM197 (0.001 μmol) in Tris HCl 100 mM pH 7.4 (40.0 μL) was added seven portions of 4-(2,3-bis(prop-2-ynyloxy)propyl)-3H-1,2,4-triazole-3,5(4H)-dione (I-13e: 0.200 μL, 0.005 μmol) in CH$_3$CN every minute (total of 35 equivalents). The mixture was agitated at room temperature for 30 minutes. LCMS ESI: 58661.0 (+1), 58911.5 (+2), 59161.5 (+3), 59409.5 (+4), 59660.5 (+5).

Example 14

Conjugation of CRM197 with 4-(4-(2,5-dioxo-2,5-dihydro-1H-pyrrol-1-yl)butyl)-3H-1,2,4-triazole-3,5 (4H)-dione (14A):

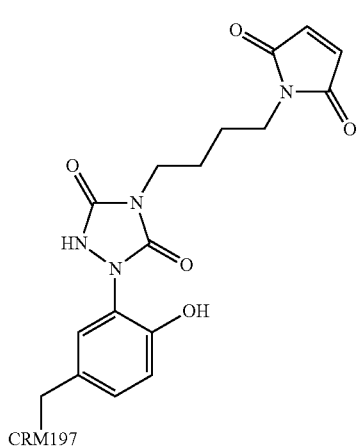

(14A)

Preparation of Intermediate 4-(4-aminobutyl)-1,2,4-triazolidine-3,5-dione hydrochloride (I-14a):

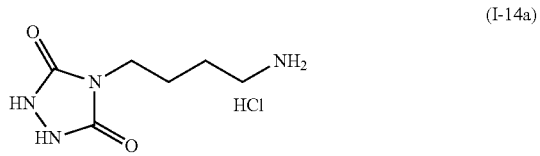 [SMILES: NCCCCn1c(=O)[nH][nH]c1=O ; Cl]

(I-14a)

To tert-butyl 4-(3,5-dioxo-1,2,4-triazolidin-4-yl)butylcarbamate (I-8b: 590 mg, 2.167 mmol) in CH2Cl2 (10.800 mL) was added HCl in dioxane (5.42 mL, 21.67 mmol) dropwise. The mixture was stirred at room temperature for 4 h, then concentrated and dried on pump, giving 4-(4-aminobutyl)-1,2,4-triazolidine-3,5-dione hydrochloride (I-14a: 461 mg, quantitative) as a beige solid. $^1$H NMR (400 MHz, dmso-d6) δ ppm 1.41-1.71 (m, 4 H) 2.68-2.87 (m, 2 H) 3.37 (t, J=6.44 Hz, 2 H) 7.86 (br. s., 2 H) 10.13 (s, 2 H).

Preparation of Intermediate 4-(4-(2,5-dioxo-2,5-dihydro-1H-pyrrol-1-yl)butyl)-1,2,4-triazolidine-3,5-dione (I-14b):

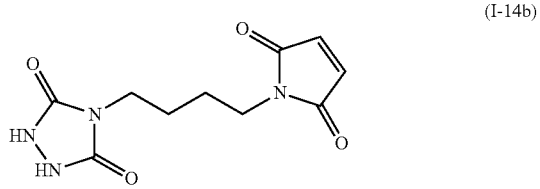 [SMILES: O=C1C=CC(=O)N1CCCCn1c(=O)[nH][nH]c1=O]

(I-14b)

To 4-(4-aminobutyl)-1,2,4-triazolidine-3,5-dione hydrochloride (I-14a: 42 mg, 0.201 mmol) in NaHCO3 sat aqueous solution (1.006 mL) at 0° C. was added N-methoxycarbonylmaleimide (31.2 mg, 0.201 mmol). The mixture was stirred at 0° C. for 1 h, and then at room temperature for 2 h. The mixture was purified by preparative hplc (0-60% CH3CN/ (0.1% TFA in H2O)), and then lyophilized, giving 4-(4-(2,5-dioxo-2,5-dihydro-1H-pyrrol-1-yl)butyl)-1,2,4-triazolidine-3,5-dione (I-14b: 10 mg, 20%) a white solid. LC-MS (M+1) 253.3, t=0.89 minute. $^1$H NMR (400 MHz, CD$_3$CN) δ ppm 1.51-1.62 (m, 4H) 3.45 (t, J=6.44 Hz, 2H) 3.49 (t, J=6.44 Hz, 2 H) 6.76 (s, 2 H) 7.52 (br. s., 2 H).

Preparation of Intermediate 4-(4-(2,5-dioxo-2,5-dihydro-1H-pyrrol-1-yl)butyl)-3H-1,2,4-triazole-3,5 (4H)-dione (I-14c):

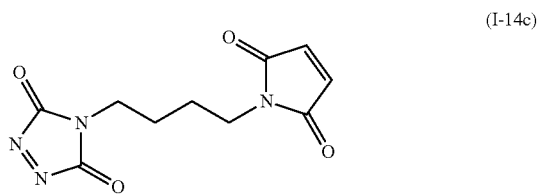 [SMILES: O=C1C=CC(=O)N1CCCCN1C(=O)N=NC1=O]

(I-14c)

To 4-(4-(2,5-dioxo-2,5-dihydro-1H-pyrrol-1-yl)butyl)-1,2,4-triazolidine-3,5-dione (I-14b: 6 mg, 0.024 mmol) in CH$_2$Cl$_2$ (0.95 mL) was added SiO2-HNO3 (50 mg). The mixture was stirred at room temperature for 15 minutes, then filtered, concentrated in vacuo and dried giving 4-(4-(2,5-dioxo-2,5-dihydro-1H-pyrrol-1-yl)butyl)-3H-1,2,4-triazole-3,5(4 H)-dione (I-14c: 6 mg, quantitative) as a pink solid. $^1$H NMR (400 MHz, CD$_3$CN) δ ppm 1.52-1.71 (m, 4 H) 3.49 (t, J=6.44 Hz, 2 H) 3.59 (t, J=6.69 Hz, 2 H) 6.77 (s, 2H).

Conjugation to CRM197 to Form Conjugate (14A):

To CRM197 (0.0005 μmol) in Tris HCl 1M pH 7.4 (20.0 μL) at 4° C. was added four portions of 4-(4-(2,5-dioxo-2,5-dihydro-1H-pyrrol-1-yl)butyl)-3H-1,2,4-triazole-3,5(4H)-dione (I-14c: 0.100 μL, 0.0025 μmol) in acetonitrile every minute (total of 20 equivalents). The mixture was agitated at 4° C. for 30 minutes. LCMS ESI: 58661 (+1), 58912 (+2), 59162 (+3), 59413 (+4), 59663 (+5).

Example 15

Conjugation of GBS80 with 4-(4-(2,5-dioxo-2,5-dihydro-1H-pyrrol-1-yl)butyl)-3H-1,2,4-triazole-3,5(4H)-dione (15A):

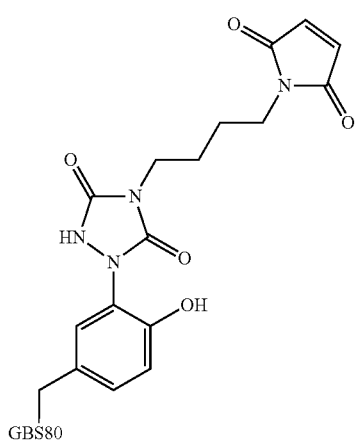

(15A)

To GBS80 (MW=52836, 0.0004 μmol) in Tris 0.5M pH 7.4 (40 μL) at 4° C. was added eight portions of 4-(4-(2,5-dioxo-2,5-dihydro-1H-pyrrol-1-yl)butyl)-3H-1,2,4-triazole-3,5(4H)-dione (I-14c: 0.2 μL, 0.004 μmol) in acetonitrile every minute (total of 80 equivalents). The mixture was agitated at 4° C. for 15 minutes. The mixture was desalted and buffer exchanged to ammonium carbonate pH 8.0 two times using Zeba 7K MWCO spin columns. LCMS ESI: 53338 (+2), 53588 (+3), 53838 (+4), 54088 (+5).

Example 16

Conjugation of GBS59 with 4-(4-(2-(2-(prop-2-ynyloxy)ethoxy)ethoxy)phenyl)-3H-1,2,4-triazole-3,5(4H)-dione (16A):

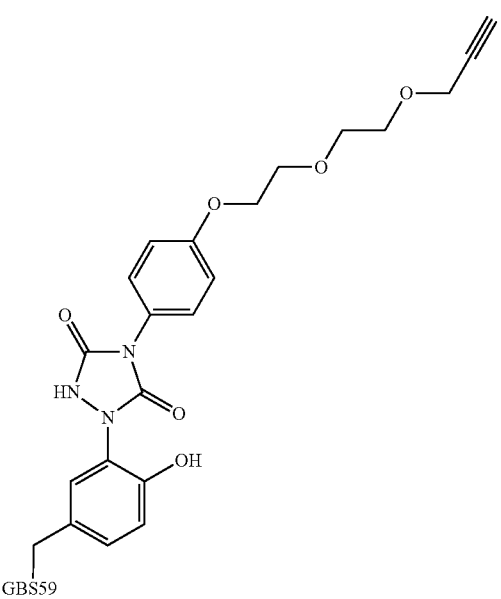

(16A)

To GBS59 (MW=77549, 0.04 μmol) in Tris 0.25M pH 7.4 (40 μL) at 4° C. was added six portions of 4-(4-(2-(2-(prop-2-ynyloxy)ethoxy)ethoxy)phenyl)-3H-1,2,4-triazole-3,5(4H)-dione (I-6e: 8.05 μL, 0.20 μmol) in acetonitrile every minute (total of 30 equivalents). The mixture was agitated at 4° C. for 30 minutes. The mixture was desalted and buffer exchanged to PBS pH 7.4 three times using Zeba 7K MWCO spin columns. LCMS ESI: 77879 (+1), 78202 (+2).

Example 17

Conjugation of CRM197 with PTAD and pentyn-1-amine (17A):

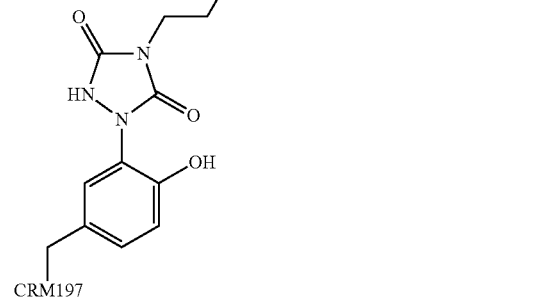

(17A)

To CRM197 (0.017 μmol) in Tris HCl 100 mM pH 7.4 (680 μL) was added pentyn-1-amine (6.7 μL, 68 μmol), and then twelve portions of PTAD (3.4 μL, 0.17 μmol) in CH₃CN every minute (total of 120 equivalents). The mixture was agitated at room temperature for 30 minutes. LCMS ESI: 58575 (+1), 58741 (+2), 58906 (+3), 59071 (+4).

Example 18

Conjugation of GBS80 with 4-(2-(2-(2-(2-azidoethoxy)ethoxy)ethyl)-3H-1,2,4-triazole-3,5(4H)-dione (18A):

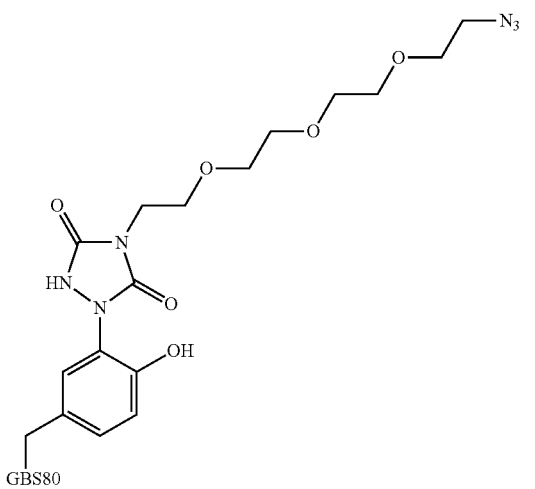

Preparation of Intermediate ethyl 16-azido-4-oxo-8,11,14-trioxa-2,3,5-triazahexadecan-1-oate (I-18a):

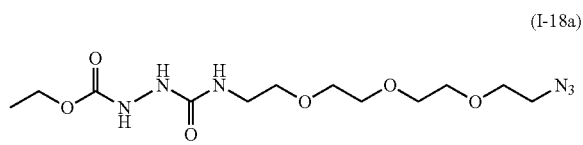 [SMILES: CCOC(=O)NNC(=O)NCCOCCOCCOCCN=[N+]=[N-]]

To 4-nitrophenyl chloroformate (1008 mg, 5.00 mmol) in THF (17 mL) at 0° C. was added ethyl carbazate (0.521 g, 5 mmol) and Et3N (2.08 mL, 15.00 mmol). The mixture was stirred at 0° C. for 30 min. Then a solution of 11-azido-3,6,9-trioxaundecan-1-amine (1.09 ml, 5.50 mmol) in 2 mL THF, and the mixture was stirred at room temperature for 16 h. Water was added, extracted twice with AcOEt, dried over MgSO4, filtered, and concentrated. The crude product was purified by silica gel chromatography (40-100% AcOEt/heptane, then 5% MeOH/AcOEt), giving ethyl 16-azido-4-oxo-8,11,14-trioxa-2,3,5-triazahexadecan-1-oate (I-18a: 1.23 g, 71%) as a colorless oil. LC-MS (M+1) 349.4, t=1.63 minute.

Preparation of Intermediate 4-(2-(2-(2-(2-azidoethoxy)ethoxy)ethoxy)ethyl)-1,2,4-triazolidine-3,5-dione (I-18b):

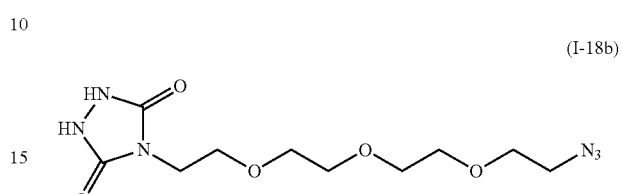

To ethyl ethyl 16-azido-4-oxo-8,11,14-trioxa-2,3,5-triazahexadecan-1-oate (I-18a: 1.15 g, 3.30 mmol) in EtOH (16.5 mL) was added potassium carbonate (1825 mg, 13.2 mmol). The mixture was stirred at 65° C. for 16 h. After cooling to room temperature, the mixture was concentrated. HCl 1N was added up to pH-3, and then extracted with AcOEt twice, washed with brine, dried over MgSO4, filtered and concentrated. The residue was purified by silica gel (25-100% AcOEt/heptane, then 5% MeOH/AcOEt), giving 4-(2-(2-(2-(2-azidoethoxy)ethoxy)ethyl)-1,2,4-triazolidine-3,5-dione (I-18b: 183 mg, 18%) as a colorless oil. LC-MS (M+1) 303.3, t=0.71 minute. 1H NMR (400 MHz, CD3CN) δ ppm 3.30 (s, 2 H) 3.40 (t, J=4.80 Hz, 2 H) 3.50-3.71 (m, 12 H).

Preparation of Intermediate 4-(2-(2-(2-(2-azidoethoxy)ethoxy)ethyl)-3H-1,2,4-triazole-3,5(4H)-dione (I-18c):

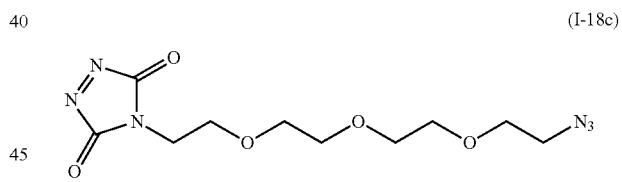

To 4-(2-(2-(2-(2-azidoethoxy)ethoxy)ethyl)-1,2,4-triazolidine-3,5-dione (I-18c: 3 mg, 9.92 umol) in CH₂Cl₂ (1 mL) was added SiO2-HNO3 (25 mg). The mixture was stirred at room temperature for 15 minutes, then filtered, concentrated in vacuo and dried giving 4-(2-(2-(2-(2-azidoethoxy)ethoxy)ethyl)-3H-1,2,4-triazole-3,5(4H)-dione (I-18c: 3 mg, quantitative) as a pink oil.

Conjugation to GBS80 to Form Conjugate (18A):

To GBS80 (MW=52836, 0.001 μmol) in Tris 0.5M pH 7.4 (67 μL) at 4° C. was added four portions of 4-(2-(2-(2-(2-azidoethoxy)ethoxy)ethyl)-3H-1,2,4-triazole-3,5(4H)-dione (I-18c: 0.25 μL, 0.005 μmol) in acetonitrile every minute (total of 20 equivalents). The mixture was agitated at 4° C. for 30 minutes. The mixture was desalted and buffer exchanged to PBS pH 7.4 two times using Zeba 7K MWCO spin columns. LCMS ESI: 53137 (+1), 53438 (+2), 53738 (+³).

Example 19

General Procedure for Glycosylation with Trichloroacedimidate Donors

To a stirred solution of acceptor (1 mmol) and donor (1.2 mmol) in anhydrous $CH_2Cl_2$ (15 ml) containing activated 4 Å MS (0.75 g), TMSOTf (0.2-0.4 mmol) was added at 0° C. The mixture was stirred for 30 min when TLC (2:1 cyclohexane-EtOAc) showed the reaction was complete. Then the mixture was neutralized with triethylamine, filtered through a celite pad, and the filtrate was concentrated. Chromatography of the residue (cyclohexane-EtOAc) gave the desired product. This procedure was adopted in the syntheses outlines in Examples 21-22 (below).

General Procedure for Delevulinoylation

To a solution of the 3-O-Lev oligosaccharide (1 mmol) in $CH_2Cl_2$ (25 ml) ethylenediamine (0.26 ml, 4 mmol) and AcOH (0.29 ml, 5 mmol) were added at 0° C. A white solid was formed, and the suspension was stirred for 5-6 h at 50° C., when the deprotection was complete (TLC, cyclohexane-EtOAc 2:1). The mixture was concentrated and chromatography of the residue (cyclohexane-EtOAc) yielded the delevulinoylated product. This procedure was adopted in the syntheses outlines in Examples 15-16 (below).

Example 20

Synthesis of Rhamnoside 4

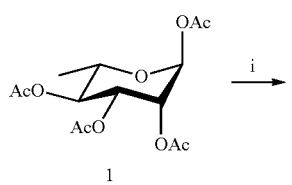

1

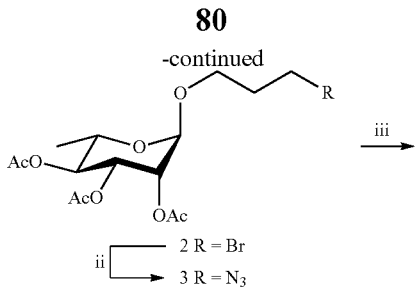

2 R = Br
3 R = $N_3$

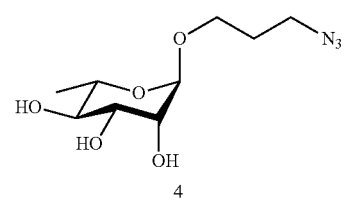

4

Reactions leading to rhamnoside 4: i. 3-Bromopropanol, $BF_3 \cdot Et_2O$, $CH_2Cl_2$, 83%; ii. $NaN_3$, DMF, 71%; iii. NaOMe, MeOH, 89%.

Example 21

Synthesis of Tetrasaccharide 12

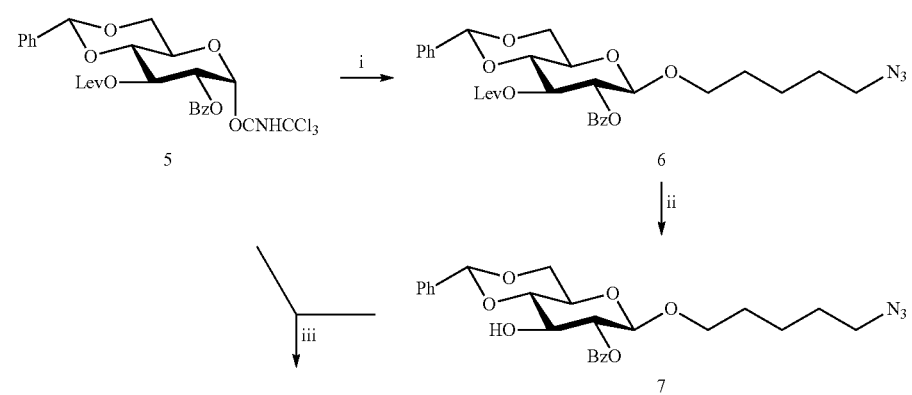

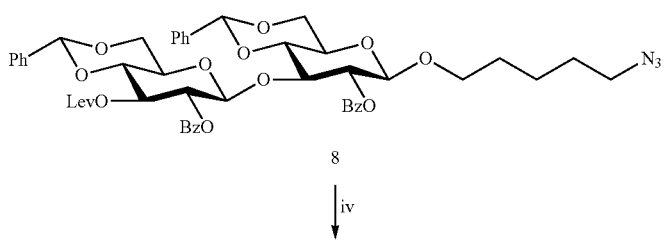

8

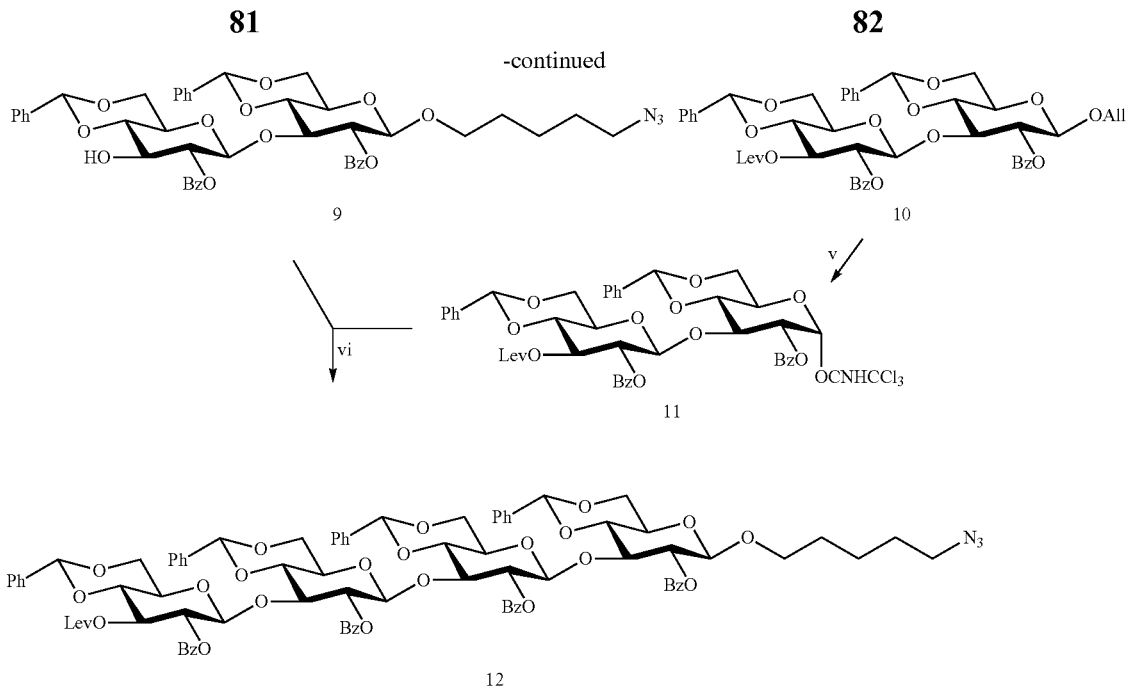

Reactions leading to tetrasaccharide 12: i. 5-azidopentanol, 20% TMSOTf, CH$_2$Cl$_2$, 53%; ii. H$_2$NCH$_2$CH$_2$NH$_2$·AcOH, CH$_2$Cl$_2$, 50° C., 69%; iii. 20% TMSOTf, CH$_2$Cl$_2$, 73%; iv. H$_2$NCH$_2$CH$_2$NH$_2$·AcOH, CH$_2$Cl$_2$, 50° C., 98%; v. 1,5-Cyclooctadiene-bis(methyldiphenylphosphine)-Iridium-hexafluorophosphate catalyst, THF; I$_2$, H$_2$O; CCl$_3$CN, DBU, CH$_2$Cl$_2$, 88% (over two steps); vi. 20% TMSOTf, CH$_2$Cl$_2$, 83%.

Example 22

Synthesis of Hexasaccharide 15

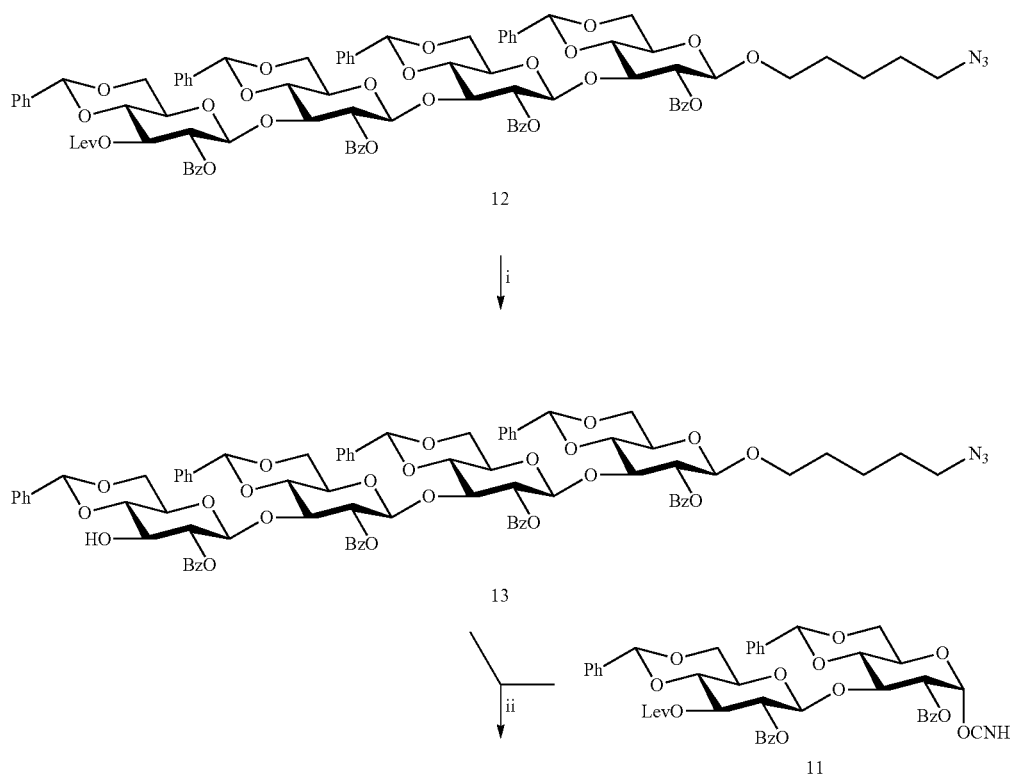

-continued

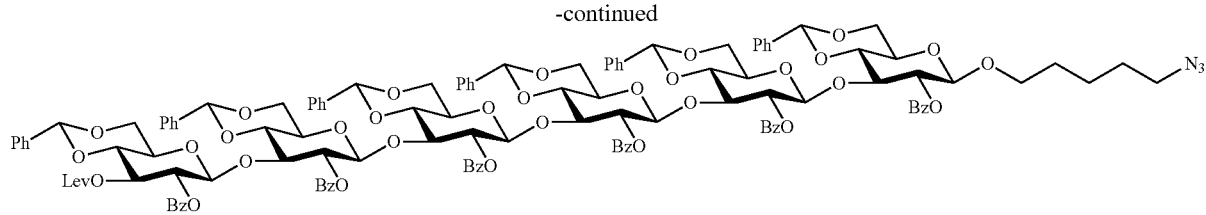

14

↓ iii

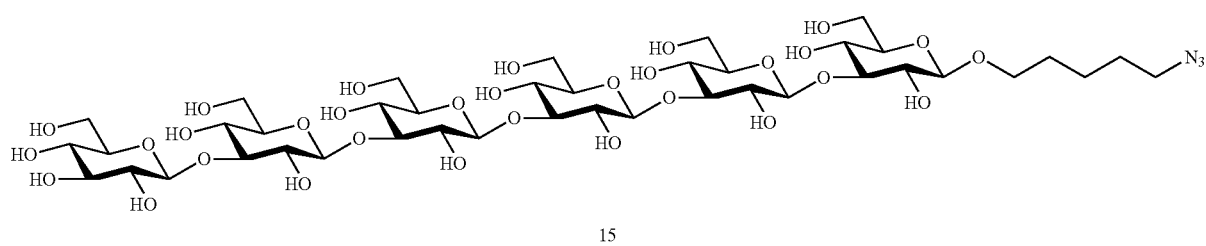

15

Scheme 3. Reactions leading to hexasaccharide 15: i. H$_2$NCH$_2$CH$_2$NH$_2$•AcOH, CH$_2$Cl$_2$, 50° C., 92%; iii. 40% TMSOTf, CH$_2$Cl$_2$, 92%; iii. 9:AcOH—H$_2$O, 50° C.: NaOMe, MeOH 93% (over two steps).

Example 23

Conjugation of Conjugate 7A with Azide Modified-Saccharides 4 and 15:

A premixed solution of 5 mM CuSO$_4$.5H$_2$O (5 µl) and 25 mM THPTA (5 µl) was added under nitrogen atmosphere to a solution of Conjugate 7A (300 µg, 0.005 µmol) in 100 mM NaPi pH 7 (70 µl) and azide 4 (0.1 µmol) or 15 (0.15 µmol), followed by 5 mM aminoguanidine hydrochloride (5 µl) and 10 mM sodium ascorbate (5 µl). The mixture was stirred at ambient temperature for 1.5 h, then the glycoprotein was washed on a 30 KDa Amicon centrifugal filter with 10 mM EDTA/10 mM NaPi pH 7 (2×100 µl) and 10 mM NaPi pH 7 (8×100 µl), and subsequently reconstituted with 10 mM NaPi pH 7. For conjugation with azide 4, the yield of recovered glycoprotein was 95%. For conjugation with azide 15, the yield of recovered glycoprotein (conjugate A) was 85%. The conjugation with azide 15 is outlined in FIG. 1.

Figure 2A:
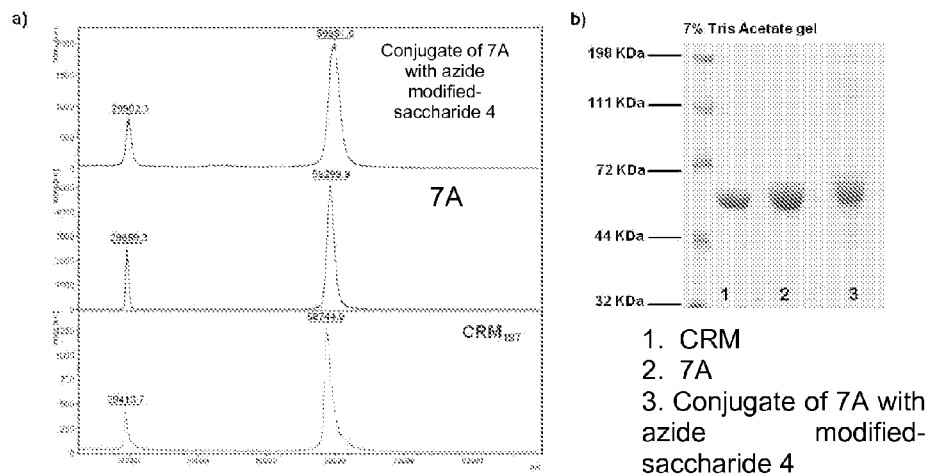
FIGS. 2A and 2B show the results of SDS page analysis and MALDI-TOF spectrometry on the glycoconjugate resulting from conjugation of Conjugate 7A with azide modified-saccharides.
Figure 2B:
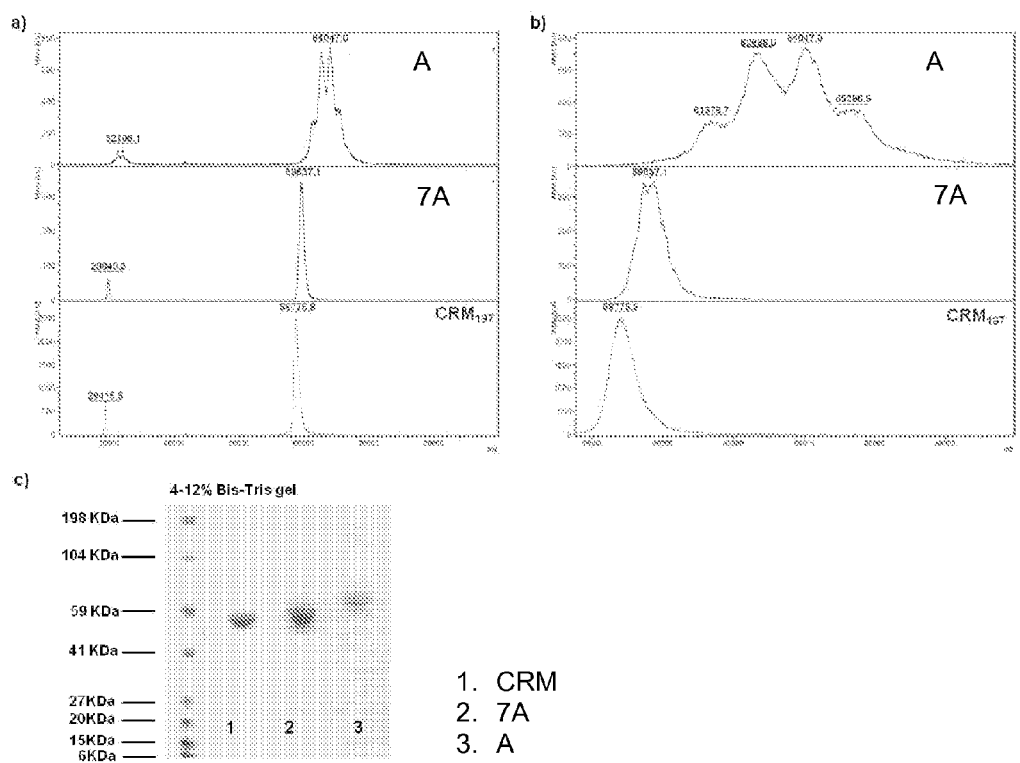

The inventors have also carried out conjugation using different concentrations of reagents, namely 10 mM CuSO$_4$.5H$_2$O, 25 mM aminoguanidine hydrochloride and THPTA at a ratio of 5:1 with 0.25 µmol/ml Cu(I). In this alternative method the mixture was stirred for 1 hour, after which 40 equiv. of azide was added, followed by continuous stirring for a further 2 hours. The loading of the glycoconjugate was determined by matrix-assisted laser desorption ionization time-of-flight mass spectrometry (MALDI-TOF MS; UltraFlex III MALDI-TOF/TOF instrument, Bruker Daltonics) in linear mode and with positive ion detection. The samples for analysis were prepared by mixing 2.5 µl of product and 2.5 µl of Super DHB matrix; 2.5 µl of each mixture was deposited on a samples plate, dried at rt for 10 min, and subjected to the spectrometer. Results are shown in FIGS. 2A (for the conjugate of azide 4) and 2B (for the conjugate of azide 15, i.e. conjugate A).

For SDS page analysis, the samples (5 µg) were electrophoresed on a 7% TrisAcetate gel or 4-12% Bis-Tris gel (NuPage, Invitrogen) and stained with Coomassie blue. Results are shown in FIGS. 2A (for the conjugate of azide 4, using 7% TrisAcetate gel) and 2B (for the conjugate of azide 15, i.e. conjugate A, using 4-12% Bis-Tris gel).

Example 24

Figure 3:
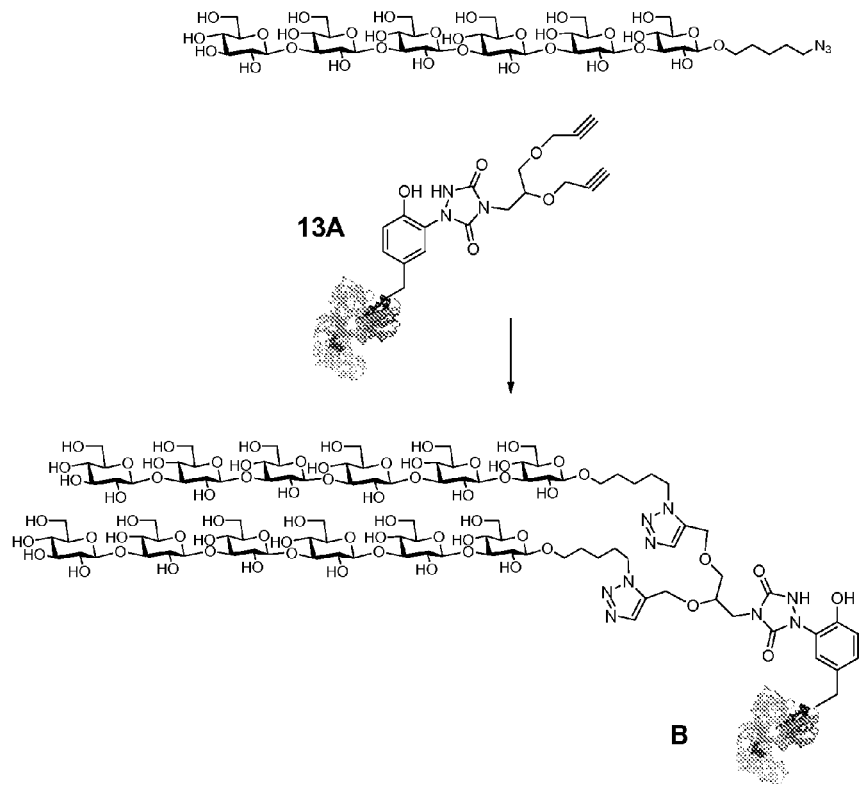
FIG. 3 shows the reaction carried out to effect conjugation of Conjugate 13A with azide modified-saccharide.

Conjugation of Conjugate 13A with Azide Modified-Saccharide 15 to Make Conjugate B:

The conjugation was carried out as shown in FIG. 3.

Example 25

Conjugation of CRM 197 to hexasaccharide via adipic acid linker to make conjugate C Comparative Example

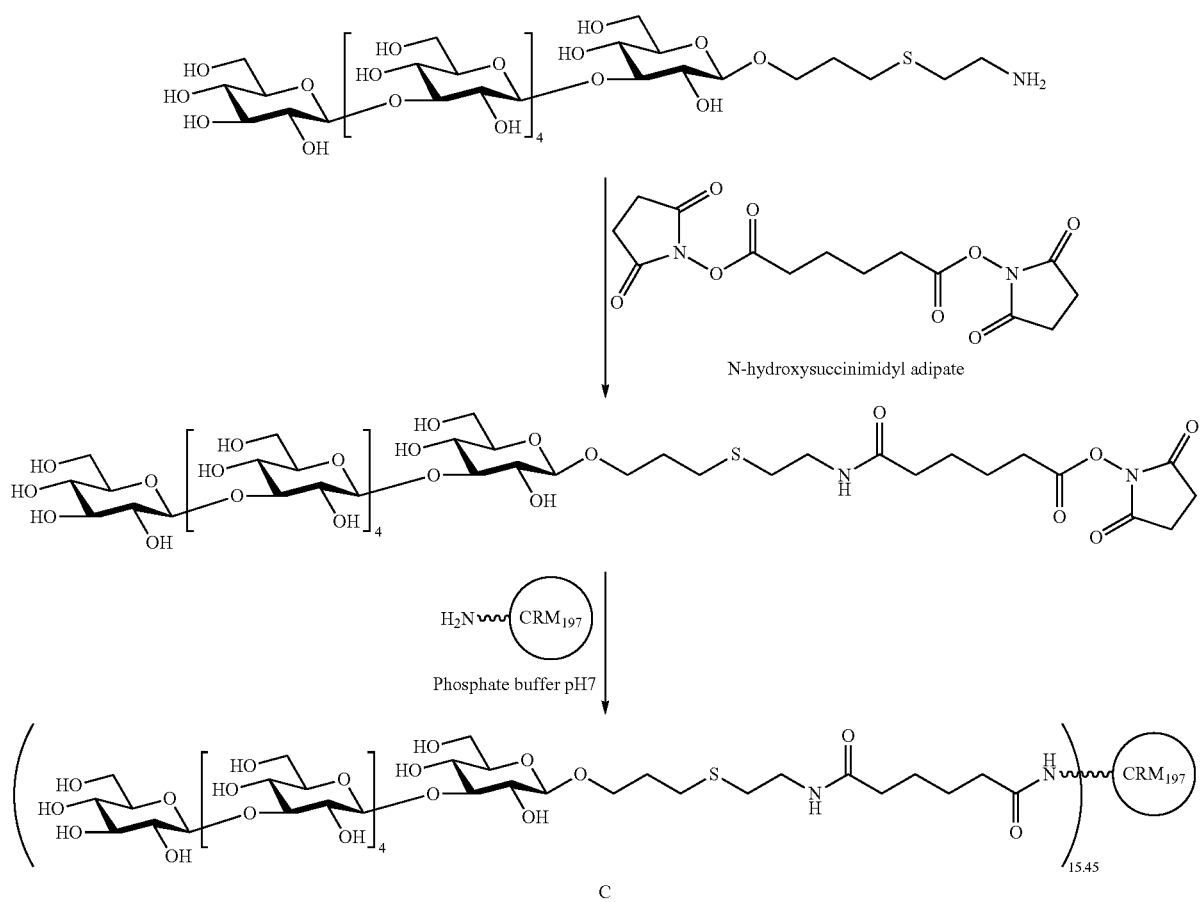

The characteristics of the various batches of azide-linked saccharide 15 and resulting hexasaccharide glycoconjugates are shown in Table 2.

TABLE 2

| Compound | MW | Average loading | µg/ml | Total/reacted Amount | Sugar µg/ml | Yield % |
|---|---|---|---|---|---|---|
| 15 | 62623 | 2.5 | 250 | 250/360 | 10.9 | 69 |
| 15 | 63247 | 3.5 | 259 | 518/880 | 15.7 | 59 |
| 15 | 63507 | 3.5 | 566 | 1132/2640 | 34 | 43 |
| B | 65592 | 5.8 | 550 | 1100/1375 | 53.4 | 80 |
| C | 80661 | 18.4 | 940 | 940/1000 | 261 | 94 |
| B | 65589 | 5.8 | 806 | 1550/2450 | 78.4 | 63 |
| C | 98467 | 32.5 | 812 | 812/1000 | 326 | 81 |
| C | 92879 | 28.4 | 737 | 737/1000 | 275 | 74 |
| C | 69005 | 9.0 | 980 | 2940/3300 | 160 | 89 |

Figure 4:
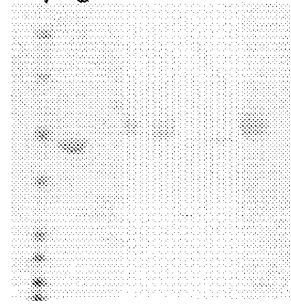
FIG. 4 shows the results of SDS page analysis and MALDI-TOF spectrometry on the glycoconjugate resulting from conjugation of Conjugate 13A with azide modified-saccharide.
Figure 4:
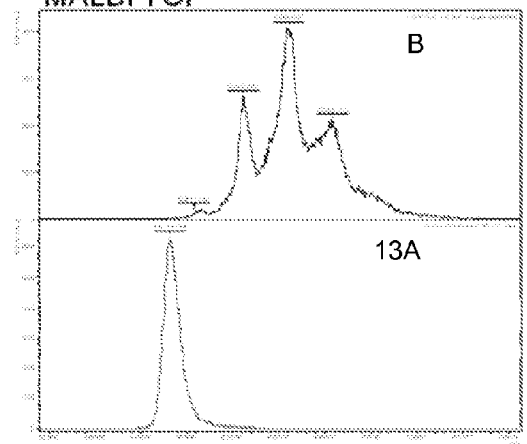
Figure 5:
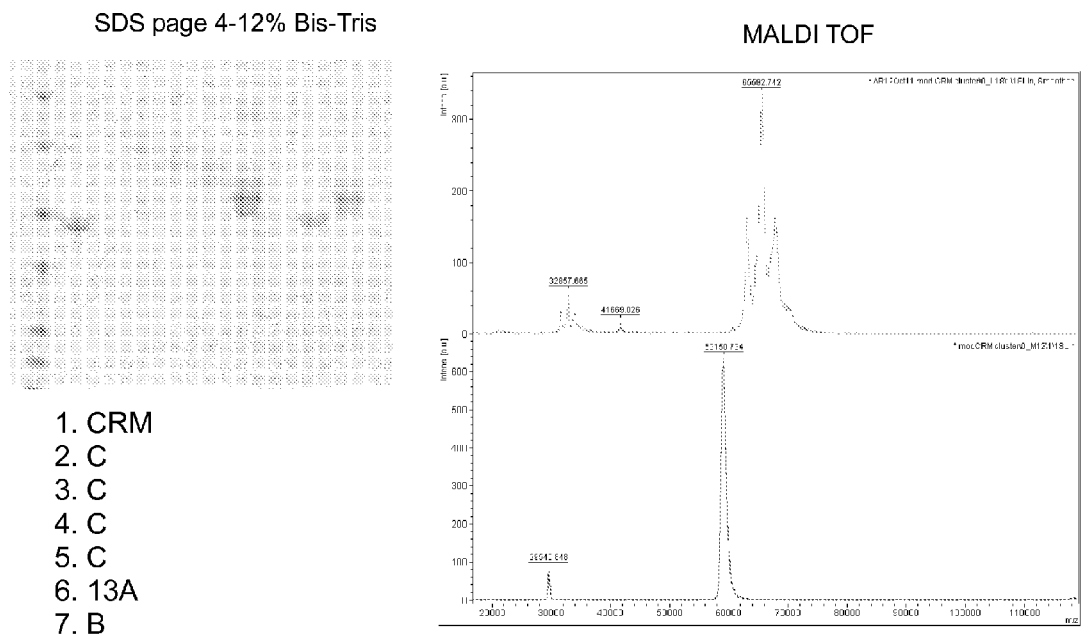
FIG. 5 shows the results of SDS page analysis and MALDI-TOF spectrometry on the glycoconjugate resulting from conjugation of Conjugate 13A with azide modified-saccharide and positive control.

The loading of the glycoconjugate was determined by matrix-assisted laser desorption ionization time-of-flight mass spectrometry (MALDI-TOF MS; UltraFlex III MALDI-TOF/TOF instrument, Bruker Daltonics) in linear mode and with positive ion detection. The samples for analysis were prepared by mixing 2.5 µl of product and 2.5 µl of Super DHB matrix; 2.5 µl of each mixture was deposited on a samples plate, dried at rt for 10 min, and subjected to the spectrometer. Results are shown in FIGS. 4 and 5.

For SDS page analysis, the samples (5 µg) were electrophoresed on a 4-12% Bis-Tris gel (NuPage, Invitrogen) and stained with Coomassie blue. Results are shown in FIGS. 4 and 5.

Example 26

Mice Immunization with Conjugate of Examples 23 to 25:
Groups of 8 CD1 mice were immunized at days 1, 14 and 28 with conjugate (2 µg saccharide antigen per dose) or negative control (PBS), both formulated with MF59 and delivered in a volume of 150 µl by subcutaneous injection. Bleedings were performed at days 0 (preimmune sera), 28 (post2 sera) and 42 (post3 sera).

ELISA Analysis of Sera:
96-well Maxisorb plates (Nunc, Thermo Fisher Scientific) were coated overnight at +4° C. with laminarin 5 µg/well in 0.05 M $Na_2CO_3$—$NaHCO_3$ buffer at pH 9.6. After coating, the plates were washed three times with 300 µl per well of phosphate saline buffer (PBS) with 0.05% Tween 20 (TPBS) at pH 7.4. A blocking step was then performed by adding 100 µl of bovine serum albumin (Fraction V, Sigma-Aldrich) at 3% in TPBS and incubating the plates for 1 h at 37° C.

Blocking solution was removed from the plates by washing three times per well with TPBS.

Figure 6:
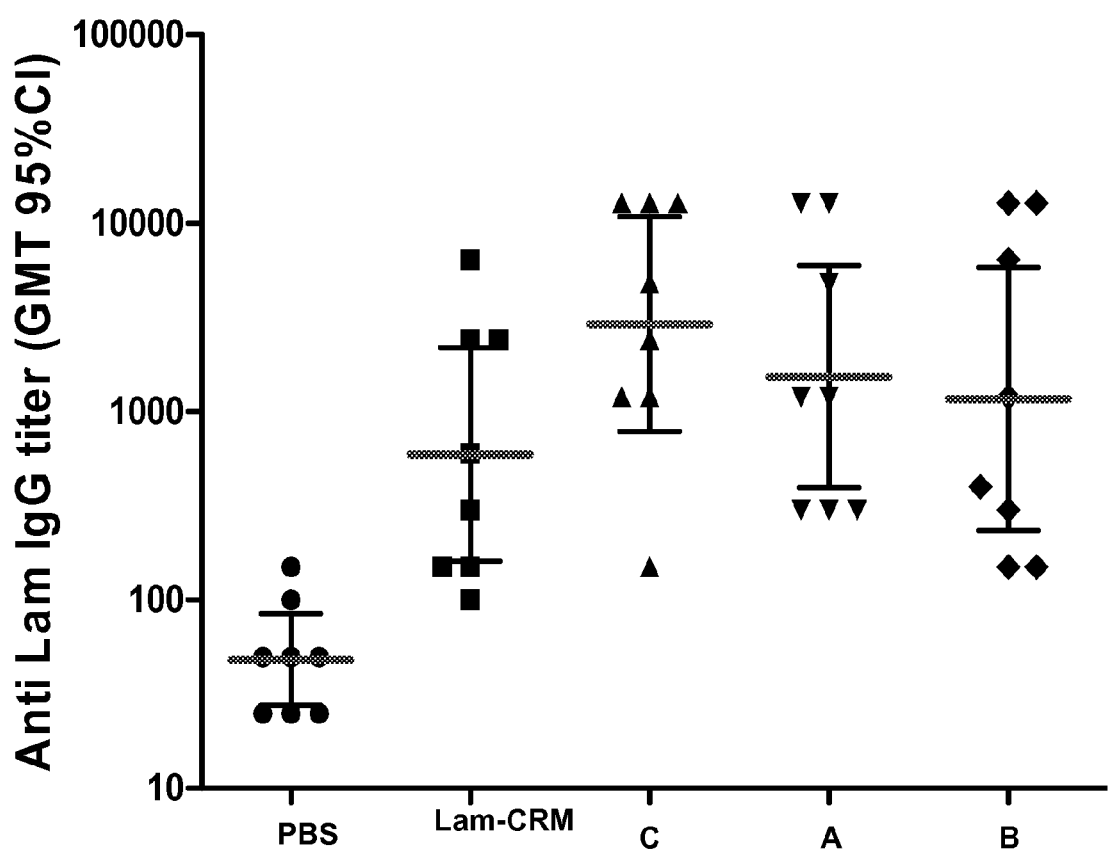
FIG. 6 compares the IgG response to different conjugates after three doses using mice sera on plates coated with Laminarin with MF59 as adjuvant.

Two hundred μl of pre-diluted serum (1:25 for preimmune, 1:100 for a reference serum, 1:50 for test sera) were added in the first well of each column of the plate, while on the other wells 100 μl of TPBS were dispensed. Eight twofold serial dilutions along each column were then performed by transferring from well to well 100 μl of sera solutions. After primary Abs dilution, plates were incubated for 2 h at 37° C. After three washes with TPBS, 100 μl TPBS solutions of secondary antibody alkaline phosphates conjugates (anti mouse IgG 1:10000) were added and the plates incubated 1 h at 37° C. After three more washes with TPBS, 100 μl/well of a 1 mg/ml of p-nitrophenyl phosphate disodium (Sigma-Aldrich) in a 1 M diethanolamine buffer (pH 9.8) was added. Plates were incubated for 30 min at room temperature at which time were read at 405 nm using a Biorad plate reader. Raw data acquisition was performed by Microplate Manager Software (Biorad). Sera titers were expressed as the reciprocal of sera dilution corresponding to a cut-off (optical density) OD=0.2. Each immunization group has been represented as the geometrical mean (GMT) of the single mouse titers. The statistical and graphical analysis was performed by GraphPad 5.0 software. Details of the immunization schedule are outlined in Table 3 (below). The IgG response to different conjugates after three doses using mice sera on plates coated with Laminarin with MF59 as adjuvant is shown in FIG. 6.

TABLE 3

| Group | Mice | Adj Name | Ant Dose | Adj | Imm | VPA | Route |
|---|---|---|---|---|---|---|---|
| 1 | 1-18 | PBS | — | MF59 | 1-2-3 | 150 μl | SC |
| 2 | 9-16 | Lam-CRM RS3002 | 2 μg | MF59 | 1-2-3 | 150 μl | SC |
| 3 | 17-24 | C | 2 μg | MF59 | 1-2-3 | 150 μl | SC |
| 4 | 25-32 | A | 2 μg | MF59 | 1-2-3 | 150 μl | SC |
| 5 | 33-40 | B | 2 μg | MF59 | 1-2-3 | 150 μl | SC |

Lam-CRM = laminarin conjugated to CRM197 (WO03/097091 and Torosantucci et al. (2005) J Exp Med 202:597-606)

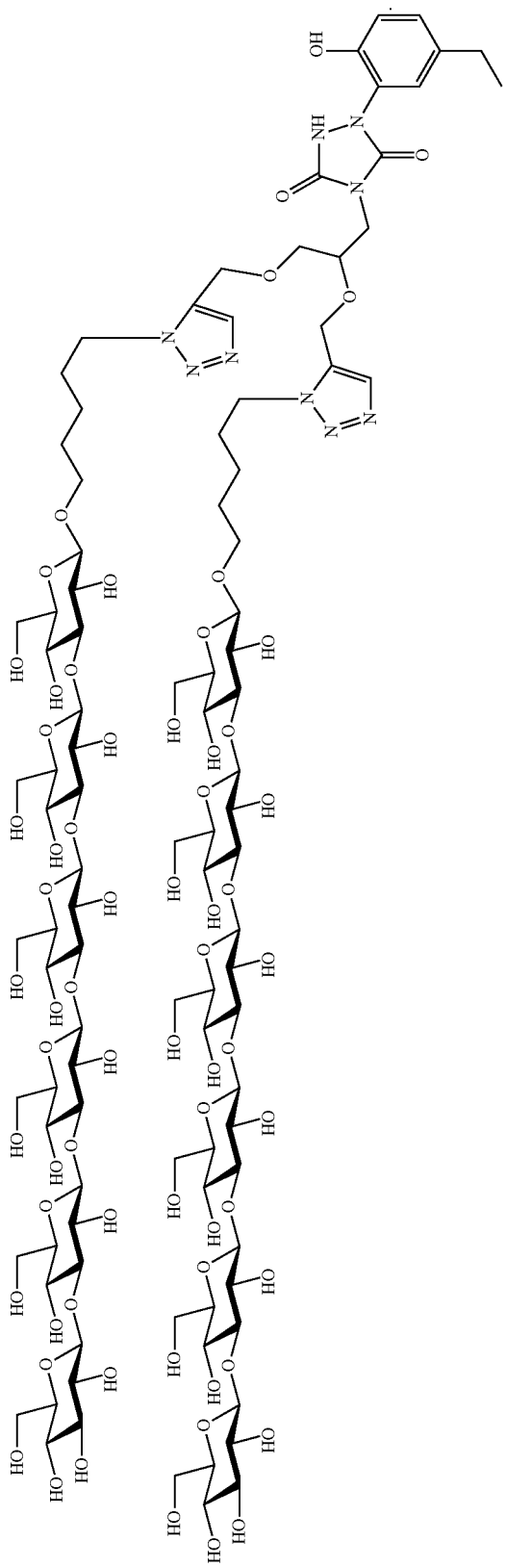

What is claimed is:

1. A tyrosine containing conjugate of diphtheria toxin mutant CRM197 having a structure:

2. A tyrosine containing conjugate of diphtheria toxin mutant CRM197 having a structure: